US012600773B2

(12) United States Patent (10) Patent No.: US 12,600,773 B2

Testani et al. (45) **Date of Patent: \*Apr. 14, 2026**

(54) TREATMENT OF DIURETIC RESISTANT HEART FAILURE PATIENTS HAVING AT LEAST ONE COPY OF THE TMPRSS6 rs855791 ALLELE

(71) Applicants: YALE UNIVERSITY, New Haven, CT (US); Novo Nordisk A/S, Bagsvaerd (DK)

(72) Inventors: Jeffrey Testani, Guilford, CT (US); Veena Rao, Cerby, CT (US); Rahul Kakkar, Weston, MA (US); Madhav N. Devalaraja, Acton, MA (US); Chih-Hung Lo, Rockville, MD (US)

(73) Assignees: Novo Nordisk A/S, Bagsvaerd (DK); Yale University, New Haven, CT (US)

( * ) Notice: Subject to any disclaimer, the term of this patent is extended or adjusted under 35 U.S.C. 154(b) by 782 days.

This patent is subject to a terminal disclaimer.

(21) Appl. No.: 17/519,082

(22) Filed: Nov. 4, 2021

(65) Prior Publication Data

US 2022/0195033 A1 Jun. 23, 2022

Related U.S. Application Data

(63) Continuation of application No. 16/482,038, filed as application No. PCT/US2018/016508 on Feb. 1, 2018, now Pat. No. 11,203,636.

(60) Provisional application No. 62/453,257, filed on Feb. 1, 2017.

(51) Int. Cl.
*C07K 16/24* (2006.01)

(52) U.S. Cl.
CPC ........ *C07K 16/248* (2013.01); *C07K 2317/76* (2013.01)

(58) Field of Classification Search
CPC ... C07K 16/248; C07K 2317/76; A61P 13/12; A61P 7/10
See application file for complete search history.

(56) References Cited

U.S. PATENT DOCUMENTS

| | | | |
|---|---|---|---|
| 5,856,135 A | 1/1999 | Tsuchiya et al. |
| 5,888,510 A | 3/1999 | Kishimoto et al. |
| 6,083,501 A | 7/2000 | Miyata et al. |
| 6,121,423 A | 9/2000 | Tsuchiya et al. |
| 6,663,864 B1 | 12/2003 | Kink et al. |
| 7,083,784 B2 | 8/2006 | Dall'Acqua et al. |
| 7,291,721 B2 | 11/2007 | Giles-Komar et al. |
| 7,414,024 B2 | 8/2008 | Blay et al. |
| 7,560,112 B2 | 7/2009 | Chen et al. |
| 7,612,182 B2 | 11/2009 | Giles-Komar et al. |
| 7,658,921 B2 | 2/2010 | Dall'Acqua et al. |
| 7,833,755 B2 | 11/2010 | Chen et al. |

| | | | |
|---|---|---|---|
| 8,153,128 B2 | 4/2012 | Bowers et al. |
| 8,198,414 B2 | 6/2012 | Cruwys et al. |
| 8,277,804 B2 | 10/2012 | Smith |
| 8,945,560 B1 | 2/2015 | Clube |
| 9,005,620 B2 | 4/2015 | Cruwys et al. |
| 9,017,678 B1 | 4/2015 | Clube |
| 9,187,562 B1 | 11/2015 | Clube |
| 9,234,034 B2 | 1/2016 | Ferlin et al. |
| 9,303,089 B2 | 4/2016 | Clube |
| 9,394,568 B2 | 7/2016 | Clube |
| 9,428,578 B2 | 8/2016 | Clube |
| 9,439,963 B2 | 9/2016 | Clube |
| 10,231,981 B2 | 3/2019 | Zhang et al. |
| 11,384,143 B2 | 7/2022 | Devalaraja et al. |
| 2001/0001663 A1 | 5/2001 | Kishimoto et al. |
| 2004/0185507 A1 | 9/2004 | Giles-Komar et al. |
| 2004/0197324 A1 | 10/2004 | Liu et al. |
| 2006/0078533 A1 | 4/2006 | Omoigui |
| 2006/0240012 A1 | 10/2006 | Sugimura et al. |
| 2006/0257407 A1 | 11/2006 | Chen et al. |
| 2006/0275294 A1 | 12/2006 | Omoigui |
| 2007/0154481 A1 | 7/2007 | Gelinas et al. |
| 2007/0178098 A1 | 8/2007 | Way et al. |
| 2007/0218063 A1 | 9/2007 | Skurkovich et al. |
| 2007/0243189 A1 | 10/2007 | Yoshizaki et al. |
| 2008/0075726 A1 | 3/2008 | Smith et al. |
| 2008/0090847 A1 | 4/2008 | Moe et al. |
| 2008/0145367 A1 | 6/2008 | Bove et al. |
| 2008/0181887 A1 | 7/2008 | Dall'Acqua et al. |
| 2008/0188401 A1 | 8/2008 | Cruwys et al. |
| 2008/0213277 A1 | 9/2008 | Sasu et al. |
| 2008/0279851 A1 | 11/2008 | Coyle et al. |

(Continued)

FOREIGN PATENT DOCUMENTS

| | | |
|---|---|---|
| AU | 2016302768 A1 | 2/2018 |
| AU | 2018214554 A1 | 9/2019 |

(Continued)

OTHER PUBLICATIONS

Van Rhee, F. et al. "Siltuximab for Multicentric Castleman's Disease: A Randomised, Double-Blind, Placebo-Controlled Trial." The Lancet Oncology, vol. 15, No. 9, Aug. 2014, pp. 966-974.

Canavesi et al., "Hepcidin and HFE protein: Iron metabolism as a target for the anemia of chronic kidney disease?", World Journal of Nephrology, Dec. 2012, vol. 1, No. 6, pp. 166-176.

Schena, "Management of patients with chronic kidney disease", Intern Emerg Med, 2011, vol. 6, No. 1, pp. S77-S83.

Saito, "Biomarker-Based Diagnosis and Treatment of Heart Failure—Interpretation of the BNP Statement of the Japanese Heart Failure Society", Journal of the Japanese Society of Internal Medicine, Mar. 2014, vol. 103, No. 3, pp. 747-752.

(Continued)

*Primary Examiner* — Elly-Gerald Stoica

(74) *Attorney, Agent, or Firm* — Elizabeth A. Dingess-Hammond

(57) ABSTRACT

The present disclosure provides methods of treating diuretic resistance by administering an IL-6 antagonist to patients who require diuresis. In typical embodiments, the patient has heart failure. Optionally, the patient has elevated urine levels of IL-6, plasma levels of IL-6, or both urine and plasma levels of IL-6.

10 Claims, 20 Drawing Sheets

Specification includes a Sequence Listing.

(56) References Cited

U.S. PATENT DOCUMENTS

| | | |
|---|---|---|
| 2008/0312172 A1 | 12/2008 | Giles-Komar et al. |
| 2009/0104187 A1 | 4/2009 | Kovacevich et al. |
| 2009/0148446 A1 | 6/2009 | Skurkovich et al. |
| 2009/0202520 A1 | 8/2009 | Lupher, Jr. et al. |
| 2009/0220500 A1 | 9/2009 | Kobara |
| 2009/0238825 A1 | 9/2009 | Kovacevich et al. |
| 2009/0239258 A1 | 9/2009 | Chen et al. |
| 2009/0263384 A1 | 10/2009 | Okada et al. |
| 2009/0269335 A1 | 10/2009 | Nakashima et al. |
| 2009/0291077 A1 | 11/2009 | Smith et al. |
| 2009/0291082 A1 | 11/2009 | Smith |
| 2009/0297535 A1 | 12/2009 | Kolkman et al. |
| 2010/0015145 A1 | 1/2010 | Sheriff et al. |
| 2010/0129354 A1 | 5/2010 | Merchiers et al. |
| 2010/0129357 A1 | 5/2010 | Garcia-Martinez et al. |
| 2010/0150829 A1 | 6/2010 | Garcia-Martinez et al. |
| 2010/0158859 A1 | 6/2010 | Smith et al. |
| 2010/0203009 A1 | 8/2010 | Weaver et al. |
| 2010/0215654 A1 | 8/2010 | Bove et al. |
| 2010/0285011 A1 | 11/2010 | Morichika et al. |
| 2011/0002936 A1 | 1/2011 | Ferlin et al. |
| 2011/0171241 A1 | 7/2011 | Dix et al. |
| 2012/0034212 A1 | 2/2012 | Bowen et al. |
| 2012/0097565 A1 | 4/2012 | Dix et al. |
| 2012/0189621 A1 | 7/2012 | Dean et al. |
| 2012/0225060 A1 | 9/2012 | Lee et al. |
| 2012/0253016 A1 | 10/2012 | Igawa et al. |
| 2012/0301462 A1 | 11/2012 | Cruwys |
| 2013/0017575 A1 | 1/2013 | Garcia-Martinez et al. |
| 2013/0224109 A1 | 8/2013 | Strrom et al. |
| 2013/0280266 A1 | 10/2013 | Rajpal et al. |
| 2014/0141013 A1 | 5/2014 | Giles-Komar et al. |
| 2014/0302058 A1 | 10/2014 | Bowen et al. |
| 2015/0125468 A1 | 5/2015 | Schmidt et al. |
| 2015/0140011 A1 | 5/2015 | Blanchetot et al. |
| 2015/0197568 A1 | 7/2015 | Cruwys et al. |
| 2015/0203574 A1 | 7/2015 | Rajpal et al. |
| 2015/0239970 A1 | 8/2015 | Bee et al. |
| 2015/0246092 A1 | 9/2015 | Wilson et al. |
| 2015/0337036 A1 | 11/2015 | Garcia-Martinez et al. |
| 2016/0017032 A1 | 1/2016 | Westerman et al. |
| 2016/0017056 A1 | 1/2016 | Clube |
| 2016/0130340 A1 | 5/2016 | Smith |
| 2016/0159896 A1 | 6/2016 | Clube |
| 2016/0168243 A1 | 6/2016 | Smith |
| 2016/0176956 A1 | 6/2016 | Cong et al. |
| 2016/0355584 A1 | 12/2016 | Wagner et al. |
| 2017/0029299 A1 | 2/2017 | Lahav et al. |
| 2017/0029499 A1 | 2/2017 | Kakkar et al. |
| 2019/0241650 A1 | 8/2019 | Devalaraja et al. |
| 2019/0248886 A1 | 8/2019 | Devalaraja et al. |
| 2020/0079846 A1 | 3/2020 | Testani et al. |
| 2021/0292405 A1 | 9/2021 | Kakkar et al. |
| 2022/0195033 A1 | 6/2022 | Testani et al. |
| 2022/0227856 A1 | 7/2022 | Devalaraja et al. |
| 2023/0090473 A1 | 3/2023 | Devalaraja et al. |

FOREIGN PATENT DOCUMENTS

| | | |
|---|---|---|
| AU | 2019268074 A1 | 12/2019 |
| CA | 2991637 A1 | 2/2017 |
| CA | 3051865 A1 | 8/2018 |
| CN | 1349410 A | 5/2002 |
| CN | 1694894 A | 11/2005 |
| CN | 101883588 A | 1/2010 |
| CN | 101641374 A | 2/2010 |
| CN | 102387814 A | 3/2012 |
| CN | 104998254 A | 10/2015 |
| CN | 108026582 A | 5/2018 |
| CN | 110913900 A | 3/2020 |
| EA | 201890185 A1 | 7/2018 |
| EP | 0399429 A1 | 11/1990 |
| EP | 0410813 B1 | 1/1996 |
| EP | 1536012 A1 | 1/2005 |
| EP | 1977763 A1 | 10/2008 |
| EP | 1715891 B1 | 4/2010 |
| EP | 3329018 A1 | 6/2018 |
| EP | 3576790 A1 | 12/2019 |
| EP | 3888752 A1 | 10/2021 |
| HK | 1249923 A1 | 11/2018 |
| IN | 201817000037 A | 3/2018 |
| IN | 201917034989 A | 8/2019 |
| JP | H10-66582 | 3/1998 |
| JP | 2005-501514 A | 1/2005 |
| JP | 2007-524602 A | 8/2007 |
| JP | 2007-528691 | 10/2007 |
| JP | 2008-538931 A | 11/2008 |
| JP | 2010-510795 A | 4/2010 |
| JP | 2012-516158 A | 7/2012 |
| JP | 2014-001216 A | 1/2014 |
| JP | 2016503397 A | 2/2016 |
| JP | 2018529756 A | 10/2018 |
| JP | 2020-506190 | 2/2020 |
| JP | 7386838 B2 | 11/2023 |
| KR | 10-2010-0028569 A | 3/2010 |
| KR | 20180058708 A | 6/2018 |
| MX | 2018000778 A | 8/2018 |
| NZ | 739392 A | 10/2019 |
| RU | 2195960 C2 | 1/2003 |
| RU | 2318829 C2 | 3/2008 |
| SG | 11201906852X A | 8/2019 |
| TW | 200900420 A | 1/2009 |
| TW | 201832780 A | 9/2018 |
| TW | I653339 B | 3/2019 |
| TW | 201928063 A | 7/2019 |
| WO | 0066151 A | 11/2000 |
| WO | WO 2003/055979 A3 | 10/2003 |
| WO | WO 2004/003019 | 1/2004 |
| WO | WO 2004/039826 A1 | 5/2004 |
| WO | WO 2004/045507 A2 | 6/2004 |
| WO | WO 2004/020633 A1 | 11/2004 |
| WO | WO 2005/028514 A1 | 3/2005 |
| WO | WO 2005/080429 A2 | 9/2005 |
| WO | WO 2006/072954 A2 | 7/2006 |
| WO | WO 2006/119115 A3 | 11/2006 |
| WO | WO 2006/122825 A2 | 11/2006 |
| WO | WO 2006/130834 A2 | 12/2006 |
| WO | WO 2007/046489 A1 | 4/2007 |
| WO | WO 2007/066082 A2 | 6/2007 |
| WO | WO 2007/106811 A2 | 9/2007 |
| WO | WO 2008/065378 A2 | 6/2008 |
| WO | WO 2008/086395 A2 | 7/2008 |
| WO | WO 2008/144763 A2 | 11/2008 |
| WO | WO 2008/156807 A2 | 12/2008 |
| WO | WO 2009/003019 A1 | 12/2008 |
| WO | WO 2009/026158 A2 | 2/2009 |
| WO | WO 2009/140348 A2 | 11/2009 |
| WO | WO 2010/065072 A1 | 6/2010 |
| WO | WO 2010/088444 A1 | 8/2010 |
| WO | WO 2011/066369 A2 | 6/2011 |
| WO | WO 2002/060919 A2 | 8/2012 |
| WO | WO 2014/066419 A2 | 5/2014 |
| WO | WO 2014/066468 A1 | 5/2014 |
| WO | WO 2014/074823 A1 | 5/2014 |
| WO | WO 2018/144773 A1 | 8/2018 |

OTHER PUBLICATIONS

Steinbicker et al., "Out of Balance-Systemic Iron Homeostasis in Iron-Related Disorders", Nutrients, Aug. 2013, vol. 5, pp. 3034-3061.

Kobara, M. et al. "Antibody Against Interleukin-6 Receptor Attenuates Left Ventricular Remodelling After Myocardial Infarction in Mice." Cardiovascular Research, vol. 87, No. 3, Aug. 1, 2010, pp. 424-430.

Barquero, N. "Siltuximab: A New Option for the Management of Castleman's Disease." Drugs of Today (Barcelona, Spain), vol. 51, No. 1, Jan. 1, 2015, pp. 21-28.

Galesloot, T. E. et al. "Iron and Hepcidin as Risk Factors in Atherosclerosis: What do the Genes Say?" BMC Genetics, vol. 16, Article 79, Jul. 11, 2015, pp. 1-12.

Liu, Y-C. et al. "Siltuximab for Multicentric Castleman Disease." Expert Review of Hematology, vol. 7, No. 5, Aug. 2014, pp. 545-557.

(56)                    References Cited

OTHER PUBLICATIONS

Actemra. "Interim Report on All-Case Surveillance of Actemra for Intravenous Infusion 80mg, 200mg, 400mg: 'Castleman's Disease'." Actemra Tocilizumab, vol. 3, ACT0442.01, Dec. 2013, pp. 1-32.

Yoshizaki, L. et al. "W2-1 Significance of Cytokine Expression Including IL-6 Castleman's Disease." Abstract, Japanese Society of Clinical Immunology Journal, vol. 35, No. 4, 2012, pp. 302a.

Keidar, S. et al. "Angiotensin II Administration to Atherosclerotic Mice Increases Macrophage Uptake of Oxidized LDL." Arteriosclerosis, Thrombosis, and Vascular Biology, vol. 21, No. 9, Sep. 2001, pp. 1464-1469.

The Japan Patent Office, Notice of Reasons for Rejection, Japanese Patent Application No. 2019-541430, Jan. 18, 2022, five pages.

Yasukawa, H. et al. "As a Progressive Factor for Heart Failure: Inflammatory Fluid Factor Myocardial Damage." Japanese Journal of Medicine and Pharmaceutical Science, 2006, vol. 55, No. 6, pp. 821-825, (with concise explanation of relevance).

Finkel, K. A. et al. "IL-6 Inhibition with MEDI5117 Decreases the Fraction of Head and Neck Cancer Stem Cells and Prevents Tumor Recurrence." Neoplasia, vol. 18, No. 5, May 2016, pp. 273-281.

"Cardiorenal Syndrome Type 4." Heart, vol. 47, Iss. 5, May 2015, pp. 551-555.

"Chapter 4: Hospitalization," United States Renal Data System, 2017 USRDS Annual Data Report, ESRD in the United States, vol. 2, 2017, pp. 321-336. May be viewed at<URL: www.usrds.org/2017/view/v204.aspx>.

Corvidia Therapeutics. "Study to Assess the Safety, Pharmacokinetics, and Pharmacodynamics of Multiple Doses of COR-001," Aug. 16, 2016, 6 pages, [Online] [Retrieved on Jan. 29, 2020] Retrieved from the internet <URL: https://clinicaltrials.gov/ct2/show/NCT02868229>.

"Third Party Email Nov. 29, 2017." Nov. 29, 2017, 1 page.

Abeywardena, M. Y. et al. "Cardiovascular Biology of Interleukin-6." Current Pharmaceutical Design, vol. 15, Iss. 15, May 1, 2009, pp. 1809-1821.

Aday, A. W. et al. "Targeting Residual Inflammatory Risk: A Shifting Paradigm for Atherosclerotic Disease." Frontiers in Cardiovascular Medicine, vol. 6, Article 16, Feb. 2019, pp. 1-12.

Ahmad, T. et al. "Charting a Roadmap for Heart Failure Biomarker Studies." JACC: Heart Failure, vol. 2, Iss. 5, Oct. 2014, pp. 477-488.

Alegre, M-L. et al. "A Non-Activitating 'Humanized' Anti-CD3 Monoclonal Antibody Retains Immunosuppressive Properties in Vivo." Transplantation, vol. 57, Iss. 1, Jun. 15, 1994, pp. 1537-1543.

Andrews, N. C. "Anemia of Inflammation: The Cytokine-Hepcidin Link." The Journal of Clinical Investigation, vol. 113, Iss. 9, May 2004, pp. 1251-1253.

Anonymous. "History of Changes for Study: NCT03926117: A Phase 2, Randomized, Double-Blind, Placebo-Controlled Trial to Evaluate Reduction in Inflammation in Patients with Advanced Chronic Renal Disease Utilizing Antibody Mediated IL-6 Inhibition (RESCUE)." ClinicalTrials.gov, Archive, Apr. 19, 2019, 4 pages, [Online] [Retrieved Sep. 15, 2021], Retrieved from the Internet <URL:https://clinicaltrials.gov/ct2/history/NCT03926117?V_1=View#StudyPageTop>.

Anonymous. "History of Changes for Study: NCT04626505: Trial to Evaluate Reduction in Inflammation in Patients with Advanced Chronic Renal Disease Utilizing Antibody Mediated IL-6 Inhibition in Japan (RESCUE-2)." ClinicalTrials.gov, Archive, Nov. 10, 2020, 5 pages, [Online] [Retrieved Sep. 15, 2021], Retrieved from the Internet <URL:https://clinicaltrials.gov/ct2/history/NCT04626505?V_1=View#StudyPageTop>.

Armour, K. L. et al. "Recombinant Human IgG Molecules Lacking Fcγ Receptor I Binding and Monocyte Triggering Activities." European Journal of Immunology, vol. 29, Iss. 8, Aug. 1999, pp. 2613-2624.

Asperti, M. et al. "High Sulfation and a High Molecular Weight are Important for Anti-Hepcidin Activity of Heparin." Frontiers in Pharmacology, vol. 6, Jan. 11, 2006, pp. 1-6.

Astrazeneca. "A Double-Blind Placebo-Controlled, Randomized Study in Arthritis Subjects to Evaluate the Safety, Tolerability, Pharmacokinetics, and Pharmacodynamics of Single Ascending Doses of MEDI5117 (anti0IL-6)." ClinicalTrials.gov, Study NCT01559103, Feb. 19, 2015, pp. 1-12.

Bárány, P. et al. "High C-Reactive Protein is a Strong Predictor of Resistance to Erythropoietin in Hemodialysis Patients." American Journal of Kidney Diseases, vol. 29, Iss. 4, Apr. 1997, pp. 565-568.

Barreto, D. V. et al. "Plasma Interleukin-6 is Independently Associated with Mortality in Both Hemodialysis and Pre-Dialysis Patients with Chronic Kidney Disease." Kidney International, vol. 77, Iss. 6, Mar. 2, 2010, pp. 550-556.

Bataille, R. et al. "Biological Effects of Anti-Interleukin-6 Murine Monoclonal Antibody in Advanced Multiple Myeloma." Blood, vol. 86, Iss. 2, Jul. 15, 1995, pp. 685-691.

Bayliss, T. J. et al. "A Humanized Anti-IL-6 Anitbody (ALD518) in Non-Small Cell Lung Cancer." Expert Opinion on Biological Therapy, vol. 11, Iss. 12, Dec. 2011, pp. 1663-1668.

Bell, S. J. et al. "Review Article: The Clinical Role of Anti-TNFα Antibody Treatment in Crohn's Disease." Alimentary Pharmacology & Therapeutics, vol. 14, Iss. 5, Apr. 30, 2000, pp. 501-514.

Bendig, M. M. "Humanization of Rodent Monoclonal Antibodies by CDR Grafting." Methods: A Companion to Methods in Enzymology, vol. 8, 1994, pp. 83-93.

Benyamin, B. et al. "Common Variants in TMPRSS6 are Associated with Iron Status and Erythrocyte Volume." Nature Genetics, vol. 41, Iss. 11, Nov. 2009, pp. 1173-1175.

Besarab, A. et al. "The Effects of Normal as Compared with Hematocrit Values in Patients with Cardiac Disease who are Receiving Hemodialysis and Epoetin." New England Journal of Medicine, vol. 339, Iss. 9, Aug. 27, 1998, pp. 584-590.

Bird Rock Bio, Inc., "Study Evaluating Gerilimzumab's Safety/Efficacy for Patients MTX or TNFα Antagonist Failed in Rheumatoid Arthritis," Jun. 10, 2016, 10 pages, [Online] [Retrieved on Nov. 25, 2019] Retrieved from the internet <URL: https://clinicaltrials.gov/ct2/show/NCT02795299>.

Blay, J-Y. et al. "Role of Interleukin-6 in the Paraneoplastic Inflammatory Syndrome Associated with Renal-Cell Carcinoma." International Journal of Cancer, vol. 72, Dec. 6, 1998, pp. 424-430.

Bonda, T. A. et al. "CCN1 Expression in Interleukin-6 Deficient Mouse Kidney in Experimental Model of Heart Failure." Folia Histochemica et Cytobiologica, vol. 51, No. 1, 2013, pp. 84-91.

Bongartz, L. G. et al. "The Severe Cardiorenal Syndrome: 'Guyton Revisited'." European Heart Journal, vol. 26, Iss. 1, Jan. 2005, pp. 11-17.

Bork, P. "Powers and Pitfalls in Sequence Analysis: The 70% Hurdle." Genome Research, vol. 10, Iss. 4, Apr. 1, 2000, pp. 398-400.

Boulanger, M. J. et al. "Hexameric Structure and Assembly of the Interleukin-6/IL-6 α-Receptor/gp 130 complex." Science, vol. 27, Jun. 2003, pp. 2101-2104.

Bowie, J. U. et al. "Deciphering the Message in Protein Sequences: Tolerance to Amino Acid Substitutions." Science, vol. 247, Mar. 16, 1990, pp. 1306-1310.

Braam, B. et al. "Cardiorenal Syndrome—Current Understanding and Future Perspectives." Nature, vol. 10, Jan. 2014, pp. 48-55.

Bradel-Tretheway, B. G. et al. "Effects of Codon-Optimization on Protein Expression by the Human Herpesvirus 6 and 7 U51 Open Reading Frame." Journal of Virological Methods, vol. 111, Iss. 2, Aug. 2003, pp. 145-156.

Brakenhoff, J. P. et al. "Development of a Human Interleukin-6 Receptor Antagonist." The Journal of Biological Chemistry, vol. 269, Iss. 1, Jan. 7, 1994, pp. 86-93.

Brakenhoff, J. P. et al. "Structure-Function Analysis of Human IL-6. Epitope Mapping of Neutralizing Monoclonal Antibodies with Amino- and Carboxyl-Terminal Deletion Mutants." The Journal of Immunology, vol. 145, Iss. 2, Jul. 15, 1990, pp. 561-568.

Brands, M. W. et al. "Interleukin 6 Knockout Prevents Angiotensim II Hypertension: Role of Renal Vasoconstriction and Janus Kinase 2/Signal Transducer and Activator of Transcription 3 Activation." Hypertension, vol. 56, Iss. 5, Nov. 2010, pp. 879-884.

(56)            References Cited

OTHER PUBLICATIONS

Brochier, J. et al. "Immunomodulating IL-6 Activity by Murine Monoclonal Antibodies." International Journal of Immunopharmacology, vol. 17, Iss. 1, Jan. 1995, pp. 41-48.
Brorson, K. et al. "Mutational Analysis of Avidity and Fine Specificity of Anti-Levan Antibodies." The Journal of Immunology, vol. 163, Iss. 12, Dec. 15, 1999, pp. 6694-6701.
Brown, M. et al. "Tolerance to Single, but not Multiple, Amino Acid Replacements in Antibody Vh CDR2." The Journal of Immunology, vol. 156, Iss. 9, May 1, 1996, pp. 3285-3291.
Brummell, D. A. et al. "Probing the Combining Site of an Anti-Carbohydrate Antibody by Saturation-Mutagenesis: Role of the Heavy-Chain CFR3 Residues." Biochemistry, vol. 32, Iss. 4, Feb. 2, 1993, pp. 1180-1187.
Burgess, W. H. et al. "Possible Dissociation of the Heparin-Binding and Mitogenic Activities of Heparin- Binding (Acidic Fibroblast) Growth Factor-1 from its Receptor-Binding Activities by Site-Directed Mutagenesis of a Single Lysine Residue." The Journal of Cell Biology, vol. 111, Nov. 1990, pp. 2129-2138.
Burks, E. A. et al. "In vitro Scanning Saturation Mutagenesis of an Antibody Binding Pocket." PNAS, vol. 94, Jan. 1997, pp. 412-417.
Calabrese, L. H. et al. "The New and Evolving Science of IL-6 in Rheumatoid Arthritis: The Contributions of IL-6 to Disease Manifestations of RA." Sanofi and Regneron Pharmaceuticals, Inc., Sep. 2015, pp. 1-16.
Caldas, C. et al. "Humanization of the Anti-CD18 Antibody 6.7: An Unexpected Effect of a Framework Residue in Binding to Antigen." Molecular Immunology, vol. 39, May 2003, pp. 941-952.
Casadevall, A. et al. "Immunoglobin Isotype Influences Affinity and Specificity." PNAS, vol. 109, Iss. 31, Jul. 31, 2012, pp. 12272-12273.
Casanovas, G. et al. "A Multi-Scale Model of Hepcidin Promoter Regulation Reveals Factors Controlling Systemic Iron Homeostasis." PLOS Computational Biology, vol. 10, Iss. 1, Jan. 2014, pp. 1-13.
Casper, C. et al. "Analysis of Inflammatory and Anemia-Related Biomarkers in a Randomized, Double-Blind, Placebo-Controlled Study of Siltuximab (anti-IL6 Monoclonal Antibody) in Patients with Multicentric Castleman Disease." Clinical Cancer Research, vol. 21, Iss. 19, Oct. 1, 2015, pp. 4294-4304.
Casset, F. et al. "A Peptide Mimetic of an Anti-CD4 Monoclonal Antibody by Rational Design." Biochemical and Biophysical Research Communications, vol. 307, Iss. 1, Jul. 2003, pp. 198-205.
Castagna, A. et al. "Hepcidin Assay in Serum by SELDI-TOF-MS and Other Approaches." Journal of Proteomics, vol. 73, Iss. 3, Jan. 3, 2010, pp. 527-536.
Casu, G. et al. "Diuretic Therapy in Heart Failure—Current Approaches." European Cardiology, vol. 10, No. 1, Jul. 2015, pp. 42-47.
Chambers, J. C. et al. "Genome-Wide Association Study Identifies Variants in TMPRSS6 Associated with Hemoglobin Levels." Nature Genetics, vol. 41, Iss. 11, Nov. 2009, pp. 1170-1172.
Chambers, J. C. et al. "Genome-Wide Association Study Identifies Variants in TMPRSS6 Associated with Hemoglobin Levels." Supplementary Online Material, Nature Genetics, 2009, pp. 1-12.
Chaouat, A. et al. "Role for Interleukin-6 in COPD-Related Pulmonary Hypertension." Chest, vol. 136, Iss. 3, Sep. 2009, pp. 678-687.
Chen, Y. et al. "Selection and Analysis of an Optimized Anti-VEGF Antibody: Crystal Structure of an Affinity-Matured Fab in Complex with Antigen." Journal of Molecular Biology, vol. 293, Iss. 4, Nov. 5, 1999, pp. 865-881.
Chien, N. C. et al. "Significant Structural and Functional Change of an Antigen-Binding Site by a Distant Amino Acid Substitution: Proposal of a Structural Mechanism." Proceedings of the National Academy of Sciences, vol. 8, Jul. 1989, pp. 5532-5536.
Chonchol, M. "Neutrophil Dysfunctional and Infection Risk in End-Stage Renal Disease." Seminars in Dialysis, vol. 19, Iss. 4, Jul.-Aug. 2006, pp. 291-296.

Choy, E. "Clinical Experience with Inhibition of Interleukin-6." Rheumatic Disease Clinics of North America, vol. 30, Apr. 30, 2004, pp. 405-415.
Clementi, A. et al. "Cardiorenal Syndrome Type 4: A Review." CardioRenal Medicine, vol. 3, Iss. 1, Apr. 2013, pp. 63-70.
clinicaltrials.gov. "A Study of Patients with Chronic Kidney Disease to Assess the Safety of a Single Dose of COR-001 (COR-001-SC1)." ClinicalTrials.Gov, Apr. 24, 2017, 8 pages, [Online], [Retrieved Aug. 27, 2019], Retrieved from the internet <URL:https://clinicaltrials.gov/ct2/show/NCT03126318>.
Colman, P. M. "Effects of Amino Acid Sequence Changes on Antibody-Antigen Interactions." Research in Immunology, vol. 145, Jan. 1994, pp. 33-36.
Colombo, P. C. et al. "Inflammatory Activiation: Cardiac, Renal, and Cardio-Renal Interactions in Patients with the Cardiorenal Syndrome." Heart Failure Reviews, vol. 17, Iss. 2, Mar. 2012, pp. 177-190.
Constantinou, A. et al. "Site-Specific Polysialylation of an Antitumor Single-Chain Fv Fragment." Bioconjugate Chemistry, vol. 20, Iss. 5, May 2009, pp. 924-931.
Coyne, D. W. et al. "Ferric Gluconate is Highly Efficacious in Anemic Hemodialysis Patients with High Serum Ferritin and Low Transferrin Saturation: Results of the Dialysis Patients' Response to IV Iron with Elevated Ferritin (DRIVE) Study." Journal of the American Society of Nephrology, vol. 18, Iss. 3, Mar. 2007, pp. 975-984.
Dall'acqua, W. F. et al. "Increasing the Affinity of a Human IgG1 for the Neonatal Fc Receptor: Biological Consequences." The Journal of Immunology, vol. 169, Iss. 9, Nov. 1, 2002, pp. 5171-5180.
Dall'acqua, W. F. et al. "Properties of Human IgG1s Engineered for Enhanced Binding to the Neonatal Fc Receptor (FcRn)." The Journal of Biological Chemistry, vol. 281, Iss. 33, Aug. 18, 2006, pp. 23514-23524.
Damman, K. et al. "Worsening Renal Function and Prognosis in Heart Failure: Systematic Review and Meta-Analysis." Journal of Cardiac Failure, vol. 13, Iss. 8, Oct. 2007, pp. 599-608.
Datta-Mannan, A. et al. "Humanized IgG1 Variants with Differential Binding Properties to the Neonatal Fc Receptor: Relationships to Pharmacokinetics in Mice and Primates." Drug Metabolism and Disposition, vol. 35, Iss. 1, Jan. 2007, pp. 86-94.
Datta-Mannan, A. et al. "Monoclonal Antibody Clearance: Impact of Modulating the Interaction of IgG with the Neonatal Fc Receptor." Journal of Biological Chemistry, vol. 282, Iss. 3, Jan. 19, 2007, pp. 1709-1717.
Davies, J. et al. "Affinity Improvement of Single Antibody VH Domains: Residues in all Three Hypervariable Regions Affect Antigen Binding." Immunotechnology, vol. 2, Iss. 3, Sep. 1996, pp. 169-179.
Davis, C. C. et al. "Clinical Development of Siltuximab." Current Oncology Reports, vol. 17, Issue 29, Jul. 2015, pp. 1-9.
De Francisco, A. L. M. et al. "Inflammation and its Impact on Anaemia in Chronic Kidney Disease: From Haemoglobin Variability to Hyporesponsiveness." NDT Plus, vol. 2, Iss. 1, Jan. 1, 2009, pp. i18-i26.
De Pascalis, R. et al. "Grafting of 'Abbreviated' Complementarity-Determining Regions Containing Specificity-Determining Residue Essential for Ligand Contact to Engineer a Less Immunogenic Humanized Monoclonal Antibody." The Journal of Immunology, vol. 169, Iss. 6, Sep. 15, 2002, pp. 3076-3084.
Deisseroth, A. et al. "FDA Approval: Siltuximab for the Treatment of Patients with Multicentric Castleman Disease." Clinical Cancer Research, vol. 21, Iss. 5, Mar. 1, 2015, pp. 950-954.
Demant, A. W. et al. "Heart Failure and Malignant Ventricular Tachyarrhythmias due to Hereditary Hemochromatosis with Iron Overload Cardiomyopathy." Clinical Research in Cardiology, vol. 96, Aug. 20, 2007, pp. 900-903.
Desgeorges, A. et al. "Concentrations and Origins of Soluble Interleukin 6 Receptor-α in Serum and Synovial Fluid." The Journal of Rheumatology, vol. 24, Iss. 8, Jul. 31, 1997, pp. 1510-1516.
Duncan, A. R. et al. "Localizaiton of the Binding Site for the Human High-Affinity Fc Receptor on IgC." Nature, vol. 332, Apr. 7, 1988, pp. 563-564.

(56)                References Cited

OTHER PUBLICATIONS

Eddahibi, S. et al. "Interleukin-6 Gene Polymorphism Confers Susceptibility to Pulmonary Hypertension in Chronic Ostructive Pulmonary Disease." Proceedings of the American Thoracic Society, vol. 3, Iss. 6, Aug. 1, 2006, pp. 475-476.

Eickhoff, P. et al. "Determinants of Systemic Vascular Function in Patients with Stable Chronic Obstructive Pulmonary Disease." American Journal of Respiratory and Critical Care Medicine, vol. 178, Iss. 2, Dec. 15, 2008, pp. 1211-1218.

Elewa, U. et al. "Cardiovascular Risk Biomarkers in CKD: The Inflammation Link and the Road Less Traveled." International Urology and Nephrology, vol. 44, Sep. 11, 2012, pp. 1731-1744.

Ellison, D. H. "Chapter 30: The Physiological Basis of Diuretic Drug Action and Synergism." Principles of Medical Biology, vol. 8B: Molecular and Cellular Pharmacology, 1997, pp. 577-599.

Emilie, D. et al. "Administration of an Anti-Interleukin-6 Monoclonal Antibody to Patients with Acquired Immunodeficiency Syndrome and Lymphome: Effect on Lymphoma Growth and on B Clinical Symptoms." Blood, vol. 84, Iss. 8, Oct. 15, 1994, pp. 2472-2479.

Ernst, M. et al. "Acquiring Signalling Specificity from the Cytokine Receptor GP130." Trends in Genetics, vol. 20, Iss. 1, Jan. 2004, pp. 23-32.

Everett, B. M. et al. "Anti-Inflammatory Therapy with Canakinumab for the Prevention of Hospitalization for Heart Failure." Circulation, vol. 139, Iss. 10, Mar. 5, 2019, pp. 1289-1299.

Fagnani, R. et al. "Altered Pharmacokinetic and Tumour Localization Properties of Fab' Fragments of a Murine Monoclonal Anti-CEA Antibody by Covalent Modification with Low Molecular Weight Dextran." Nuclear Medicine Communications, vol. 16, 1995, pp. 362-369.

Fasshauer, M. et al. "Interleukin (IL)-6 mRNA Expression is Stimulated by Insulin, Isoproterenol, Tumour Necrosis Factor Alpha, Growth Hormone, and IL-6 in 3T3-L1 Adipocytes." Hormone and Metabolic Research, vol. 35, Iss. 3, Mar. 2003, pp. 147-152.

Finberg, K. E. et al. "Mutations in TMPRSS6 Cause Iron-Refractory Iron Deficiency Anemia (IRIDA)." Nature Genetics, vol. 40, Iss. 5, May 2008, pp. 569-571.

Finch, D. K. et al. "Whole-Molecule Anitbody Engineering: Generation of a High-Affinity Anti-IL-6 Antibody with Extended Pharmacokinetics." Journal of Molecular Biology, vol. 411, Iss. 4, Aug. 26, 2011, pp. 791-807.

Fishbane, S. et al. "Mechanism of Increased Mortality Risk with Erythropoietin Treatment to Higher Hemoglobin Targets." Clinical Journal of American Society of Nephrology, vol. 2, Iss. 6, Nov. 2007, pp. 1274-1282.

Fontes, J. A. et al. "The Varying Faces of IL-6: From Cardiac Protection to Cardiac Failure." Cytokine, vol. 74, No. 1, Jul. 2015, pp. 62-68.

Fulciniti, M. et al. "A High-Affinity Fully Human Anti-IL-6 mAb, 1339, for the Treatment of Multiple Myeloma." Cancer Therapy: Preclinical, vol. 15, Iss. 23, Dec. 1, 2009, pp. 7144-7152.

Fung, E. et al. "Manipulation of the Hepcidin Pathway for Therapeutic Purposes." Haematologica, vol. 98, Iss. 11, Nov. 2013, pp. 1667-1676.

Gabriel, A. S. et al. "IL-6 Levels in Acute and Post Myocardial Infarction: Their Relation to CRP Levels, Infarction Size, Left Ventricular Systolic Function, and Heart Failure." European Journal of Internal Medicine, vol. 15, Iss. 8, Dec. 2004, pp. 523-528.

Ganz, T. "Hepcidin and Iron Regulation, 10 Years Later." Blood, vol. 117, Iss. 17, Apr. 28, 2011, pp. 4425-4433.

Ganz, T. et al. "Iron Homeostasis in Host Defence and Inflammation. " vol. 15, Aug. 2015, pp. 500-510.

Ghetie, V. et al. "Increasing the Serum Persistence of an IgG Fragment by Random Mutagenesis." Nature Biotechnology, vol. 15, Jul. 1997, pp. 637-640.

Giusti, A. M. et al. "Somatic Diversification of S107 from an Antiphosphocholine to an Anti-DNA Autoantibody is Due to a Single Base Change in its Heavy Chain Variable Region." Proceedings of the National Academy of Sciences, vol. 84, Iss. 9, May 1987, pp. 2926-2930.

Golembeski, S. M. et al. "Interleukin-6 Causes Mild Pulmonary Hypertension and Augments Hypoxia-Induced Pulmonary Hypertension in Mice." Chest, vol. 128, Iss. 6, Dec. 2005, pp. 572S-573S.

Groenewegen, K. H. et al. "Longitudinal Follow-Up of Systemic Inflammation After Acute Exacerbations of COPD." Respiratory Medicine, vol. 101, Iss. 11, Nov. 2007, pp. 2409-2415.

Guillen, C. et al. "The Interleukin-6/Soluble Interleukin-6 Receptor System Induces Parathyroid Hormone-Related Protein in Human Osteoblastic Cells." Calcified Tissue International, vol. 75, Apr. 29, 2004, pp. 153-159.

Gussow, D. et al. "Humanization of Monoclonal Antibodies." Methods in Enyzymology, vol. 203, Nov. 1, 1991, pp. 99-121.

Haddad, E. et al. "Treatment of B-Lymphoproliferative Disorder with a Monoclonal Anti-Interleukin-6 Antibody in 12 Patients: a Multicenter Phase 1-2 Clinical Trial." Blood, vol. 97, Iss. 6, Mar. 15, 2001, pp. 1590-1597.

Hanberg, J. S. et al. "Hypochloremia and Diuretic Resistance in Heart Failure Mechanistic Insights." Circulation: Heart Failure, vol. 9, Iss. 8, Aug. 2016, pp. 1-12.

Hanberg, J. S. et al. "Inflammation and Cardio-Renal Interactions in Heart Failure: A Potential Role for Interleukin-6." European Journal of Heart Failure, vol. 20, Iss. 5, May 2018, pp. 933-934.

Hanberg, J. S. et al. Supplementary Material. "Inflammation and Cardio-Renal Interactions in Heart Failure: A Potential Role for Interleukin-6." European Journal of Heart Failure, vol. 20, Iss. 5, May 2018, pp. 1-4.

Harrison, S. C. et al. "Interleukin-6 Receptor Pathways in Abdominal Aortic Aneurysm." European Heart Journal, vol. 34, No. 48, Dec. 21, 2013, pp. 3707-3716.

Hashizume, M. et al. "Tocilizumab, a Humanized Anti-Interleukin-6 Receptor Antibody, Improved Anemia in Monkey Arthritis by Suppressing IL-6-Induced Hepcidin Production." Rheumatology International, vol. 30, Iss. 7, May 2010, pp. 917-923.

Heinrich, P. C. et al. "Principles of Interleukin (IL)-6-Type Cytokine Signalling and its Regulation." Biochemical Journal, vol. 374, Iss. 1, Aug. 2003, pp. 1-20.

Held, C. et al. "Inflammatory Biomarkers Interleukin-6 and C-Reactive Protein and Outcomes in Stable Coronary Heart Disease: Experiences from the STABILITY (Stabilization of Atherosclerotic Plaque by Initiation of Darapladib Therapy) Trial." Journal of the American Heart Association, vol. 6, Iss. 10, Oct. 11, 2017, pp. 1-35.

Hentze, M. W. et al. "Balancing Acts: Molecular Control of Mammalian Iron Metabolism." Cell, vol. 117, Apr. 30, 2014, pp. 285-297.

Hentze, M. W. et al. "Two to Tango: Regulation of Mammalian Iron Metabolism." Cell, vol. 142, Jul. 9, 2010, pp. 24-38.

Heymans, S. et al. "Inflammation as a Therapeutic Target in Heart Failure? A Scientific Statement from the Translational Research Committee of the Heart Failure Association of the European Society of Cardiology." European Journal of Heart Failure, vol. 11, 2009, pp. 119-129.

Hibi, M. et al. "Molecular Cloning and Expression of an IL-6 Signal Transducer, gp130." Cell, vol. 63, Iss. 6, Dec. 21, 1990, pp. 1149-1157.

Hinton, P. R. et al. "An Engineered Human IgG1 Antibody with Longer Serum Half-Life." The Journal of Immunology, vol. 176, Iss. 1, Jan. 1, 2006, pp. 346-356.

Hinton, P. R. et al. "Engineered Human IgG Antibodies with Longer Serum Half-Lives in Primates." The Journal of Biological Chemistry, vol. 279, Iss. 8, Feb. 20, 2004, pp. 6213-6216.

Hirano, T. et al. "Complimentary DNA for a Novel Human Interleukin (BSF-2) that Induces B Lymphocytes to Produce Immunoglobulin." Nature, vol. 324, Nov. 6, 1986, pp. 73-76.

Hirata, Y. et al. "Characterization of IL-6 Receptor Expression by Monoclonal and Polyclonal Antibodies." The Journal of Immunology, vol. 143, Iss. 9, Nov. 1, 1989, pp. 2900-2906.

Holm, P. et al. "Functional Mapping and Single Chain Construction of the Anti-Cytokeratin 8 Monoclonal Antibody TS1." Molecular Immunology, vol. 44, Iss. 6, Feb. 2007, pp. 1075-1084.

(56) References Cited

OTHER PUBLICATIONS

Holt, L. J. et al. "Doman Antibodies: Proteins for Therapy." TRENDS in Biotechnology, vol. 21, Iss. 11, Nov. 2003, pp. 484-490.

Hou, H. et al. "Association of Interleukin-6 Gene Polymorphism with Coronary Artery Disease: An Updated Systematic Review and Cumulative Meta-Analysis." Inflammation Research, vol. 64, Iss. 9, Sep. 2015, pp. 707-720.

Huizinga, T. W. J. et al. "Sarilumab, a Fully Human Monoclonal Antibody Against IL-6Rα in Patients with Rheumatoid Arthritis and an Inadequate Response to Methotrexate: Efficacy and Safety Results from the Randomised SARIL-RA-MOBILITY Part A Trial." Annals of Rheumatic Diseases, vol. 73, Iss. 9, Jul. 31, 2014, pp. 1626-1634.

Hung, A. M. et al. "IL-1β Receptor Antagonist Reduces Inflammation in Hemodialysis Patients." Journal of the American Society of Nephrology, vol. 22, Iss. 3, Mar. 2011, pp. 437-442.

Hutchins, J. T. "Improved Biodistribution, Tumor Targeting, and Reduced Immunogenicity in Mice with a γ4 Variant of Campath-1H." PNAS, vol. 92, Dec. 1995, pp. 11980-11984.

Idusogie, E. E. et al. "Engineered Antibodies with Increased Activity to Recruit Complement." The Journal of Immunology, vol. 166, Iss. 4, Feb. 15, 2001, pp. 2571-2575.

Idusogie, E. E. et al. "Mapping of the C1q Binding Site on Rituxan, a Chimeric Antibody with a Human IgG1 Fc." The Journal of Immunology, vol. 164, Iss. 8, Apr. 15, 2000, pp. 4178-4184.

Illei, G. G. et al. "Tocilizumab in Systemic Lupus Erythematosus: Data on Safety, Preliminary Efficacy, and Impact on Circulating Plasma Cells from an Open-Label Phase I Dosage-Escalation Study." Arthritis and Rheumatism, vol. 62, Iss. 2, Feb. 2010, pp. 542-552.

Illman, J. et al. "Are Inflammatory Cytokines the Common Link Between Cancer-Associated Cachexia and Depression." The Journal of Supportive Oncology, vol. 3, Iss. 1, Jan./Feb. 2005, pp. 37-50.

Isaacs, J. D. et al. "Effect of Tocilizumab on Haematological Markers Implicates Interleukin-6 Signalling in the Anaemia of Rheumatoid Arthritis." Arthritis Research & Therapy, vol. 15, Dec. 2013, pp. 1-6.

Jang, Y.-J. et al. "The Structural Basis for DNA Binding by an Anti-DNA Autoantibody." Molecular Immunology, vol. 35, Dec. 15, 1998, pp. 1207-1217.

Jefferis, R. et al. "Interaction Sites on Human IgG-Fc for FcγR: Current Models." Immunology Letters, vol. 82, Iss. 1-2, Jun. 3, 2002, pp. 57-65.

Jefferis, R. et al. "Modulation of FcγR and Human Complement Activation by IgG3-Core Oligosaccharide Interactions." Immunology Letters, vol. 54, Iss. 2-3, Dec. 1996, pp. 101-104.

Jefferis, R. et al. "Recognition Sites on Human IgG for Fcγ Receptors: The Role of Glycosylation." Immunology Letters, vol. 44, Iss. 2-3, Jan. 2, 1995, pp. 111-117.

Johnston, R. A. et al. "Role of Interleukin-6 in Murine Airway Responses to Ozone." American Journal of Physiology, vol. 288, Iss. 2, Feb. 1, 2005, pp. L390-L397.

Jones, S. A. et al. "The Soluble Interleukin 6 Receptor: Mechanisms of Production and Implications in Disease." The FASEB Journal, vol. 15, Iss. 1, Jan. 1, 2001, pp. 43-58.

Jones, S. A. et al. "Therapeutic Strategies for the Clinical Blockade of IL-6/gp130 Signaling." The Journal of Clinical Investigation, vol. 121, Iss. 9, Sep. 2011, pp. 3375-3383.

Julian, M. C. et al. "Efficient Affinity Maturation of Antibody Variable Domains Requires Co-Selection of Compensatory Mutations to Maintain Thermodynamic Stability." Scientific Reports, Mar. 28, 2017, pp. 1-13.

Kakkar, R. et al. "Effects of Ziltivekimab (ZILTI), a Novel Anti-Interleukin-6 Monoclonal Antibody, on Markers of Inflammation and Cardiovascular Risk in Patients With Chronic Kidney Disease on Hemodialysis." Circulation, vol. 140, Nov. 19, 2019.

Kalai, M. et al. "Analysis of the Human Interleukin-6/Human Interleukin-6 Receptor Binding Interface at the Amino Acid Level: Proposed Mechanism of Interaction." Blood, vol. 89, Iss. 4, Feb. 15, 1997, pp. 1319-1333.

Kalai, M. et al. "Analysis of the Mechanism of Action of Anti-Human Interleukin-6 and Anti-Human Interleukin-6 Receptor-Neutralising Monoclonal Antibodies." European Journal of Biochemistry, vol. 249, Nov. 1997, pp. 690-700.

Kalai, M. et al. "Participation of two Ser-Ser-Phe-Tyr Repeats in Interleukin-6 (IL-6)-Binding Sites of the Human IL-6 Receptor." European Journal of Biochemistry, vol. 238, Iss. 3, Jun. 1996, pp. 714-723.

Kalantar-Zadeh, K. et al. "Effect of Malnutrition-Inflammation Complex Syndrome on EPO Hyporesponsiveness in Maintenance Hemodialysis Patients." American Journal of Kidney Diseases, vol. 42, Iss. 4, Oct. 2003, pp. 761-773.

Kalantar-Zadeh, K. et al. "Time-Dependent Associations Between Iron and Mortality in Hemodialysis Patients." Journal of the American Society of Nephrology, vol. 16, Iss. 10, Oct. 2005, pp. 3070-3080.

Kaminska, J. et al. "IL 6 but not TNF is Linked to Coronary Artery Calcification in Patients with Chronic Kidney Disease." Cytokine, vol. 120, Aug. 2019, pp. 9-14.

Kanda, J. et al. "Reversible Cardiomyopathy Associated with Multicentric Castleman Disease: Successful Treatment with Tocilizumab, an Anti-Interleukin 6 Receptor Antibody." International Journal of Hematology, vol. 85, No. 3, Apr. 2007, pp. 207-211.

Kawano, M. et al. "Autocrine Generation and Requirement of BSF-2/IL-6 for Human Multiple Myelomas." Nature, vol. 332, Mar. 3, 1988, pp. 83-85.

Keller, E. T. et al. "Molecular and Cellular Biology of Interleukin-6 and its Receptor." Frontiers in Bioscience, vol. 1, Nov. 30, 1996, pp. 340-357.

Kharagjitsingh, A. V. et al. "Incidence of Recombinant Erythropoietin (EPO) Hyporesponse, EPO-Associated Antibodies, and Pure Red Cell Aplasia in Dialysis Patients." Kidney International, vol. 68, Iss. 3, Sep. 2005, pp. 1215-1222.

Kielar, M. L. et al. "Maladaptive Role of IL-6 in Ischemic Acute Renal Failure." Journal of the American Society of Nephrology, vol. 16, Iss. 11, Nov. 2005, pp. 3315-3325.

Kilpatrick, R. D. et al. "Greater Epoetin Alfa Responsiveness is Associated with Improved Survival in Hemodialysis Patients." Clinical Journal of the American Society of Nephrology, vol. 3, Iss. 4, Jul. 2008, pp. 1077-1083.

Kim, G. W. et al. "IL-6 Inhibitors for Treatment of Rheumatoid Arthritis: Past, Present, and Future." Archives of Pharmacal Research, vol. 38, Iss. 5, May 2015, pp. 575-584.

Kim, G. W. et al. "Table 2: Tocilizumab and Investigational IL-6 Inhibitors." Springer, May 2015, p. 580.

Kim, H-R. et al. "Serum Pro-Hepcidin Could Reflect Disease Activity in Patients with Rheumatoid Arthritis." J Korean Med Sci., vol. 25, Iss. 3, Mar. 2010, pp. 348-352.

Kishimoto, T. "Interleukin-6: Discovery of a Pleiotropic Cytokine." Arthritis Research & Therapy, vol. 8, Iss. 2, Jul. 28, 2006, pp. 1-6.

Kishimoto, T. "The Biology of Interleukin-6." Blood, vol. 74, Iss. 1, Jul. 1989, pp. 1-10.

Klouche, M. et al. "Novel Path to Activation of Vascular Smooth Muscle Cells: Up-Regulation of gp130 Creates an Autocrine Activation Loop by IL-6 and its Soluble Receptor." The Journal of Immunology, vol. 163, Iss. 8, Oct. 15, 1999, pp. 4583-4589.

Kobayashi, H. et al. "Tryptophan H33 Plays an Important Role in Pyrimidine (6-4) Pyrimidone Photoproduct Binding by a High-Affinity Antibody." Protein Engineering, vol. 12, Iss. 10, Oct. 1999, pp. 879-884.

Kovac, S. et al. "Anti-Hemojuvelin Antibody Corrects Anemia Caused by Inappropriately High Hepcidin Levels." Haematologica, vol. 101, Iss. 5, May 2016, pp. e173-e176.

Kumar, S. et al. "Molecular Cloning and Expression of the Fabs of Human Autoantibodies in Eschérichia coli." The Journal of Biological Chemistry, vol. 275, Nov. 10, 2000, pp. 35129-35136.

Lang, J. E. et al. "Effect of Obesity on Pulmonary Inflammation Induced by Acute Ozone Exposure: Role of Interleukin-6." American Journal of Physiology, vol. 294, May 1, 2008, pp. L1013-L1020.

(56)                References Cited

OTHER PUBLICATIONS

Lazar, E. et al. "Transforming Growth Factor α: Mutation of Aspartic Acid 47 and Leucine 48 Results in Different Biological Activities." Molecular and Cellular Biology, vol. 8, Iss. 3, Mar. 1988, pp. 1247-1252.

Levey, A. S. et al. "A New Equation to Estimate Glomerular Filtration Rate." Annals of Internal Medicine, vol. 150, Iss. 9, May 5, 2009, pp. 604-612.

Li, K. et al. "Interleukin-6 Stimulates Epithelial Sodium Channels in Mouse Cortical Collecting Duct Cells." American Journal of Physiology: Regulatory, Integrative and Comparative Physiology, vol. 299, Iss. 2, Aug. 2010, pp. R590-R595.

Lindmark, E. et al. "Relationship Between Interleukin 6 and Mortality in Patients with Unstable Coronary Artery Disease: Effects of an Early Invasive or Noninvasive Strategy." JAMA, vol. 286, Iss. 17, Nov. 7, 2001, pp. 2107-2113.

Lu, Z. Y. "High Amounts of Circulating Interleukin (IL)-6 in the Form of Monomeric Immune Complexes During Anti-IL-6 Therapy. Towards a New Methodology for Measuring Overall Cytokine Production in Human in Vivo." European Journal of Immunology, vol. 22, Iss. 11, Nov. 1992, pp. 2819-2824.

Lu, Z. Y. et al. "Measurement of Whole Body Interleukin-6 (IL-6) Production: Prediction of the Efficacy of Anti-IL-6 Treatments." Blood, vol. 86, Iss. 8, Oct. 15, 1995, pp. 3123-3131.

Lu, Z-R. et al. "Polymerizable Fab' Antibody Fragments for Targeting of Anticancer Drugs." Nature Biotechnology, vol. 17, 1999, pp. 1101-1104.

Lund, J. et al. "Human FcγRI and FcγRII Interact with Distinct but Overlapping Sites on Human IgG[1]." The Journal of Immunology, vol. 147, Iss. 5, Oct. 15, 1991, pp. 2657-2662.

Lund, J. et al. "Multiple Binding Sites on the Ch2 Domain of IgG for Mouse FcγRII." Molecular Immunology, vol. 29, Iss. 1, Jan. 1992, pp. 53-59.

Lund, J. et al. "Multiple Interactions of IgG with its Core Oligosaccharide can Modulate Recognition by Complement and Human Fcγ Receptor I and Influence the Synthesis of its Oligosaccharide Chains." The Journal of Immunology, vol. 157, Iss. 11, Dec. 1, 1996, pp. 4963-4969.

Lund, J. et al. "Oligosaccharide-Protein Interactions in IgG can Modulate Recognition by Fcγ Receptors." The FASEB Journal, vol. 9, Iss. 1, Jan. 1995, pp. 115-119.

Maccallum, R. M. et al. "Antibody-Antigen Interactions: Contact Analysis and Binding Site Topography." Journal of Molecular Biology, vol. 262, Iss. 5, Oct. 11, 1996, pp. 732-745.

Macdougall, I. C. et al. "Hyporesponsiveness to Erythropoietic Therapy Due to Chronic Inflammation." European Journal of Clinical Investigation, vol. 35, Iss. 3, Dec. 2005, pp. 32-35.

Mariuzza, R. A. et al. "The Structural Basis of Antigen-Antibody Recognition." Annual Review of Biophysics and Biophysical Chemistry, vol. 16, Jun. 1987, pp. 139-159.

Markousis-Mavrogenis, G. et al. "The Clinical Significance of Interleukin-6 in Heart Failure: Results from the BIOSTAT-CHF Study." European Journal of Heart Failure, vol. 21, Iss. 8, Aug. 2019, pp. 965-973.

Marz, P. et al. "Sympathetic Neurons can Produce and Respond to Interleukin 6." Proceedings of the National Academy of Sciences, vol. 95, Iss. 6, Mar. 17, 1998, pp. 3251-3256.

Massie, B. M. et al. "Rolofylline, an Adenosine A1-Receptor Antagonist, in Acute Heart Failure." The New England Journal of Medicine, vol. 363, Oct. 7, 2010, pp. 1419-1428.

Mateo, C. et al. "Humanization of a Mouse Monoclonal Antibody that Blocks the Epidermal Growth Factor Receptor: Recovery of Antagonistic Activity." Immunotechnology, vol. 3, Mar. 1997, pp. 71-81.

Melmed, G. Y. et al., "Certolizumab Pegol," Nature Reviews Drug Discovery, vol. 7, Aug. 2008, pp. 641-642.

Menziani, M. C. et al. "Theoretical Investigation of IL-6 Multiprotein Receptor Assembly." Proteins: Structure, Function, and Genetics, vol. 29, Dec. 7, 1998, pp. 528-544.

Mihara, M. et al. "The Therapy of Autoimmune Diseases by Anti-Interleukin-6 Receptor Antibody." Expert Opinion on Biological Therapy, vol. 5, Iss. 5, Nov. 24, 2005, pp. 683-690.

Mishra, A. K. et al. "Insights into the Structural Basis of Antibody Maturation from Next-Generation Sequencing." Frontiers in Immunology, vol. 9, Feb. 1, 2018, pp. 1-10.

Modur, V. et al. "Retrograde Inflammatory Signaling from Neutrophils to Enothelial Cells by Soluble Interleukin-6 Receptor Alpha." The Journal of Clinical Investigation, Dec. 1, 1997, pp. 2752-2756.

Montero-Julian, F. A. et al. "Pharmacokinetic Study of Anti-Interleukin-6 (IL-6) Therapy with Monoclonal Antibodies: Enhancement of IL-6 Clearance by Cocktails of Anti-IL-6 Antibodies." Blood, vol. 85, Feb. 15, 1995, pp. 917-924.

Moshage, H. "Cytokines and the Hepatic Acute Phase Response." Journal of Pathology, vol. 181, Iss. 3, Mar. 1997, pp. 257-266.

Muller, J. et al. "Interleukin-6-Dependent Phenotypic Modulation of Cardiac Fibroblasts after Acute Myocardial Infarction." Abstract, Basic Research in Cardiology, vol. 109, Iss. 6, Nov. 2014, pp. 1.

Murakami, M. et al. "Inducible Expression of Glial Fibrillary Acidic Protein in HT-1080 Human Fibrosarcoma Cells." Cell Growth & Differentiation, vol. 7, Dec. 1996, pp. 1697-1703.

Nai, A. et al. "Limiting Hepatic Bmp-Smad Signaling by Matriptase-2 is Required for Erythropoietin-Mediated Hepcidin Suppression in Mice." Blood, vol. 127, Iss. 19, May 12, 2016.

Nai, A. et al. "TMPRSS6 rs855791 Modulates Hepcidin Transcription in Vitro and Serum Hepcidin Levels in Normal Individuals." Blood, vol. 118, Iss. 16, Oct. 20, 2011, pp. 4459-4462.

Nakamura, I. et al. "Blockade of Interleukin 6 Signaling Induces Marked Neutropenia in Patients with Rheumatoid Arthritis." The Journal of Rheumatology, vol. 36, Iss. 2, Feb. 2009, pp. 459.

Nechemia-Arbely, Y. et al. "IL-6/IL-6R Axis Plays a Critical Role in Acute Kidney Injury." Journal of the American Society of Nephrology, vol. 19, Iss. 6, Jun. 2008, pp. 1106-1115.

Nguyen, A. et al. "The Pharmacokinetics of an Albumin-Binding Fab (AB. Fab) can be Modulated as a Function of Affinity for Albumin." Protein Engineering, Design & Selection, vol. 19, 2006, pp. 291-297.

Nishimoto, N. et al. "Inhibition of IL-6 for the Treatment of Inflammatory Diseases." Current Opinion in Pharmacology, vol. 4, Iss. 4, Aug. 2004, pp. 386-391.

Nowak, K. L. et al. "A Phase 1 Randomized, Double-Blind, Placebo-Controlled, Cohort Dose-Escalation Study of a Human Monoclonal Antibody to IL-6 in Patients with Chronic Kidney Disease." Kidney Week 2019, Washington, DC, Nov. 5-10, 2019, 1 page.

O'Connor, C. M. et al. "The PROTECT In-Hospital Risk Model: 7-Day Outcome in Patients Hospitalized with Acute Heart Failure and Renal Dysfunction." European Journal of Heart Medicine, vol. 14, 2012, pp. 605-612.

Oh, J-W. et al. "CXC Chemokine Receptor 4 Expression and Function in Human Astroglioma Cells." The Journal of Immunology, vol. 166, Iss. 4, Feb. 15, 2001, pp. 2695-2704.

Palin, K. et al. "Age-Impaired Fluid Homeostasis Depends on the Balance of IL-6/IGF-I in the Rat Supraoptic Nuclei." Neurobiology of Aging, vol. 30, Iss. 10, Oct. 2009, pp. 1677-1692.

Panichi, V. et al. "C Reactive Protein in Patients with Chronic Renal Diseases." Renal Failure, vol. 23, No. 3-4, May 1, 2001, pp. 551-562.

Panka, D. J. et al. "Variable Region Framework Differences Result in Decreased or Increased Affinity of Variant Anti-Digoxin Antibodies." PNAS, vol. 85, May 1988, pp. 3080-3084.

Patel, N. S. A. et al. "Endogenous Interleukin-6 Enhances the Renal Injury Dysfunction, and Inflammation Caused by Ischemia/ Reperfusion." The Journal of Pharmacology and Experimental Therapeutics, vol. 312, Iss. 3, Mar. 2005, pp. 1170-1178.

Paul, W. E. "Fundamental Immunology." 3rd Edition, Raven Press, New York, Nov. 1, 1993, pp. 292-295.

PCT International Search Report and Written Opinion, PCT Application No. PCT/US2019/012430, May 3, 2019, 14 pages.

PCT International Search Report and Written Opinion, PCT Application No. PCT/US16/044528, Oct. 14, 2016, 15 pages.

PCT International Search Report and Written Opinion, PCT Application No. PCT/US2018/016508, Apr. 24, 2018, 14 pages.

(56)          References Cited

OTHER PUBLICATIONS

Pecoits-Filho, R. et al. "Update on Interleukin-6 and its Role in Chronic Renal Failure." Nephrology Dialysis Transplantation, vol. 18, Iss. 6, Jun. 2003, pp. 1042-1045.

Perera, W. R. et al. "Inflammatory Changes, Recovery and Recurrence at COPD Exacerbation." European Respiratory Journal, vol. 29, Iss. 3, Mar. 2007, pp. 527-534.

Pergola, P. et al. "Ziltivekimab for Treatment of Anemia of Inflammation in Patients on Hemodialysis: Results from a Phase 1/2 Multicenter, Randomized, Double-Blind, Placebo-Controlled Trial." Journal of the American Society of Nephrology, vol. 32, No. 1, Jan. 29, 2021, pp. 211-222.

Petkova, S. B. "Enhanced Half-Life of Genetically Engineered Human IgG1 Antibodies in a Humanized FcRn Mouse Model: Potential Application in Humorally Mediated Autoimmune Disease." International Immunology, vol. 18, Iss. 12, 2006, pp. 1759-1769.

Pietrangelo, A. "Hepcidin in Human Iron Disorders: Therapeutic Implications." Journal of Hepatology, vol. 54, Iss. 1, Jan. 2011, pp. 173-181.

Plenz, G. et al. "Activation of the Cardiac Interleukin-6 System in Advanced Heart Failure." European Journal of Medicine, vol. 3, Iss. 4, Aug. 2001, pp. 415-421.

Poggiali, E. et al. "The Role of TMPRSS6 Polymorphisms in Iron Deficiency Anemia Partially Responsive to Oral Iron Treatment." American Journal of Hematology, vol. 90, Iss. 4, Apr. 2015, pp. 306-309.

Poli, M. et al. "Hepcidin Antagonists for Potential Treatments of Disorders with Hepcidin Excess." Frontiers in Pharmacology, vol. 5, Iss. 86, Apr. 28, 2014, pp. 1-13.

Popp, A. "RGM—From Target Side Effects to a New Indication—Anemia of Chronic Disease." Biomarkers Summit: Europe 2015, Oct. 5-8, 2015, pp. 1-7.

Presta, L. G. et al. "Engineering Therapeutic Antibodies for Improved Function." Biochemical Society Transaction, vol. 30, Aug. 1, 2002, pp. 487-490.

Rajpal, A. et al. "Introduction: Antibody Structure and Function." Therapeutic Fc-Fusion Proteins, Wiley Blackwell, Dec. 13, 2013, pp. 1-43.

Reddy, M. P. et al. "Elimination of Fc Receptor-Dependent Effector Functions of a Modified IgG4 Monoclonal Antibody to Human CD4." The Journal of Immunology, vol. 164, Iss. 4, Feb. 15, 2000, pp. 1925-1933.

Regeneron. "Regeneron and Sanofi Announce Topline Results of Phase 3 Monotherapy Study Demonstrating Superiority of Sarilumab vs. Adalimumab in Patients with Active Rheumatoid Arthritis." Regeneron Pharmaceuticals, Inc., Mar. 11, 2016, pp. 1-3.

Ridker, P. M. et al. "Anti-Inflammatory Therapies for Cardiovascular Disease." European Heart Journal, vol. 35, 2014, pp. 1782-1791.

Ridker, P. M. et al., "Antiinflammatory Therapy with Canakinumab for Atherosclerotic Disease," The New England Journal of Medicine, Sep. 21, 2017, vol. 377, No. 12, pp. 1119-1131.

Ridker, P. M. et al. "C-Reactive Protein and Other Markers of Inflammation in the Prediction of Cardiovascular Disease in Women." The New England Journal of Medicine, vol. 342, Iss. 12, Mar. 23, 2000, pp. 836-843.

Ridker, P. M. et al. "Inhibition of Interleukin-1β by Canakinumab and Cardiovascular Outcomes in Patients With Chronic Kidney Disease." Journal of the American College of Cardiology, vol. 71, Iss. 21, May 29, 2018, pp. 2405-2414.

Ridker, P. M. et al. "Modulation of the Interleukin-6 Signalling Pathway and Incidence Rates of Atherosclerotic Events and All-Cause Mortality: Analyses from the Canakinumab Anti-Inflammatory Thrombosis Outcomes Study (CANTOS)." European Heart Journal, vol. 39, Iss. 38, Oct. 7, 2018, pp. 3499-3507.

Ridker, P. M. et al. "Plasma Concentration of Interleukin-6 and the Risk of Future Myocardial Infarction Among Apparently Healthy Men." Circulation, vol. 101, Iss. 15, Apr. 18, 2000, pp. 1767-1772.

Rispens, T. et al. "Label-Free Assessment of High-Affinity Antibody-Antigen Binding Constants. Comparison of Bioassay, SPR, and PEIA-Ellipsometry." Journal of Immunological Methods, vol. 365, Feb. 28, 2011, pp. 50-57.

Rispens, T. et al. "Nanomolar to Sub-Picomolar Affinity Measurements of Antibody-Antigen Interactions and Protein Multimerizations: Fluorescence-Assisted High-Performance Liquid Chromatography." Analytical Biochemistry, vol. 437, Iss. 2, Jun. 15, 2013, pp. 118-122.

Ronco, C. et al. "Cardiorenal Syndrome." Journal of the American College of Cardiology, vol. 52, Iss. 19, Nov. 4, 2008, pp. 1527-1539.

Rosner, M. H. et al. "The Role of Inflammation in the Cardio-Renal Syndrome: A Focus on Cytokines and Inflammatory Mediators." Seminars in Nephrology, vol. 32, Iss. 1, Jan. 2012, pp. 70-78.

Rossi, J-F. et al. "Interleukin-6 as a Therapeutic Target." Clinical Cancer Research, vol. 21, Iss. 6, Mar. 15, 2015, pp. 1248-1257.

Rothaug, M. et al. "The Role of Interleukin-6 Signaling in Nervous Tissue." Biochimica et Biophysica Acta, vol. 1863, Iss. 6, Part A, Jun. 2016, pp. 1218-1227.

Rubab, Z. et al. "Serum Hepcidin Levels in Patients with End-Stage Renal Disease on Hemodialysis." Saudi Journal of Kidney Diseases and Transplantation, vol. 26, Iss. 1, Jan. 2015, pp. 19-25.

Rudikoff, S. et al. "Single Amino Acid Substitution Altering Antigen-Binding Specificity." PNAS, vol. 79, Mar. 1982, pp. 1979-1983.

Saito, F. et al. "Role of Interleukin-6 in Bleomycin-Induced Lung Inflammatory Changes in Mice." American Journal of Respiratory Cell and Molecular Biology, vol. 38, Iss. 5, May 2008, pp. 566-571.

Sakai, R. et al. "Head-to-Head Comparison of the Safety of Tocilizumab and Tumor Necrosis Factor Inhibitors in Rheumatoid Arthritis Patients (RA) in Clinical Practice: Results from the Registry of Japanese RA Patients on Biologics for Long-Term Safety (REAL) Registry." Arthritis Research & Therapy, vol. 17, Iss. 74, Dec. 2015, pp. 1-10.

Sarwar, N. et al. "Interleukin-6 Receptor Pathways in Coronary Heart Disease: A Collaborative Meta-Analysis of 82 Studies." vol. 379, Mar. 31, 2012, pp. 1205-1213.

Savale, L. et al. "Impact of Interleukin-6 on Hypoxia-Induced Pulmonary Hypertension and Lung Inflammation in Mice." Respiratory Research, vol. 10, Iss. 6, Jan. 27, 2009, pp. 1-13.

Savale, L. et al. "Shortened Telomeres in Circulating Leukocytes of Patients with Chronic Obstructive Pulmonary Disease." American Journal of Respiratory and Critical Care Medicine, vol. 179, Iss. 7, Apr. 1, 2009, pp. 566-571.

Schier, R. et al. "Isolation of High-Affinity Monomeric Human Anti-c-erbB-2 Single Chain Fv Using Affinity-Driven Selection." Journal of Molecular Biology, vol. 255, Iss. 1, Jan. 12, 1996, pp. 28-43.

Schlapschy, M. et al. "Fusion of a Recombinant Antibody Fragment with a Homo-Amino-Acid Polymer: Effects on Biophysical Properties and Prolonged Plasma Half-Life." Protein Engineering, Design & Selection, vol. 20, Iss. 6, 2007, pp. 273-284.

Scinicariello, F. et al. "Rhesus Macaque Antibody Molecules: Sequences and Heterogeneity of Alpha and Gamma Constant Regions." Immonology, vol. 111, Iss. 1, Jan. 2004, pp. 66-74.

Shields, R. L. et al. "High Resolution Mapping of the Binding Site on Human IgG1 for FcγRI, FcγRII, FcγRIII, and FcRn and Design of Ig1 Variants with Improved Binding to the FcγR." The Journal of Biological Chemistry, vol. 276, Iss. 9, Mar. 2, 2001, pp. 6591-6604.

Sieper, J. et al. "Sarilumab for the Treatment of Ankylosing Spondylitis: Results of a Phase II, Randomised, Double-Blind, Placebo-Controlled Study (ALIGN)." Annals of the Rheumatic Diseases, vol. 74, May 2015, pp. 1051-1057.

Singh, A. K. et al. "Correction of Anemia with Epoetin Alfa in Chronic Kidney Disease." The New England Journal of Medicine, vol. 355, Iss. 20, Nov. 16, 2006, pp. 2085-2098.

Slotki, I. N. et al. "Disorders of Sodium Balance." Brenner & Rector's The Kidney, 10th Edition, Philadelphia, PA: Elsevier, Oct. 28, 2015, pp. 390-459.

Smith, B. J. et al. "Prolonged in Vivo Residence Times of Antibody Fragments Associated with Albumin." Bioconjugate Chemistry, vol. 12, 2001, pp. 750-756.

Smith, P. C. et al. "Interleukin-6 and Prostate Cancer Progression." Cytokine and Growth Factor Reviews, vol. 12, Iss. 1, Mar. 2001, pp. 33-40.

(56) References Cited

OTHER PUBLICATIONS

Smith-Gill, S. J. et al. "Contributions of Immunoglobulin Heavy and Light Chains to Antibody Specficity for Lysozyme and Two Haptens." The Journal of Immunology, vol. 139, Iss. 12, Dec. 15, 1987, pp. 4135-4144.
Snpedia. "Rs855791." Last Modified Jun. 28, 2015, 5 pages, [Online] [Retrieved on Sep. 15, 2015] Retrieved from the Internet<URL:http://www.snpedia.com/index.php/Rs855791 >.
Somers, W. et al. "A Crystal Structure of Interleukin 6: Implications for a Novel Mode of Receptor Dimerization and Signaling." The EMBO Journal, vol. 16, Iss. 5, Mar. 3, 1997, pp. 989-997.
Song, M-K. et al. "Light Chain of Natural Antibody Plays a Dominant Role in Protein Antigen Binding." Biochemical and Biophysical Research Communications, vol. 268, Iss. 2, Feb. 16, 2000, pp. 390-394.
Song, S-N. J. et al. "Comparative Evaluation of the Effects of Treatment with Tocilizumab and TNF-α Inhibitors on Serum Hepcidin, Anemia Response and Disease Activity in Rheumatoid Arthritis Patients." Arthritis Research & Therapy, vol. 15, Iss. 5, Oct. 2, 2013, pp. 1-10.
Song, S-N. J. et al. "Down-Regulation of Hepcidin Resulting from Long-Term Treatment with an Anti-IL-6 Receptor Antibody (Tocilizumab) Improves Anemia of Inflammation in Multicentric Castleman Disease." Blood, vol. 116, Iss. 18, Nov. 4, 2010, pp. 3627-3634.
Steinbicker, A. U. et al. "Inhibition of Bone Morphogenetic Protein Signaling Attenuates Anemia Associated with Inflammation." Blood, vol. 117, Iss. 18, May 5, 2011, pp. 4915-4923.
Steiner, M. K. et al. "Interleukin-6 Overexpression Induces Pulmonary Hypertension." Circulation Research, vol. 104, Iss. 2, Jan. 2009, pp. 236-244.
Stork, R. et al. "A Novel Tri-Functional Antibody Fusion Protein with Improved Pharmacokinetic Properties Generated by Fusing a Bispecific Single-Chain Diabody with an Albumin-Binding Domain from Streptococcal Protein G." Protein Engineering, Design & Selection, vol. 20, Iss. 11, 2007, pp. 569-576.
Su, H. et al. "Interleukin-6 Signaling Pathway and its Role in Kidney Disease: An Update." Frontiers in Immunology, vol. 8, Article 405, Apr. 2017, pp. 1-10.
Sun, C. C. et al. "Targeting the Hepcidin-Ferroportin Axis to Develop New Treatment Strategies for Anemia of Chronic Disease and Anemia of Inflammation." American Journal of Hematology, vol. 87, Iss. 4, Apr. 2012, pp. 392-400.
Swerdlow, D. et al. "The Interleukin-6 Receptor as a Target for Prevention of Coronary Heart Disease: A Mendelian Randomisation Analysis." The Lancet, vol. 379, No. 9822, Mar. 31, 2012, pp. 1214-1224.
Sylvant Label, 2014, Reference ID: 3493425, 16 pages.
Szymanski, M. K. et al. "Animal Models of Cardiorenal Syndrome: A Review." Heart Failure Reviews, vol. 17, Iss. 3, May 2012, pp. 411-420.
Tamura, T. et al. "Soluble Interleukin-6 Receptr Triggers Osteoclast Formation by Interleukin 6." Proceedings of the National Academy of Science, vol. 90, Dec. 1993, pp. 11924-11928.
Tanaka, T. et al. "A Genome-Wide Association Analysis of Serum Iron Concentrations." Blood, vol. 115, Iss. 1, Jan. 2010, pp. 94-96.
Tanaka, T. et al. "A New Era for the Treatment of Inflammatory Autoimmune Diseases by Interleukin-6 Blockade Strategy." Seminars in Immunology, vol. 26, Iss. 1, Feb. 2014, pp. 88-96.
Tanaka, T. et al. "Interleukin-6 Inhibition in Inflammatory Diseases: Results Achieved and Tasks to Accomplish." Journal of Scleroderma and Related Disorders, vol. 2, No. 2, Aug. 12, 2017, pp. S20-S28.
Tanaka, T. et al. "Targeting Interleukin-6: All the Way to Treat Autoimmune and Inflammatory Diseases." International Journal of Biological Sciences, vol. 8, No. 9, Oct. 24, 2012, pp. 1227-1236.
Tanaka, Y. et al. "IL-6 Targeting Compared to TNF Targeting in Rheumatoid Arthritis: Studies of Olokizumab, Sarilumab and Sirukumab." Annals of the Rheumatic Diseases, vol. 73, Iss. 9, Sep. 2014, pp. 1595-1597.

Ter Maaten, J.M. et al., "A combined clinical and biomarker approach to predict diuretic response in acute heart failure," Clin Res Cardiol, 2016, vol. 105, pp. 145-153.
The Japan Patent Office, Office Action, Japanese Patent Application No. 2018-525517, Jul. 7, 2020, eight pages.
Thorleifsson, S. J. et al. "Chronic Airflow Obstruction and Markers of Systemic Inflammation: Results from the BOLD Study in Iceland." Respiratory Medicine, vol. 103, Iss. 10, Oct. 2009, pp. 1548-1553.
Tsutamoto, T. et al. "Interleukin-6 Spillover in the Peripheral Circulation Increases with the Severity of Heart Failure, and the High Plasma Level of Interleukin-6 is an Important Prognostic Predictor in Patients with Congestive Heart Failure." Journal of the American College of Cardiology, vol. 31, No. 2, Feb. 1998, pp. 391-398.
Udagawa, N. et al. "Interleukin (IL)-6 Induction of Osteoclast Differentiation Depends on IL-6 Receptors Expressed on Osteoblastic Cells but not on Osteoclast Progenitors." Journal of Experimental Medicine, vol. 182, Iss. 5, Nov. 1, 1995, pp. 1461-1468.
United States Office Action, U.S. Appl. No. 13/146,278, Dec. 19, 2013, 40 pages.
United States Office Action, U.S. Appl. No. 14/253,161, Jul. 28, 2015, 23 pages.
United States Office Action, U.S. Appl. No. 14/253,161, Sep. 2, 2016, 18 pages.
United States Office Action, U.S. Appl. No. 14/253,161, Feb. 26, 2016, 15 pages.
United States Office Action, U.S. Appl. No. 14/437,585, Dec. 28, 2016, 9 pages.
United States Office Action, U.S. Appl. No. 14/675,980, Sep. 19, 2016, 36 pages.
United States Office Action, U.S. Appl. No. 15/222,507, Aug. 8, 2019, 11 pages.
United States Office Action, U.S. Appl. No. 15/222,507, Mar. 30, 2018, 13 pages.
United States Office Action, U.S. Appl. No. 15/222,507, Nov. 8, 2018, 11 pages.
United States Office Action, U.S. Appl. No. 16/396,378, Sep. 20, 2019, 17 pages.
United States Office Action, U.S. Appl. No. 16/396,378, Apr. 2, 2020, 20 pages.
United States Office Action, U.S. Appl. No. 16/482,038, Sep. 25, 2020, 14 pages.
United States Office Action, U.S. Appl. No. 15/222,507, Dec. 10, 2020, 12 pages.
United States Office Action, U.S. Appl. No. 16/482,038, Mar. 16, 2021, 22 pages.
United States Office Action, U.S. Appl. No. 16/396,378, May 24, 2021, 11 pages.
United States Office Action, U.S. Appl. No. 16/482,038, Jul. 8, 2021, 14 pages.
United States Patent and Trademark Office, Restriction Requirement, U.S. Appl. No. 16/482,038, Jun. 8, 2020, eight pages.
Uson, J. et al. "Soluble Interleukin 6 (IL-6) Receptor and IL-6 Levels in Serum and Synovial Fluid of Patients with Different Arthropathies." The Journal of Rheumatology, vol. 24, Iss. 11, Nov. 1997, pp. 2069-2075.
Vajdos, F. F. et al. "Comprehensive Functional Maps of the Antigen-Binding Site of an Anti-ErbB2 Antibody Obtained with Shotgun Scanning Mutagenesis." Journal of Molecular Biology, vol. 320, Iss. 2, Jul. 2002, pp. 415-428.
Valencik, M. L. et al. "Codon Optimization Markedly Improves Doxycycline Regulated Gene Expression in the Mouse Heart." Transgenic Research, vol. 10, Iss. 3, Jun. 2001, pp. 269-275.
Valenti, L. et al. "Effect of the A736V TMPRSS6 Polymorphism on the Penetrance and Clinical Expression of Hereditary Hemochromatosis." Journal of Hepatology, vol. 57, No. 6, Dec. 2012, pp. 1319-1325.
Valipour, A. et al. "Circulating Vascular Endothelial Growth Factor and Systemic Inflammatory Markers in Patients with Stable and Exacerbated Chronic Obstructive Pulmonary Disease." Clinical Science, vol. 115, Iss. 7, Oct. 2008, pp. 225-232.

(56)                    References Cited

OTHER PUBLICATIONS

Van Rhee, F. et al. "A Phase 2, Open-Label, Multicenter Study of the Long-Term Safety of Siltuximab (an Anti-Interleukin-6 Monoclonal Antibody) in Patients with Multicentric Castleman Disease." Oncotarget, vol. 6, No. 30, Oct. 6, 2015, pp. 30408-30419.

Van Rhee, F. et al. "Siltuximab, a Novel Anti-Interleukin-6 Monoclonal Antibody, for Castleman's Disease." Journal of Clinical Oncology, vol. 28, Iss. 23, Aug. 10, 2010, pp. 3701-3708.

Van Zaanen, H. C. T. et al. "Chimaeric Anti-Interleukin 6 Monoclonal Antibodies in the Treatment of Advanced Multiple Myeloma: A Phase I Dose-Escalating Study." British Journal of Haematology, vol. 102, Iss. 3, Aug. 1998, pp. 783-790.

Van Zaanen, H. C. T. et al. "Endogenous Interleukin 6 Production in Multiple Myeloma Patients Treated with Chimeric Monoclonal Anti-IL6 Antibodies Indicates the Existence of a Positive Feed-Back Loop." The American Society for Clinical Investigation, Inc., vol. 98, Iss. 6, Sep. 1996, pp. 1441-1448.

Varghese, J. N. et al. "Structure of the Extracellular Domains of the Human Interleukin-6 Receptor α-Chain." PNAS, vol. 99, Iss. 25, Dec. 10, 2002, pp. 15959-15964.

Verma, S. et al. "Endothelin Antagonism and Interleukin-6 Inhibition Attenuate the Proatherogenic Effects of C-Reactive Protein." Circulation, vol. 105, No. 16, Apr. 23, 2002, pp. 1890-1896.

Voors, A. A. et al. "A Systems BIOlogy Study to TAilored Treatment in Chronic Heart Failure: Rationale, Design, and Baseline Characteristics of BIOSTAT-CHF." European Journal of Heart Failure, vol. 18, 2016, pp. 716-726.

Voors, A. A. et al. "Development and Validation of Multivariable Models to Predict Mortality and Hospitalization in Patients with Heart Failure." vol. 19, Iss. 5, May 2017, pp. 627-634.

Wallenius, V. et al. "Interleukin-6-Deficient Mice Develop Mature-Onset Obesity." Nature Medicine, vol. 8, Iss. 1, Jan. 2002, pp. 75-79.

Walter, R. E. et al. "Systemic Inflammation and COPD." Chest, vol. 133, Iss. 1, Jan. 2008, pp. 19-25.

Wang, C-Y. et al. "The Role of TMPRSS6/matriptase-2 in Iron Regulation and Anemia." Frontiers in Pharmacology, vol. 5, May 19, 2014, pp. 1-6.

Ward, E. S. et al. "Binding Activites of a Repertoire of Single Immunoglobulin Variable Domains Secreted from *Escherichia coli*." Nature, vol. 341, Oct. 1989, pp. 544-546.

Weatherly, B. D. et al. "Design and Rationale of the PROTECT Study: A Placebo-controlled Randomized Study of the Selective A1 Adenosine Receptor Antagonist Rolofylline for Patients Hospitalized With Acute Decompensated Heart Failure and Volume Overload to Assess Treatment Effect on Congestion and Renal Function." Journal of Cardiac Failure, vol. 16, Iss. 1, Jan. 2010, pp. 25-35.

Weinstein, D. A. et al. "Inappropriate Expression of Hepcidin is Associated with Iron Refractory Anemia: Implications for the Anemia of Chronic Disease." Blood, vol. 100, Iss. 10, Nov. 15, 2002, pp. 3776-3781.

Wendling, D. et al. "Treatment of Severe Rheumatoid Arthritis by Anti-Interleukin 6 Monoclonal Antibody." The Journal of Rheumatology, vol. 20, Iss. 2, Jan. 31, 1993, pp. 259-262.

Wijdenes, J. et al. "Human Recombinant Dimeric IL-6 Binds to its Receptor as Detected by Anti-IL-6 Monoclonal Antibodies." Molecular Immunology, vol. 28, Iss. 11, Nov. 1991, pp. 1183-1192.

Winkler, K. et al. "Changing the Antigen Binding Specificity by Single Point Mutations of an Anti-p24 (HIV-1) Antibody." The Journal of Immunology, vol. 165, Iss. 8, 2000, pp. 4505-4514.

Winthrop, K. L. et al. "Opportunistic Infections and Biologic Therapies in Immune-Mediated Inflammatory Diseases: Consensus Recommendations for Infection Reporting During Clinical Trials and Postmarketing Surveillance." Annals of the Rheumatic Diseases, vol. 74, Iss. 12, Sep. 22, 2015, pp. 2107-2116.

Won, H. S. et al. "IL-6 is an Independent Risk Factor for Resistance to Erythropoiesis-Stimulating Agents in Hemodialysis Patients without Iron Deficiency." Hemodialysis International, vol. 16, Iss. 1, Jan. 2021, pp. 31-37.

Wu, H. et al. "Humanization of a Murine Monoclonal Antibody by Simultaneous Optimization of Framework and CDR Residues." Journal of Molecular Biology, vol. 294, Iss. 1, Nov. 19, 1999, pp. 151-162.

Xu, D. et al. "In Vitro Characterization of Five Humanized OKT3 Effector Function Variant Antibodies." Cellular Immunology, vol. 200, Iss. 1, Feb. 25, 2000, pp. 16-26.

Yan, A. T. et al. "Relationship of Interleukin-6 with Regional and Global Left-Ventricular Function in Asymptomatic Individuals without Clinical Cardiovascular Disease: Insights from the Multi-Ethnic Study of Atherosclerosis." European Heart Journal, vol. 31, No. 7, Apr. 2010, pp. 875-882.

Yanbaeva, D. G. et al. "IL6 and CRP Haplotypes are Associated with COPD Risk and Systemic Inflammation: A Case-Control Study." BMC Medical Genetics, vol. 10, Iss. 23, Mar. 9, 2009, pp. 1-11.

Yeun, J. Y. et al. "C-Reactive Protein Predicts All-Cause and Cardiovascular Mortality in Hemodialysis Patients." American Journal of Kidney Diseases, vol. 35, Iss. 3, Mar. 2000, pp. 469-476.

Yeung, Y. A. et al. "Engineering Human IgG1 Affinity to Human Neonatal Fc Receptor: Impact of Affinity Improvement on Pharmacokinetics in Primates." The Journal of Immunology, vol. 182, 2009, pp. 7663-7671.

Yokota, S. et al. "Therapeutic Efficacy of Humanized Recombinant Anti-Interleukin-6 Receptor Antibody in Children with Systemic-Onset Juvenile Idiopathic Arthirtis." Arthritis & Rheumatism, vol. 52, No. 3, Mar. 2005, pp. 818-825.

Yoshida, K. et al. "Targeted Disruption of gp130, a Common Signal Transducer for the Interleukin 6 Family of Cytokines, Leads to Myocardial and Hematological Disorders." PNAS, vol. 93, Jan. 1996, pp. 407-411.

Zhang, J. et al. "Anti-IL-6 Neutralizing Antibody Modulates Blood-Brain Barrier Function in the Ovine Fetus." The FASEB Journal, vol. 29, Iss. 5, May 2015, pp. 1739-1753.

Zhang, W. et al. "Interleukin 6 Underlies Angiotensin II-Induced Hypertension and Chronic Renal Damage." Hypertension, vol. 59, Iss. 1, Jan. 2012, pp. 136-144.

De Falco, L. et al. "Iron Refractory Iron Deficiency Anemia." Haematologica, vol. 98, No. 6, Jun. 2013, pp. 845-853.

Keskin, E. Y. et al. "Iron-Refractory Iron Deficiency Anemia." Turkish Journal of Hematology, vol. 32, No. 1, Mar. 2015, pp. 1-14.

Lee, P. "Role of Matriptase-2 (TMPRSS6) in Iron Metabolism." Acta Haematologica, vol. 122, No. 2-3, Nov. 10, 2009, pp. 87-96.

Pelusi, S. et al. "The A736V TMPRSS6 Polymorphism Influences Hepcidin and Iron Metabolism in Chronic Hemodialysis Patients: TMPRSS6 and Hepcidin in Hemodialysis." BMC Nephrology, vol. 14, Feb. 22, 2013, pp. 1-9.

Raj, D. S. C. "Role of Interleukin-6 in the Anemia of Chronic Disease." Seminars in Arthritis and Rheumatism, vol. 38, No. 5, Apr. 2009, pp. 382-388.

Rossi, J-F. et al. "A Phase I/II Study of Siltuximab (CNTO 328), an Anti-Interleukin-6 Monoclonal Antibody, in Metastatic Renal Cell Cancer." British Journal of Cancer, vol. 103, Aug. 31, 2010, pp. 1154-1162.

Schipperus, M. et al. "CNTO328 (Anti-IL-6 mAb) Treatment is Associated with an Increase in Hemoglobin (Hb) and Decrease in Hepcidin Levels in Renal Cell Carcinoma (RCC)." Blood, vol. 114, No. 22, Nov. 20, 2009, pp. 1-3.

Macgowan, G. A. et al. "Circulating Interleukin-6 in Severe Heart Failure." The American Journal of Cardiology, vol. 79, No. 8, Apr. 15, 1997, pp. 1128-1131.

Ridker, P. M. et al. "IL-6 Inhibition with Ziltivekimab in Patients at High Atherosclerotic Risk (RESCUE): A Double-Blind, Randomised, Placebo-Controlled, Phase 2 Trial." The Lancet, vol. 397, No. 10289, May 29, 2021, pp. 2060-2069.

Benucci, M. et al. "Changes in Atherosclerosis Markers During Tocilizumab Treatment in Rheumatoid Arthritis: Preliminary Results." Clinical and Experimental Rheumatology, vol. 31, No. 2, Mar.-Apr. 2013, pp. 322-323.

Boekholdt, S. M. et al. "The Interleukin-6 Pathway and Atherosclerosis." The Lancet, vol. 379, No. 9822, Mar. 2012, pp. 1176-1178.

(56)              References Cited

OTHER PUBLICATIONS

Kato, A. et al. "Association Between Interleukin-6 and Carotid Atherosclerosis in Hemodialysis Patients." Kidney International, vol. 61, No. 3, Mar. 2002, pp. 1143-1152.

Strang, A. C. et al. "Pro-Atherogenic Lipid Changes and Decreased Hepatic LDL Receptor Expression by Tocilizumab in Rheumatoid Arthritis." Atherosclerosis, vol. 229, No. 1, Jul. 2013, pp. 174-181.

Toblli, J. E. et al. "Heart and Iron Deficiency Anaemia in Rats with Renal Insufficiency: The Role of Hepcidin." Nephrology, vol. 13, No. 7, Oct. 2008, pp. 636-645.

Nowak et al., "A Study of Patients with Chronic Kidney Disease to Assess the Safety of a Single Dose of COR-001", ClinicalTrials.gov, Apr. 2017, pp. 1-7.

Orlowski et al., "A phase 2, randomized, double-blind, placebo-controlled study of siltuximab (anti-IL-6 mAb) and bortezomib versus bortezomib alone in patients with relapsed or refractory multiple myeloma", Am J Hematol, Jan. 2015, vol. 90, Issue 1, pp. 1-20.

Stevens et al., "Surrogate end points for clinical trials of kidney disease progression", Clin J Am Soc Nephrol, Jun. 2006, vol. 1, pp. 874-884.

Jones et al., "Interleukin-6 in renal disease and therapy", Nephrology Dialysis Transplantation, Jul. 2014, vol. 30, Issue 4, pp. 564-574.

Amiri, "Aggravation of chronic kidney disease by inflammatory factors; a narrative review on current concept", Journal of Renal Endocrinology, May 2016, vol. 2, pp. 1-6.

"Kdigo 2012 clinical practice guideline for the evaluation and management of chronic kidney disease", Kidney International Supplements, Jan. 2013, vol. 3, Issue 1, pp. 1-150.

Polkinghorne, "Estimated Glomerular Filtration Rate versus Albuminuria in the Assessment of Kidney Function: What's More Important?", Clin Biochem Rev, May 2014, vol. 35, No. 2, pp. 67-73.

Ptaszynska-Kopczynska et al., "Interleukin-6 signaling in patients with chronic heart failure treated with cardiac resynchronization therapy", Arch. Med. Sci., Mar. 2016, vol. 13, No. 5, pp. 1069-1077.

BIOSTAT

All-cause mortality and/or rehospitalization for HF at 2 years

FIG. 10A

```
SEQUENCE LISTING

<160> NUMBER OF SEQ ID NOS: 16

<210> SEQ ID NO 1
<211> LENGTH: 824
<212> TYPE: PRT
<213> ORGANISM: Homo sapiens

<400> SEQUENCE: 1

Met Pro Val Ala Glu Ala Pro Gln Val Ala Gly Gly Gln Gly Asp Gly
1               5                   10                  15

Gly Asp Gly Glu Glu Ala Glu Pro Glu Gly Met Phe Lys Ala Cys Glu
            20                  25                  30

Asp Ser Lys Arg Lys Ala Arg Gly Tyr Leu Arg Leu Val Pro Leu Phe
        35                  40                  45

Val Leu Leu Ala Leu Leu Val Leu Ala Ser Ala Gly Val Leu Leu Trp
    50                  55                  60

Tyr Phe Leu Gly Tyr Lys Ala Glu Val Met Val Ser Gln Val Tyr Ser
65                  70                  75                  80

Gly Ser Leu Arg Val Leu Asn Arg His Phe Ser Gln Asp Leu Thr Arg
                85                  90                  95

Arg Glu Ser Ser Ala Phe Arg Ser Glu Thr Ala Lys Ala Gln Lys Met
            100                 105                 110

Leu Lys Glu Leu Ile Thr Ser Thr Arg Leu Gly Thr Tyr Tyr Asn Ser
        115                 120                 125

Ser Ser Val Tyr Ser Phe Gly Glu Gly Pro Leu Thr Cys Phe Phe Trp
    130                 135                 140

Phe Ile Leu Gln Ile Pro Glu His Arg Arg Leu Met Leu Ser Pro Glu
145                 150                 155                 160

Val Val Gln Ala Leu Leu Val Glu Glu Leu Leu Ser Thr Val Asn Ser
                165                 170                 175

Ser Ala Ala Val Pro Tyr Arg Ala Glu Tyr Glu Val Asp Pro Glu Gly
                180                 185                 190
```

-continued

```
Leu Val Ile Leu Glu Ala Ser Val Lys Asp Ile Ala Ala Leu Asn Ser
        195                 200             205

Thr Leu Gly Cys Tyr Arg Tyr Ser Tyr Val Gly Gln Gly Gln Val Leu
    210                 215                 220

Arg Leu Lys Gly Pro Asp His Leu Ala Ser Ser Cys Leu Trp His Leu
225                 230                 235                 240

Gln Gly Pro Lys Asp Leu Met Leu Lys Leu Arg Leu Glu Trp Thr Leu
                245                 250                 255

Ala Glu Cys Arg Asp Arg Leu Ala Met Tyr Asp Val Ala Gly Pro Leu
                260                 265                 270

Glu Lys Arg Leu Ile Thr Ser Val Tyr Gly Cys Ser Arg Gln Glu Pro
            275                 280                 285

Val Val Glu Val Leu Ala Ser Gly Ala Ile Met Ala Val Val Trp Lys
        290                 295                 300

Lys Gly Leu His Ser Tyr Tyr Asp Pro Phe Val Leu Ser Val Gln Pro
305                 310                 315                 320

Val Val Phe Gln Ala Cys Glu Val Asn Leu Thr Leu Asp Asn Arg Leu
                325                 330                 335

Asp Ser Gln Gly Val Leu Ser Thr Pro Tyr Phe Pro Ser Tyr Tyr Ser
                340                 345                 350

Pro Gln Thr His Cys Ser Trp His Leu Thr Val Pro Ser Leu Asp Tyr
            355                 360                 365

Gly Leu Ala Leu Trp Phe Asp Ala Tyr Ala Leu Arg Arg Gln Lys Tyr
        370                 375                 380

Asp Leu Pro Cys Thr Gln Gly Gln Trp Thr Ile Gln Asn Arg Arg Leu
385                 390                 395                 400

Cys Gly Leu Arg Ile Leu Gln Pro Tyr Ala Glu Arg Ile Pro Val Val
                405                 410                 415

Ala Thr Ala Gly Ile Thr Ile Asn Phe Thr Ser Gln Ile Ser Leu Thr
                420                 425                 430

Gly Pro Gly Val Arg Val His Tyr Gly Leu Tyr Asn Gln Ser Asp Pro
            435                 440                 445

Cys Pro Gly Glu Phe Leu Cys Ser Val Asn Gly Leu Cys Val Pro Ala
        450                 455                 460

Cys Asp Gly Val Lys Asp Cys Pro Asn Gly Leu Asp Glu Arg Asn Cys
465                 470                 475                 480

Val Cys Arg Ala Thr Phe Gln Cys Lys Glu Asp Ser Thr Cys Ile Ser
                485                 490                 495

Leu Pro Lys Val Cys Asp Gly Gln Pro Asp Cys Leu Asn Gly Ser Asp
                500                 505                 510

Glu Glu Gln Cys Gln Glu Gly Val Pro Cys Gly Thr Phe Thr Phe Gln
            515                 520                 525

Cys Glu Asp Arg Ser Cys Val Lys Lys Pro Asn Pro Gln Cys Asp Gly
        530                 535                 540

Arg Pro Asp Cys Arg Asp Gly Ser Asp Glu Glu His Cys Asp Cys Gly
545                 550                 555                 560

Leu Gln Gly Pro Ser Ser Arg Ile Val Gly Gly Ala Val Ser Ser Glu
                565                 570                 575

Gly Glu Trp Pro Trp Gln Ala Ser Leu Gln Val Arg Gly Arg His Ile
                580                 585                 590

Cys Gly Gly Ala Leu Ile Ala Asp Arg Trp Val Ile Thr Ala Ala His
            595                 600                 605
```

```
Cys Phe Gln Glu Asp Ser Met Ala Ser Thr Val Leu Trp Thr Val Phe
    610             615                 620

Leu Gly Lys Val Trp Gln Asn Ser Arg Trp Pro Gly Glu Val Ser Phe
625             630                 635                 640

Lys Val Ser Arg Leu Leu Leu His Pro Tyr His Glu Glu Asp Ser His
                645                 650                 655

Asp Tyr Asp Val Ala Leu Leu Gln Leu Asp His Pro Val Val Arg Ser
            660                 665                 670

Ala Ala Val Arg Pro Val Cys Leu Pro Ala Arg Ser His Phe Phe Glu
        675                 680                 685

Pro Gly Leu His Cys Trp Ile Thr Gly Trp Gly Ala Leu Arg Glu Gly
    690                 695                 700

Ala Leu Arg Ala Asp Ala Val Ala Leu Phe Tyr Gly Trp Arg Asn Gln
705                 710                 715                 720

Gly Ser Glu Thr Cys Cys Pro Ile Ser Asn Ala Leu Gln Lys Ala
                725                 730                 735

Asp Val Gln Leu Ile Pro Gln Asp Leu Cys Ser Glu Val Tyr Arg Tyr
            740                 745                 750

Gln Val Thr Pro Arg Met Leu Cys Ala Gly Tyr Arg Lys Gly Lys Lys
        755                 760                 765

Asp Ala Cys Gln Gly Asp Ser Gly Gly Pro Leu Val Cys Lys Ala Leu
    770                 775                 780

Ser Gly Arg Trp Phe Leu Ala Gly Leu Val Ser Trp Gly Leu Gly Cys
785                 790                 795                 800

Gly Arg Pro Asn Tyr Phe Gly Val Tyr Thr Arg Ile Thr Gly Val Ile
                805                 810                 815

Ser Trp Ile Gln Gln Val Val Thr
                820
```

```
<210> SEQ ID NO 2
<211> LENGTH: 824
<212> TYPE: PRT
<213> ORGANISM: Homo sapiens

<400> SEQUENCE: 2
```

```
Met Pro Val Ala Glu Ala Pro Gln Val Ala Gly Gly Gln Gly Asp Gly
1               5                   10                  15

Gly Asp Gly Glu Glu Ala Glu Pro Glu Gly Met Phe Lys Ala Cys Glu
            20                  25                  30

Asp Ser Lys Arg Lys Ala Arg Gly Tyr Leu Arg Leu Val Pro Leu Phe
        35                  40                  45

Val Leu Leu Ala Leu Leu Val Leu Ala Ser Ala Gly Val Leu Leu Trp
    50                  55                  60

Tyr Phe Leu Gly Tyr Lys Ala Glu Val Met Val Ser Gln Val Tyr Ser
65                  70                  75                  80

Gly Ser Leu Arg Val Leu Asn Arg His Phe Ser Gln Asp Leu Thr Arg
                85                  90                  95

Arg Glu Ser Ser Ala Phe Arg Ser Glu Thr Ala Lys Ala Gln Lys Met
            100                 105                 110

Leu Lys Glu Leu Ile Thr Ser Thr Arg Leu Gly Thr Tyr Tyr Asn Ser
        115                 120                 125

Ser Ser Val Tyr Ser Phe Gly Glu Gly Pro Leu Thr Cys Phe Phe Trp
    130                 135                 140

Phe Ile Leu Gln Ile Pro Glu His Arg Arg Leu Met Leu Ser Pro Glu
145                 150                 155                 160
```

```
Val Val Gln Ala Leu Leu Val Glu Glu Leu Leu Ser Thr Val Asn Ser
            165             170             175

Ser Ala Ala Val Pro Tyr Arg Ala Glu Tyr Glu Val Asp Pro Glu Gly
            180             185             190

Leu Val Ile Leu Glu Ala Ser Val Lys Asp Ile Ala Ala Leu Asn Ser
            195             200             205

Thr Leu Gly Cys Tyr Arg Tyr Ser Tyr Val Gly Gln Gly Gln Val Leu
        210             215             220

Arg Leu Lys Gly Pro Asp His Leu Ala Ser Ser Cys Leu Trp His Leu
225             230             235             240

Gln Gly Pro Lys Asp Leu Met Leu Lys Leu Arg Leu Glu Trp Thr Leu
                245             250             255

Ala Glu Cys Arg Asp Arg Leu Ala Met Tyr Asp Val Ala Gly Pro Leu
            260             265             270

Glu Lys Arg Leu Ile Thr Ser Val Tyr Gly Cys Ser Arg Gln Glu Pro
            275             280             285

Val Val Glu Val Leu Ala Ser Gly Ala Ile Met Ala Val Val Trp Lys
        290             295             300

Lys Gly Leu His Ser Tyr Tyr Asp Pro Phe Val Leu Ser Val Gln Pro
305             310             315             320

Val Val Phe Gln Ala Cys Glu Val Asn Leu Thr Leu Asp Asn Arg Leu
            325             330             335

Asp Ser Gln Gly Val Leu Ser Thr Pro Tyr Phe Pro Ser Tyr Tyr Ser
            340             345             350

Pro Gln Thr His Cys Ser Trp His Leu Thr Val Pro Ser Leu Asp Tyr
            355             360             365

Gly Leu Ala Leu Trp Phe Asp Ala Tyr Ala Leu Arg Arg Gln Lys Tyr
        370             375             380

Asp Leu Pro Cys Thr Gln Gly Gln Trp Thr Ile Gln Asn Arg Arg Leu
385             390             395             400

Cys Gly Leu Arg Ile Leu Gln Pro Tyr Ala Glu Arg Ile Pro Val Val
            405             410             415

Ala Thr Ala Gly Ile Thr Ile Asn Phe Thr Ser Gln Ile Ser Leu Thr
            420             425             430

Gly Pro Gly Val Arg Val His Tyr Gly Leu Tyr Asn Gln Ser Asp Pro
            435             440             445

Cys Pro Gly Glu Phe Leu Cys Ser Val Asn Gly Leu Cys Val Pro Ala
        450             455             460

Cys Asp Gly Val Lys Asp Cys Pro Asn Gly Leu Asp Glu Arg Asn Cys
465             470             475             480

Val Cys Arg Ala Thr Phe Gln Cys Lys Glu Asp Ser Thr Cys Ile Ser
            485             490             495

Leu Pro Lys Val Cys Asp Gly Gln Pro Asp Cys Leu Asn Gly Ser Asp
            500             505             510

Glu Glu Gln Cys Gln Glu Gly Val Pro Cys Gly Thr Phe Thr Phe Gln
            515             520             525

Cys Glu Asp Arg Ser Cys Val Lys Lys Pro Asn Pro Gln Cys Asp Gly
        530             535             540

Arg Pro Asp Cys Arg Asp Gly Ser Asp Glu Glu His Cys Asp Cys Gly
545             550             555             560

Leu Gln Gly Pro Ser Ser Arg Ile Val Gly Gly Ala Val Ser Ser Glu
                565             570             575
```

```
Gly Glu Trp Pro Trp Gln Ala Ser Leu Gln Val Arg Gly Arg His Ile
            580                 585                 590

Cys Gly Gly Ala Leu Ile Ala Asp Arg Trp Val Ile Thr Ala Ala His
        595                 600                 605

Cys Phe Gln Glu Asp Ser Met Ala Ser Thr Val Leu Trp Thr Val Phe
        610                 615                 620

Leu Gly Lys Val Trp Gln Asn Ser Arg Trp Pro Gly Glu Val Ser Phe
625                 630                 635                 640

Lys Val Ser Arg Leu Leu Leu His Pro Tyr His Glu Glu Asp Ser His
                645                 650                 655

Asp Tyr Asp Val Ala Leu Leu Gln Leu Asp His Pro Val Val Arg Ser
            660                 665                 670

Ala Ala Val Arg Pro Val Cys Leu Pro Ala Arg Ser His Phe Phe Glu
            675                 680                 685

Pro Gly Leu His Cys Trp Ile Thr Gly Trp Gly Ala Leu Arg Glu Gly
            690                 695                 700

Ala Leu Arg Ala Asp Ala Val Ala Leu Phe Tyr Gly Trp Arg Asn Gln
705                 710                 715                 720

Gly Ser Glu Thr Cys Cys Cys Pro Ile Ser Asn Ala Leu Gln Lys Val
                725                 730                 735

Asp Val Gln Leu Ile Pro Gln Asp Leu Cys Ser Glu Val Tyr Arg Tyr
            740                 745                 750

Gln Val Thr Pro Arg Met Leu Cys Ala Gly Tyr Arg Lys Gly Lys Lys
            755                 760                 765

Asp Ala Cys Gln Gly Asp Ser Gly Gly Pro Leu Val Cys Lys Ala Leu
            770                 775                 780

Ser Gly Arg Trp Phe Leu Ala Gly Leu Val Ser Trp Gly Leu Gly Cys
785                 790                 795                 800

Gly Arg Pro Asn Tyr Phe Gly Val Tyr Thr Arg Ile Thr Gly Val Ile
                805                 810                 815

Ser Trp Ile Gln Gln Val Val Thr
            820
```

<210> SEQ ID NO 3
<211> LENGTH: 3196
<212> TYPE: DNA
<213> ORGANISM: Homo sapiens

<400> SEQUENCE: 3

```
ggacaaacag aggctcctga ggcctgtgtg caggcccggc acctatctgc cgctcccaaa      60
ggatgcccgt ggccgaggcc ccccaggtgg ctggcgggca gggggacgga ggtgatggcg     120
aggaagcgga gccggagggg atgttcaagg cctgtgagga ctccaagaga aaagcccggg     180
gctacctccg cctggtgccc ctgtttgtgc tgctggccct gctcgtgctg gcttcggcgg     240
gggtgctact ctggtatttc ctagggtaca aggcggaggt gatggtcagc caggtgtact     300
caggcagtct gcgtgtactc aatcgccact tctcccagga tcttacccgc cgggaatcta     360
gtgccttccg cagtgaaacc gccaaagccc agaagatgct caaggagctc atcaccagca     420
cccgcctggg aacttactac aactccagct ccgtctattc ctttgggag ggaccccctca     480 cctgcttctt ctggttcatt ctccaaatcc ccgagcaccg ccggctgatg ctgagccccg     540
aggtggtgca ggcactgctg gtggaggagc tgctgtccac agtcaacagc tcggctgccg     600
tcccctacag ggccgagtac gaagtggacc ccgagggcct agtgatcctg aagccagtg     660 tgaaagacat agctgcattg aattccacgc tgggttgtta ccgctacagc tacgtgggcc     720
```

-continued

```
agggccaggt cctccggctg aaggggcctg accacctggc ctccagctgc ctgtggcacc        780
tgcagggccc caaggacctc atgctcaaac tccggctgga gtggacgctg gcagagtgcc        840
gggaccgact ggccatgtat gacgtggccg ggcccctgga gaagaggctc atcacctcgg        900
tgtacggctg cagccgccag gagcccgtgg tggaggttct ggcgtcgggg gccatcatgg        960
cggtcgtctg gaagaagggc ctgcacagct actacgaccc cttcgtgctc tccgtgcagc       1020
cggtggtctt ccaggcctgt gaagtgaacc tgacgctgga caacaggctc gactcccagg       1080
gcgtcctcag cacccgtac ttccccagct actactcgcc ccaaacccac tgctcctggc        1140
acctcacggt gccctctctg gactacggct ggccctctg gtttgatgcc tatgcactga        1200
ggaggcagaa gtatgatttg ccgtgcaccc agggccagtg gacgatccag aacaggaggc       1260
tgtgtggctt gcgcatcctg cagccctacg ccgagaggat ccccgtggtg gccacggccg       1320
ggatcaccat caacttcacc tcccagatct ccctcaccgg gcccggtgtg cgggtgcact       1380
atggcttgta caaccagtcg gacccctgcc ctggagagtt cctctgttct gtgaatggac       1440
tctgtgtccc tgcctgtgat ggggtcaagg actgccccaa cggcctggat gagagaaact       1500
gcgtttgcag agccacattc cagtgcaaag aggacagcac atgcatctca ctgcccaagg       1560
tctgtgatgg gcagcctgat tgtctcaacg gcagcgacga agagcagtgc caggaagggg       1620
tgccatgtgg gacattcacc ttccagtgtg aggaccggag ctgcgtgaag aagcccaacc       1680
cgcagtgtga tgggcggccc gactgcaggg acggctcgga tgaggagcac tgtgactgtg       1740
gcctccaggg cccctccagc cgcattgttg gtggagctgt gtcctccgag ggtgagtggc       1800
catggcaggc cagcctccag gttcggggtc gacacatctg tgggggggcc ctcatcgctg       1860
accgctgggt gataacagct gcccactgct tccaggagga cagcatggcc tccacggtgc       1920
tgtggaccgt gttcctgggc aaggtgtggc agaactcgcg ctggcctgga gaggtgtcct       1980
tcaaggtgag ccgcctgctc ctgcacccgt accacgaaga ggacagccat gactacgacg       2040
tggcgctgct gcagctcgac caccggtgg tgcgctcggc cgccgtgcgc ccgtctgcc        2100 tgcccgcgcg ctcccacttc ttcgagcccg gcctgcactg ctggattacg ggctggggcg       2160
ccttgcgcga gggcgcccta cgggcggatg ctgtggccct attttatgga tggagaaacc       2220
aaggctcaga gacatgttgc tgccccatca gcaacgctct gcagaaagtg gatgtgcagt       2280
tgatcccaca ggacctgtgc agcgaggtct atcgctacca ggtgacgcca cgcatgctgt       2340
gtgccggcta ccgcaagggc aagaaggatg cctgtcaggg tgactcaggt ggtccgctgg       2400
tgtgcaaggc actcagtggc cgctggttcc tggcggggct ggtcagctgg ggcctgggct       2460
gtggccggcc taactacttc ggcgtctaca cccgcatcac aggtgtgatc agctggatcc       2520
agcaagtggt gacctgagga actgccccc tgcaaagcag ggcccacctc ctggactcag       2580
agagcccagg gcaactgcca agcagggga caagtattct ggcggggggt gggggagaga       2640
gcaggccctg tggtggcagg aggtggcatc ttgtctcgtc cctgatgtct gctccagtga       2700
tggcaggagg atggagaagt gccagcagct gggggtcaag acgtccctg aggacccagg        2760 cccacaccca gccttctgc ctcccaattc tctctcctcc gtccccttcc tccactgctg        2820
cctaatgcaa ggcagtggct cagcagcaag aatgctggtt ctacatcccg aggagtgtct       2880
gaggtgcgcc ccactctgta cagaggctgt ttgggcagcc ttgcctccag agagcagatt       2940
ccagcttcgg aagccctgg tctaacttgg gatctgggaa tggaaggtgc tcccatcgga        3000
ggggaccctc agagccctgg agactgccag gtgggcctgc tgccactgta agccaaaagg       3060
```

-continued

```
tggggaagtc ctgactccag ggtccttgcc ccacccctgc ctgccacctg ggccctcaca     3120
gcccagaccc tcactgggag gtgagctcag ctgccctttg gaataaagct gcctgatcca     3180
aaaaaaaaaa aaaaaa                                                     3196

<210> SEQ ID NO 4
<211> LENGTH: 3196
<212> TYPE: DNA
<213> ORGANISM: Homo sapiens

<400> SEQUENCE: 4
ggacaaacag aggctcctga ggcctgtgtg caggcccggc acctatctgc cgctcccaaa       60
ggatgcccgt ggccgaggcc ccccaggtgg ctggcgggca gggggacgga ggtgatggcg      120
aggaagcgga gccggagggg atgttcaagg cctgtgagga ctccaagaga aaagcccggg      180
gctacctccg cctggtgccc ctgtttgtgc tgctggccct gctcgtgctg gcttcggcgg      240
gggtgctact ctggtatttc ctagggtaca aggcggaggt gatggtcagc caggtgtact      300
caggcagtct gcgtgtactc aatcgccact tctcccagga tcttacccgc cgggaatcta      360
gtgccttccg cagtgaaacc gccaaagccc agaagatgct caaggagctc atcaccagca      420
cccgcctggg aacttactac aactccagct ccgtctattc ctttggggag ggacccctca      480
cctgcttctt ctggttcatt ctccaaatcc ccgagcaccg ccggctgatg ctgagccccg      540
aggtggtgca ggcactgctg gtggaggagc tgctgtccac agtcaacagc tcggctgccg      600
tcccctacag ggccgagtac gaagtggacc ccgagggcct agtgatcctg aagccagtg       660 tgaaagacat agctgcattg aattccacgc tgggttgtta ccgctacagc tacgtgggcc      720
agggccaggt cctccggctg aagggggcctg accacctggc ctccagctgc ctgtggcacc      780
tgcagggccc caaggacctc atgctcaaac tccggctgga gtggacgctg gcagagtgcc      840
gggaccgact ggccatgtat gacgtggccg ggcccctgga agagggctc atcacctcgg      900 tgtacggctg cagccgccag gagccgtgg tggaggttct ggcgtcgggg gccatcatgg      960
cggtcgtctg gaagaagggc ctgcacagct actacgaccc cttcgtgctc tccgtgcagc     1020
cggtggtctt ccaggcctgt gaagtgaacc tgacgctgga caacaggctc gactcccagg     1080
gcgtcctcag cacccgtac ttccccaget actactcgcc ccaaacccac tgctcctggc     1140
acctcacggt gccctctctg gactacggct tggccctctg gtttgatgcc tatgcactga     1200
ggaggcagaa gtatgatttg ccgtgcaccc agggccagtg gacgatccag aacaggaggc     1260
tgtgtggctt gcgcatcctg cagccctacg ccgagaggat ccccgtggtg gccacggccg     1320
ggatcaccat caacttcacc tcccagatct ccctcaccgg gcccggtgtg cgggtgcact     1380
atggcttgta caaccagtcg gacccctgcc ctggagagtt cctctgttct gtgaatggac     1440
tctgtgtccc tgcctgtgat ggggtcaagg actgccccaa cggcctggat gagagaaact     1500
gcgtttgcag agccacattc cagtgcaaag aggacagcac atgcatctca ctgcccaagg     1560
tctgtgatgg gcagcctgat tgtctcaacg gcagcgacga gagcagtgc caggaagggg     1620 tgccatgtgg gacattcacc ttccagtgtg aggaccggag ctgcgtgaag aagcccaacc     1680
cgcagtgtga tgggcggccc gactgcaggg acggctcgga tgaggagcac tgtgactgtg     1740
gcctccaggg cccctccagc cgcattgttg gtggagctgt gtcctccgag ggtgagtggc     1800
catggcaggc cagcctccag gttcggggtc gacacatctg tggggggggcc ctcatcgctg     1860 accgctgggt gataacagct gcccactgct tccaggagga cagcatggcc tccacggtgc     1920
tgtggaccgt gttcctgggc aaggtgtggc agaactcgcg ctggcctgga gaggtgtcct     1980
```

-continued

```
tcaaggtgag ccgcctgctc ctgcacccgt accacgaaga ggacagccat gactacgacg      2040
tggcgctgct gcagctcgac cacccggtgg tgcgctcggc cgccgtgcgc cccgtctgcc      2100
tgcccgcgcg ctcccacttc ttcgagcccg gcctgcactg ctggattacg ggctggggcg      2160
ccttgcgcga gggcgcccta cgggcggatg ctgtggccct attttatgga tggagaaacc      2220
aaggctcaga gacatgttgc tgccccatca gcaacgctct gcagaaagtg gatgtgcagt      2280
tgatcccaca ggacctgtgc agcgaggtct atcgctacca agtgacgcca cgcatgctgt      2340
gtgccggcta ccgcaagggc aagaaggatg cctgtcaggg tgactcaggt ggtccgctgg      2400
tgtgcaaggc actcagtggc cgctggttcc tggcgggggct ggtcagctgg ggcctgggct      2460
gtggccggcc taactacttc ggcgtctaca cccgcatcac aggtgtgatc agctggatcc      2520
agcaagtggt gacctgagga actgcccccc tgcaaagcag ggcccacctc ctggactcag      2580
agagcccagg gcaactgcca agcaggggga caagtattct ggcggggggt gggggagaga      2640
gcaggccctg tggtggcagg aggtggcatc ttgtctcgtc cctgatgtct gctccagtga      2700
tggcaggagg atggagaagt gccagcagct gggggtcaag acgtcccctg aggacccagg      2760
cccacaccca gcccttctgc ctcccaattc tctctcctcc gtcccccttcc tccactgctg      2820 cctaatgcaa ggcagtggct cagcagcaag aatgctggtt ctacatcccg aggagtgtct      2880
gaggtgcgcc ccactctgta cagaggctgt ttgggcagcc ttgcctccag agagcagatt      2940
ccagcttcgg aagcccctgg tctaacttgg gatctgggaa tggaaggtgc tcccatcgga      3000
ggggaccctc agagccctgg agactgccag gtgggcctgc tgccactgta agccaaaagg      3060
tggggaagtc ctgactccag ggtccttgcc ccaccccctgc ctgccacctg ggccctcaca      3120
gcccagaccc tcactgggag gtgagctcag ctgcccttttg gaataaagct gcctgatcca      3180
aaaaaaaaaa aaaaaa                                                      3196
```

<210> SEQ ID NO 5
<211> LENGTH: 274
<212> TYPE: PRT
<213> ORGANISM: Homo sapiens

<400> SEQUENCE: 5

```
Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
                20                  25                  30

Gly Asp Thr Tyr Pro Ser Asn Asp Arg Cys Cys His Glu Cys Arg Pro
            35                  40                  45

Gly Asn Gly Met Val Ser Arg Cys Ser Arg Ser Gln Asn Thr Val Cys
        50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
```

-continued

```
145              150              155              160

Ser Ser Asp Ala Ile Cys Glu Asp Arg Asp Pro Pro Ala Thr Gln Pro
                165              170              175

Gln Glu Thr Gln Gly Pro Pro Ala Arg Pro Ile Thr Val Gln Pro Thr
            180              185              190

Glu Ala Trp Pro Arg Thr Ser Gln Gly Pro Ser Thr Arg Pro Val Glu
        195              200              205

Val Pro Gly Gly Arg Ala Val Ala Ala Ile Leu Gly Leu Gly Leu Val
    210              215              220

Leu Gly Leu Leu Gly Pro Leu Ala Ile Leu Leu Ala Leu Tyr Leu Leu
225              230              235              240

Arg Arg Asp Gln Arg Leu Pro Pro Asp Ala His Lys Pro Pro Ser Phe
            245              250              255

Arg Thr Pro Ile Gln Glu Glu Gln Ala Asp Ala His Ser Thr Leu Ala
        260              265              270

Lys Ile
```

```
<210> SEQ ID NO 6
<211> LENGTH: 1201
<212> TYPE: DNA
<213> ORGANISM: Homo sapiens

<400> SEQUENCE: 6
aatattagag tctcaacccc caataaatat aggactggag atgtctgagg ctcattctgc      60
cctcgagccc accgggaacg aaagagaagc tctatctccc ctccaggagc ccagctatga     120
actccttctc cacaagcgcc ttcggtccag ttgccttctc cctggggctg ctcctggtgt     180
tgcctgctgc cttccctgcc ccagtacccc caggagaaga ttccaaagat gtagccgccc     240
cacacagaca gccactcacc tcttcagaac gaattgacaa acaaattcgg tacatcctcg     300
acggcatctc agccctgaga aaggagacat gtaacaagag taacatgtgt gaaagcagca     360
aagaggcact ggcagaaaac aacctgaacc ttccaaagat ggctgaaaaa gatggatgct     420
tccaatctgg attcaatgag gagacttgcc tggtgaaaat catcactggt cttttggagt     480
ttgaggtata cctagagtac ctccagaaca gatttgagag tagtgaggaa caagccagag     540
ctgtgcagat gagtacaaaa gtcctgatcc agttcctgca gaaaaaggca aagaatctag     600
atgcaataac caccctgac ccaaccacaa atgccagcct gctgacgaag ctgcaggcac     660
agaaccagtg gctgcaggac atgacaactc atctcattct gcgcagcttt aaggagttcc     720
tgcagtccag cctgagggct cttcggcaaa tgtagcatgg gcacctcaga ttgttgttgt     780
taatgggcat tccttcttct ggtcagaaac ctgtccactg ggcacagaac ttatgttgtt     840
ctctatggag aactaaaagt atgagcgtta ggacactatt ttaattattt ttaatttatt     900
aatatttaaa tatgtgaagc tgagttaatt tatgtaagtc atatttatat ttttaagaag     960
taccacttga aacattttat gtattagttt tgaaataata atggaaagtg gctatgcagt    1020
ttgaatatcc tttgtttcag agccagatca tttcttggaa agtgtaggct tacctcaaat    1080
aaatggctaa cttatacata tttttaaaga aatatttata ttgtatttat ataatgtata    1140
aatggttttt ataccaataa atggcatttt aaaaaattca gcaaaaaaaa aaaaaaaaa    1200 a                                                                     1201
```

```
<210> SEQ ID NO 7
<211> LENGTH: 468
<212> TYPE: PRT
```

```
<213> ORGANISM: Homo sapiens

<400> SEQUENCE: 7

Met Leu Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
            35                  40                  45

Gly Val Glu Pro Glu Asp Asn Ala Thr Val His Trp Val Leu Arg Lys
        50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
            115                 120                 125

Asn Val Val Cys Glu Trp Gly Pro Arg Ser Thr Pro Ser Leu Thr Thr
        130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
            195                 200                 205

Gln Gly Cys Gly Ile Leu Gln Pro Asp Pro Pro Ala Asn Ile Thr Val
        210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
            275                 280                 285

Val Val Gln Leu Arg Ala Gln Glu Glu Phe Gly Gln Gly Glu Trp Ser
        290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
            340                 345                 350

Ser Leu Pro Val Gln Asp Ser Ser Ser Val Pro Leu Pro Thr Phe Leu
            355                 360                 365

Val Ala Gly Gly Ser Leu Ala Phe Gly Thr Leu Leu Cys Ile Ala Ile
        370                 375                 380

Val Leu Arg Phe Lys Lys Thr Trp Lys Leu Arg Ala Leu Lys Glu Gly
385                 390                 395                 400
```

-continued

```
Lys Thr Ser Met His Pro Pro Tyr Ser Leu Gly Gln Leu Val Pro Glu
                405             410             415

Arg Pro Arg Pro Thr Pro Val Leu Val Pro Leu Ile Ser Pro Pro Val
            420             425             430

Ser Pro Ser Ser Leu Gly Ser Asp Asn Thr Ser Ser His Asn Arg Pro
            435             440             445

Asp Ala Arg Asp Pro Arg Ser Pro Tyr Asp Ile Ser Asn Thr Asp Tyr
    450             455             460

Phe Phe Pro Arg
465

<210> SEQ ID NO 8
<211> LENGTH: 918
<212> TYPE: PRT
<213> ORGANISM: Homo sapiens

<400> SEQUENCE: 8

Met Leu Thr Leu Gln Thr Trp Leu Val Gln Ala Leu Phe Ile Phe Leu
1               5               10              15

Thr Thr Glu Ser Thr Gly Glu Leu Leu Asp Pro Cys Gly Tyr Ile Ser
            20              25              30

Pro Glu Ser Pro Val Val Gln Leu His Ser Asn Phe Thr Ala Val Cys
            35              40              45

Val Leu Lys Glu Lys Cys Met Asp Tyr Phe His Val Asn Ala Asn Tyr
    50              55              60

Ile Val Trp Lys Thr Asn His Phe Thr Ile Pro Lys Glu Gln Tyr Thr
65              70              75              80

Ile Ile Asn Arg Thr Ala Ser Ser Val Thr Phe Thr Asp Ile Ala Ser
            85              90              95

Leu Asn Ile Gln Leu Thr Cys Asn Ile Leu Thr Phe Gly Gln Leu Glu
            100             105             110

Gln Asn Val Tyr Gly Ile Thr Ile Ile Ser Gly Leu Pro Pro Glu Lys
            115             120             125

Pro Lys Asn Leu Ser Cys Ile Val Asn Glu Gly Lys Lys Met Arg Cys
    130             135             140

Glu Trp Asp Gly Gly Arg Glu Thr His Leu Glu Thr Asn Phe Thr Leu
145             150             155             160

Lys Ser Glu Trp Ala Thr His Lys Phe Ala Asp Cys Lys Ala Lys Arg
            165             170             175

Asp Thr Pro Thr Ser Cys Thr Val Asp Tyr Ser Thr Val Tyr Phe Val
            180             185             190

Asn Ile Glu Val Trp Val Glu Ala Glu Asn Ala Leu Gly Lys Val Thr
            195             200             205

Ser Asp His Ile Asn Phe Asp Pro Val Tyr Lys Val Lys Pro Asn Pro
    210             215             220

Pro His Asn Leu Ser Val Ile Asn Ser Glu Glu Leu Ser Ser Ile Leu
225             230             235             240

Lys Leu Thr Trp Thr Asn Pro Ser Ile Lys Ser Val Ile Ile Leu Lys
            245             250             255

Tyr Asn Ile Gln Tyr Arg Thr Lys Asp Ala Ser Thr Trp Ser Gln Ile
            260             265             270

Pro Pro Glu Asp Thr Ala Ser Thr Arg Ser Ser Phe Thr Val Gln Asp
            275             280             285

Leu Lys Pro Phe Thr Glu Tyr Val Phe Arg Ile Arg Cys Met Lys Glu
    290             295             300
```

-continued

```
Asp Gly Lys Gly Tyr Trp Ser Asp Trp Ser Glu Glu Ala Ser Gly Ile
305                 310             315             320

Thr Tyr Glu Asp Arg Pro Ser Lys Ala Pro Ser Phe Trp Tyr Lys Ile
                325             330             335

Asp Pro Ser His Thr Gln Gly Tyr Arg Thr Val Gln Leu Val Trp Lys
            340             345             350

Thr Leu Pro Pro Phe Glu Ala Asn Gly Lys Ile Leu Asp Tyr Glu Val
            355             360             365

Thr Leu Thr Arg Trp Lys Ser His Leu Gln Asn Tyr Thr Val Asn Ala
        370             375             380

Thr Lys Leu Thr Val Asn Leu Thr Asn Asp Arg Tyr Leu Ala Thr Leu
385             390             395             400

Thr Val Arg Asn Leu Val Gly Lys Ser Asp Ala Ala Val Leu Thr Ile
                405             410             415

Pro Ala Cys Asp Phe Gln Ala Thr His Pro Val Met Asp Leu Lys Ala
            420             425             430

Phe Pro Lys Asp Asn Met Leu Trp Val Glu Trp Thr Thr Pro Arg Glu
            435             440             445

Ser Val Lys Lys Tyr Ile Leu Glu Trp Cys Val Leu Ser Asp Lys Ala
        450             455             460

Pro Cys Ile Thr Asp Trp Gln Gln Glu Asp Gly Thr Val His Arg Thr
465             470             475             480

Tyr Leu Arg Gly Asn Leu Ala Glu Ser Lys Cys Tyr Leu Ile Thr Val
                485             490             495

Thr Pro Val Tyr Ala Asp Gly Pro Gly Ser Pro Glu Ser Ile Lys Ala
            500             505             510

Tyr Leu Lys Gln Ala Pro Pro Ser Lys Gly Pro Thr Val Arg Thr Lys
            515             520             525

Lys Val Gly Lys Asn Glu Ala Val Leu Glu Trp Asp Gln Leu Pro Val
        530             535             540

Asp Val Gln Asn Gly Phe Ile Arg Asn Tyr Thr Ile Phe Tyr Arg Thr
545             550             555             560

Ile Ile Gly Asn Glu Thr Ala Val Asn Val Asp Ser Ser His Thr Glu
                565             570             575

Tyr Thr Leu Ser Ser Leu Thr Ser Asp Thr Leu Tyr Met Val Arg Met
            580             585             590

Ala Ala Tyr Thr Asp Glu Gly Gly Lys Asp Gly Pro Glu Phe Thr Phe
            595             600             605

Thr Thr Pro Lys Phe Ala Gln Gly Glu Ile Glu Ala Ile Val Val Pro
        610             615             620

Val Cys Leu Ala Phe Leu Leu Thr Thr Leu Leu Gly Val Leu Phe Cys
625             630             635             640

Phe Asn Lys Arg Asp Leu Ile Lys Lys His Ile Trp Pro Asn Val Pro
                645             650             655

Asp Pro Ser Lys Ser His Ile Ala Gln Trp Ser Pro His Thr Pro Pro
            660             665             670

Arg His Asn Phe Asn Ser Lys Asp Gln Met Tyr Ser Asp Gly Asn Phe
            675             680             685

Thr Asp Val Ser Val Val Glu Ile Glu Ala Asn Asp Lys Lys Pro Phe
        690             695             700

Pro Glu Asp Leu Lys Ser Leu Asp Leu Phe Lys Lys Glu Lys Ile Asn
705             710             715             720
```

```
Thr Glu Gly His Ser Ser Gly Ile Gly Gly Ser Ser Cys Met Ser Ser
                725             730             735

Ser Arg Pro Ser Ile Ser Ser Ser Asp Glu Asn Glu Ser Ser Gln Asn
            740             745             750

Thr Ser Ser Thr Val Gln Tyr Ser Thr Val Val His Ser Gly Tyr Arg
        755             760             765

His Gln Val Pro Ser Val Gln Val Phe Ser Arg Ser Glu Ser Thr Gln
    770             775             780

Pro Leu Leu Asp Ser Glu Gly Arg Pro Glu Asp Leu Gln Leu Val Asp
785             790             795             800

His Val Asp Gly Gly Asp Gly Ile Leu Pro Arg Gln Gln Tyr Phe Lys
            805             810             815

Gln Asn Cys Ser Gln His Glu Ser Ser Pro Asp Ile Ser His Phe Glu
            820             825             830

Arg Ser Lys Gln Val Ser Ser Val Asn Glu Glu Asp Phe Val Arg Leu
        835             840             845

Lys Gln Gln Ile Ser Asp His Ile Ser Gln Ser Cys Gly Ser Gly Gln
    850             855             860

Met Lys Met Phe Gln Glu Val Ser Ala Ala Asp Ala Phe Gly Pro Gly
865             870             875             880

Thr Glu Gly Gln Val Glu Arg Phe Glu Thr Val Gly Met Glu Ala Ala
            885             890             895

Thr Asp Glu Gly Met Pro Lys Ser Tyr Leu Pro Gln Thr Val Arg Gln
            900             905             910

Gly Gly Tyr Met Pro Gln
        915
```

```
<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Asn Tyr Met Ile
1               5

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asp Leu Tyr Tyr Tyr Ala Gly Asp Thr Tyr Tyr Ala Asp Ser Val Lys
1               5               10              15

Gly

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11
```

-continued

```
Trp Ala Asp Asp His Pro Pro Trp Ile Asp Leu
1               5               10

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Ala Ser Gln Gly Ile Ser Ser Trp Leu Ala
1               5               10

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Ala Ser Thr Leu Glu Ser
1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Gln Ser Trp Leu Gly Gly Ser
1               5

<210> SEQ ID NO 15
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Ser Asn
            20                  25                  30

Tyr Met Ile Trp Val Arg Gln Ala Pro Gly Lys Gly Leu Glu Trp Val
        35                  40                  45

Ser Asp Leu Tyr Tyr Ala Gly Asp Thr Tyr Tyr Ala Asp Ser Val
    50                  55                  60

Lys Gly Arg Phe Thr Met Ser Arg Asp Ile Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Arg Trp Ala Asp Asp His Pro Pro Trp Ile Asp Leu Trp Gly Arg
            100                 105                 110

Gly Thr Leu Val Thr Val Ser Ser Ala Ser Thr Lys Gly Pro Ser Val
```

-continued

```
              115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
                195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Tyr Ile
                245                 250                 255

Thr Arg Glu Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 16
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

```
Asp Ile Gln Met Thr Gln Ser Pro Ser Thr Leu Ser Ala Ser Val Gly
1               5                   10                  15
```

-continued

```
Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Val Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Ser Trp Leu Gly Gly Ser
            85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210
```

TREATMENT OF DIURETIC RESISTANT HEART FAILURE PATIENTS HAVING AT LEAST ONE COPY OF THE TMPRSS6 rs855791 ALLELE

CROSS-REFERENCE TO RELATED APPLICATIONS

This application is a continuation of U.S. application Ser. No. 16/482,038, filed Jul. 30, 2019, which is a 35 U.S.C. 371 national stage filing of International Application No. PCT/US2018/016508, filed on Feb. 1, 2018, which claims priority to U.S. Application No. 62/453,257 filed on Feb. 1, 2017. The contents of the aforementioned applications are hereby incorporated by reference in their entireties.

STATEMENT REGARDING FEDERALLY SPONSORED RESEARCH OR DEVELOPMENT

This invention was made with government support under grants 5R01HL128973 and 4K23HL114868 awarded by the National Institutes of Health. The government has certain rights in the invention.

STATEMENT REGARDING JOINT RESEARCH AGREEMENT

This invention was made under a Joint Research Agreement by and among Yale University, MedImmune Ltd., AstraZeneca Pharmaceuticals LP, and Corvidia Therapeutics, Inc.

SEQUENCE LISTING

The instant application contains a Sequence Listing which has been submitted via XML format via USPTO patent electronic filing system and is hereby incorporated herein by reference in its entirety. Said XML file, created on Nov. 21, 2025, is named "210091US03_sequence_listing.xml", and is 29,694 bytes in size.

BACKGROUND

Renal injury is often observed in heart failure, and heart failure is often observed in renal disease. The term cardiorenal syndrome ("CRS") encompasses a variety of clinical conditions in which dysfunction of the heart, kidney, or both, leads to accelerated failure of both organs. Evidence of this adverse organ crosstalk portends a high degree of morbidity and mortality. Despite its dire clinical implications, the mechanistic underpinnings of CRS are only now being elucidated.

There is a need for new methods of treating renal injury and renal impairment in heart failure patients. There is also a need for new methods of detecting cardiorenal syndrome, for determining which cardiorenal patients will be responsive to treatment, and for monitoring efficacy of therapy.

Diuretics are a mainstay in the treatment of heart failure. However, certain patients are, or become, resistant to diuretics. There is a need for new methods of treating patients who require diuretics but are resistant to diuretics.

SUMMARY

As further described below in Example 1, consecutive heart failure ("HF") patients receiving high dose diuretic therapy at an outpatient treatment center were enrolled in a prospective observational study. Plasma levels of IL-6 were measured to query systemic associations of this pro-inflammatory cytokine with various disease parameters, and urine levels of IL-6 were measured to query IL-6 associations with local inflammation and neurohormonal activation at the level of renal tissues.

Urine IL-6 and plasma IL-6 levels were found to be only modestly correlated with one another.

Increases in urine levels of IL-6 were significantly correlated in these heart failure patients with measures of renal impairment, such as diuretic resistance, lower estimated glomerular filtration rate ("eGFR"), and increased tissue-level renin-angiotensin-aldosterone system ("RAAS") activation.

Although an inverse association between diuretic efficiency and plasma IL-6 was also observed, upon adjustment for eGFR, only urine IL-6 remained significantly associated with risk of low diuretic efficiency in these patients. Furthermore, when urine IL-6 and plasma IL-6 were both entered into a logistic regression model, only urine IL-6 remained associated with risk of low diuretic efficiency while plasma IL-6 showed no such association.

These data demonstrate that urine IL-6 level is a useful biomarker for renal inflammation, and can be used to gauge renal dysfunction in the setting of heart failure (cardiorenal syndrome). The data further suggest that serial measurements of urine IL-6 can be used to measure the renal benefits of treatments administered to patients with heart failure, notably heart failure patients with cardiorenal syndrome.

The urine IL-6 data, and to some extent the plasma IL-6 data, also predict that treatment with an IL 6 antagonist should be effective to reduce renal inflammation in heart failure patients, that is, to treat renal symptoms of cardiorenal syndrome.

However, because infection is often a precipitating cause of acute decompensation in heart failure patients, it is important to limit anti-cytokine and other immunosuppressive therapies to those heart failure patients who are likely to respond with improved renal and/or cardiac function. The cost of chronic IL-6 antagonist therapy also militates for limiting treatment to those heart failure patients who are likely to respond with improved renal and/or cardiac function.

Analysis was expanded to 129 patients, and further assessed each patient's genotype at the rs855791 single nucleotide polymorphism ("SNP") in transmembrane protease serine 6 ("TMPRSS6").

Urine levels of IL-6 were inversely correlated with diuretic efficiency only in the patients having at least one copy of the major allele of the TMPRSS6 rs855791 SNP (AG and GG); urine levels of IL-6 were not significantly correlated with diuretic efficiency in patients homozygous for the minor allele (AA). Plasma levels of IL-6 correlated inversely with diuretic efficiency only in the patients having at least one copy of the major allele of the TMPRSS6 rs855791 SNP; plasma levels of IL-6 were not significantly correlated with diuretic efficiency in patients homozygous for the minor allele.

These data suggested that diuretic resistance (low diuretic efficiency) in heart failure patients could be treated with an IL-6 antagonist, but only in those having at least one copy of the TMPRSS6 rs855791 major allele.

In mouse M1 CCD cells, which are genotypically analogous to human cells homozygous for the TMPRSS6 rs855791 major allele, the addition of IL-6 correlated with the expression of ion transporters, NKCC2, ENaC-beta, and NCC. Increased expression of these ion transporters provides a putative mechanism for IL-6 mediated diuretic resistance.

Because the IL-6 mediated increase in expression of ion transporters is not known to be linked to hepcidin expression, these data suggested that IL-6 antagonism could also be effective in treating diuretic resistance in patients homozygous for the TMPRSS6 rs855791 minor allele.

Secondary analysis of data from two additional large heart failure clinical trials confirmed the association of diuretic resistance with IL-6 level (Example 5), independently of TMPRSS6 rs855791 genotype (Example 6), providing evidence that IL-6 antagonism should also be effective in treating diuretic resistance in patients homozygous for the TMPRSS6 rs855791 minor allele.

Accordingly, in a first aspect, methods are provided for treating a patient who requires diuresis but is resistant to diuretics. The methods comprise administering, in combination with a diuretic, a therapeutically effective amount of an IL-6 antagonist to the patient.

In some embodiments, the patient has elevated pre-treatment plasma IL-6 levels. In certain embodiments, the patient has a pre-treatment plasma IL-6 level of greater than 2 pg/mL. In certain embodiments, the patient has a pre-treatment IL-6 level of greater than 3 pg/mL. In certain embodiments, the patient has a pre-treatment IL-6 level of greater than 5 pg/mL. In certain embodiments, the patient has a pre-treatment IL-6 level of greater than 10 pg/mL.

In some embodiments, the patient has a diuretic efficiency of less than 500. In some embodiments, the patient has a diuretic efficiency of less than 200. In some embodiments, the patient has a diuretic efficiency of less than 150. In some embodiments, the patient has a diuretic efficiency of less than 100.

In some embodiments, the patient has diuretic resistant heart failure. In certain embodiments, the patient has acute heart failure. In certain embodiments, the patient has chronic heart failure.

In some embodiments, the patient has cardiorenal syndrome. In some of these embodiments, the patient has cardiorenal syndrome type 4.

In some embodiments, the patient has kidney disease. In certain embodiments, the patient has hepatorenal syndrome.

In some embodiments, the patient has at least one copy of the TMPRSS6 rs855791 major allele.

In certain embodiments, the IL-6 antagonist is an anti-IL-6 antibody, or antigen-binding fragment or derivative thereof. In particular embodiments, the anti-IL-6 antibody or antigen-binding fragment or derivative has a $K_D$ for binding human IL-6 of less than 100 nM, less than 50 nM, less than 10 nM, even less than 1 nM.

In certain embodiments, the anti-IL-6 antibody or antigen-binding fragment or derivative has an elimination half-life following intravenous administration of at least 7 days, at least 14 days, at least 21 days, or at least 30 days.

In certain embodiments, the IL-6 antagonist is a full-length monoclonal anti-IL-6 antibody. In particular embodiments, the antibody is an IgG1 or IgG4 antibody. In certain embodiments, the antibody is an IgG1 antibody.

In certain embodiments, the anti-IL-6 antibody or antigen-binding fragment or derivative is fully human. In certain embodiments, the anti-IL-6 antibody or antigen-binding fragment or derivative is humanized.

In certain embodiments, the anti-IL-6 antibody or antigen-binding fragment or derivative comprises all six variable region CDRs of MED5117. In specific embodiments, the antibody comprises the VH and VL of MED5117. In particular embodiments, the antibody is MED5117.

In certain embodiments, the anti-IL-6 antibody or antigen-binding fragment or derivative comprises all six variable region CDRs of an antibody selected from the group consisting of siltuximab, gerilimzumab, sirukumab, clazakizumab, olokizumab, elsilimomab, VX30 (VOP-R003; Vaccinex), EB-007 (EBI-029; Eleven Bio), ARGX-109 (ArGEN-X), FM101 (Femta Pharmaceuticals, Lonza) and ALD518/BMS-945429 (Alder Biopharmaceuticals, Bristol-Myers Squibb). In certain embodiments, the anti-IL-6 antibody or antigen-binding fragment or derivative comprises the heavy chain V region and light chain V region from an antibody selected from the group consisting of siltuximab, gerilimzumab, sirukumab, clazakizumab, olokizumab, VX30 (VOP-R003; Vaccinex), EB-007 (EBI-029; Eleven Bio), ARGX-109 (ArGEN-X), FM101 (Femta Pharmaceuticals, Lonza) and ALD518/BMS-945429 (Alder Biopharmaceuticals, Bristol-Myers Squibb). In particular embodiments, the anti-IL-6 antibody or antigen-binding fragment or derivative is an antibody selected from the group consisting of siltuximab, gerilimzumab, sirukumab, clazakizumab, olokizumab, VX30 (VOP-R003; Vaccinex), EB-007 (EBI-029; Eleven Bio), ARGX-109 (ArGEN-X), FM101 (Femta Pharmaceuticals, Lonza) and ALD518/BMS-945429 (Alder Biopharmaceuticals, Bristol-Myers Squibb).

In certain embodiments, the IL-6 antagonist is a single domain antibody, a Vim Nanobody, an Fab, or a scFv.

In certain embodiments, the IL-6 antagonist is an anti-IL-6R antibody, or antigen-binding fragment or derivative thereof. In certain embodiments, the anti-IL-6R antibody, antigen-binding fragment, or derivative comprises the 6 CDRs of tocilizumab or vobarilizumab.

In certain embodiments, the IL-6 antagonist is a JAK inhibitor. In certain embodiments, the JAK inhibitor is selected from the group consisting of tofacitinib (Xeljanz), decernotinib, ruxolitinib, upadacitinib, baricitinib, filgotinib, lestaurtinib, pacritinib, peficitinib, INCB-039110, ABT-494, INCB-047986 and AC-410.

In certain embodiments, the IL-6 antagonist is a STAT3 inhibitor.

In certain embodiments, the IL-6 antagonist is administered parenterally. In particular embodiments, the IL-6 antagonist is administered subcutaneously.

In certain embodiments, the IL-6 antagonist is administered orally.

In certain embodiments, the IL-6 antagonist is administered at a dose, on a schedule, and for a period sufficient to increase diuretic efficiency. In certain embodiments, the IL-6 antagonist is administered at a dose, on a schedule, and for a period sufficient to increase diuretic efficiency to normal levels. In certain embodiments, the IL-6 antagonist is administered at a dose, on a schedule, and for a period sufficient to increase eGFR. In particular embodiments, the IL-6 antagonist is administered at a dose, on a schedule, and for a period sufficient to increase eGFR to normal levels.

In certain embodiments, the method further comprises the subsequent step of determining the level of IL-6 in urine, determining the level of IL-6 in plasma, or determining the level of IL-6 in urine and in plasma. In particular embodiments, the method further comprises a final step of adjusting the dose of IL-6 antagonist for subsequent administration based on IL-6 level determined in the immediately preceding step.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 4B showing the expression of ENaC-beta after the treatment with IL-6 and/or Ruxolitinib; and FIG. 4C showing the expression of NCC after the treatment with IL-6 and/or Ruxolitinib.

FIG. 5B showing the expression of ENaC-beta after the treatment with IL-6 and/or Spironolactone; and FIG. 5C showing the expression of NCC after the treatment with IL-6 and/or Spironolactone.

FIGS. 10A and 10B show the Kaplan-Meier survival curve by tertiles of IL-6, with FIG. 10A showing the all-cause mortality and/or rehospitalization for heart failure at 2 years and FIG. 10B showing all-cause mortality at 2 years.

DETAILED DESCRIPTION

Definitions

Figure 1A:
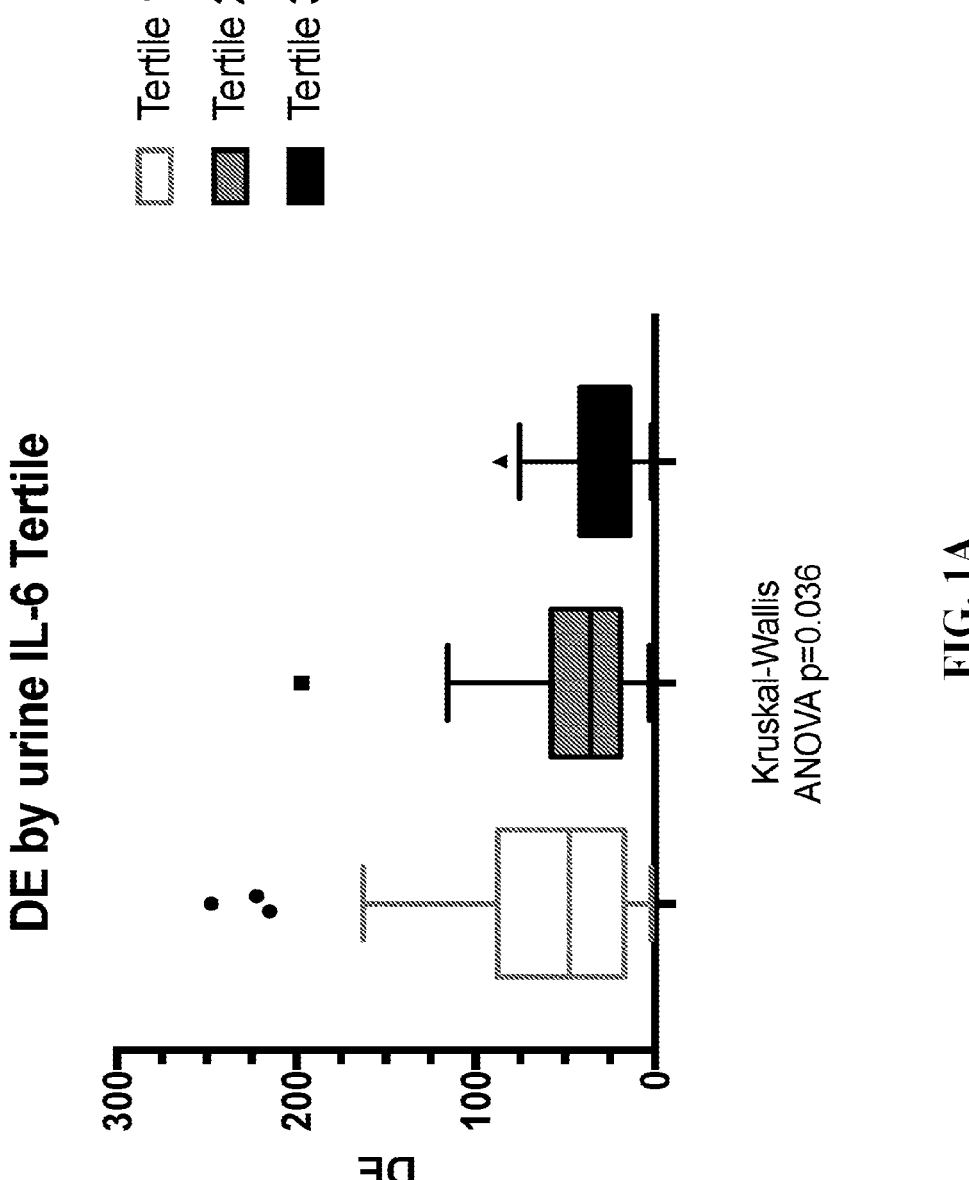
FIG. 1A is a bar graph showing diuretic efficiency ("DE") by tertiles of urine IL-6 in 129 heart failure ("HF") patients receiving high dose diuretic therapy who were enrolled in the study described in Example 1 herein. Whiskers extend from the 10$^{th}$ to 90$^{th}$ percentile.

Unless defined otherwise, all technical and scientific terms used herein have the same meaning as commonly understood by one of ordinary skill in the art to which the invention pertains. It is also to be understood that the terminology used herein is for the purpose of describing particular embodiments only, and is not intended to be limiting.

By "transmembrane protease serine 6 (TMPRSS6) polypeptide" is meant a polypeptide or fragment thereof having at least about 85% or greater amino acid identity to the amino acid sequence provided at NCBI Accession No. NP_001275929 and having serine proteinase activity. The TMPRSS6 polypeptide, also known as Matriptase-2 (MT2), cleaves hemojuvelin and inhibits bone morphogenetic protein signaling. An exemplary TMPRSS6 amino acid sequence having an alanine at position 736 (736A) is provided below:

(SEQ ID NO: 1)

```
  1 MPVAEAPQVA GGQGDGGDGE EAEPEGMFKA CEDSKRKARG YLRLVPLFVL LALLVLASAG

61 VLLWYFLGYK AEVMVSQVYS GSLRVLNRHF SQDLTRRESS AFRSETAKAQ KMLKELITST

121 RLGTYYNSSS VYSFGEGPLT CFFWFILQIP EHRRLMLSPE VVQALLVEEL LSTVNSSAAV

181 PYRAEYEVDP EGLVILEASV KDIAALNSTL GCYRYSYVGQ GQVLRLKGPD HLASSCLWHL

241 QGPKDLMLKL RLEWTLAECR DRLAMYDVAG PLEKRLITSV YGCSRQEPVV EVLASGAIMA

301 VVWKKGLHSY YDPFVLSVQP VVFQACEVNL TLDNRLDSQG VLSTPYFPSY YSPQTHCSWH
```

```
                                   -continued
361 LTVPSLDYGL ALWFDAYALR RQKYDLPCTQ GQWTIQNRRL CGLRILQPYA ERIPVVATAG

421 ITINFTSQIS LTGPGVRVHY GLYNQSDPCP GEFLCSVNGL CVPACDGVKD CPNGLDERNC

481 VCRATFQCKE DSTCISLPKV CDGQPDCLNG SDEEQCQEGV PCGTFTFQCE DRSCVKKPNP

541 QCDGRPDCRD GSDEEHCDCG LQGPSSRIVG GAVSSEGEWP WQASLQVRGR HICGGALIAD

601 RWVITAAHCF QEDSMASTVL WTVFLGKVWQ NSRWPGEVSF KVSRLLLHPY HEEDSHDYDV

661 ALLQLDHPVV RSAAVRPVCL PARSHFFEPG LHCWITGWGA LREGALRADA VALFYGWRNQ

721 GSETCCCPIS NALQKADVQL IPQDLCSEVY RYQVTPRMLC AGYRKGKKDA CQGDSGGPLV

781 CKALSGRWFL AGLVSWGLGC GRPNYFGVYT RITGVISWIQ QVVT
```

An exemplary TMPRSS6 amino acid sequence having a [15] valine at position 736 (736V) is provided below:

```
                                                                   (SEQ ID NO: 2)
  1 MPVAEAPQVA GGQGDGGDGE EAEPEGMFKA CEDSKRKARG YLRLVPLFVL LALLVLASAG

61 VLLWYFLGYK AEVMVSQVYS GSLRVLNRHF SQDLTRRESS AFRSETAKAQ KMLKELITST

121 RLGTYYNSSS VYSFGEGPLT CFFWFILQIP EHRRLMLSPE VVQALLVEEL LSTVNSSAAV

181 PYRAEYEVDP EGLVILEASV KDIAALNSTL GCYRYSYVGQ GQVLRLKGPD HLASSCLWHL

24 QGPKDLMLKL RLEWTLAECR DRLAMYDVAG PLEKRLITSV YGCSRQEPVV EVLASGAIMA

30 VVWKKGLHSY YDPFVLSVQP VVFQACEVNL TLDNRLDSQG VLSTPYFPSY YSPQTHCSWH

36 LTVPSLDYGL ALWFDAYALR RQKYDLPCTQ GQWTIQNRRL CGLRILQPYA ERIPVVATAG

42 ITINFTSQIS LTGPGVRVHY GLYNQSDPCP GEFLCSVNGL CVPACDGVKD CPNGLDERNC

48 VCRATFQCKE DSTCISLPKV CDGQPDCLNG SDEEQCQEGV PCGTFTFQCE DRSCVKKPNP

54 QCDGRPDCRD GSDEEHCDCG LQGPSSRIVG GAVSSEGEWP WQASLQVRGR HICGGALIAD

60 RWVITAAHCF QEDSMASTVL WTVFLGKVWQ NSRWPGEVSF KVSRLLLHPY HEEDSHDYDV

66 ALLQLDHPVV RSAAVRPVCL PARSHFFEPG LHCWITGWGA LREGALRADA VALFYGWRNQ

72 GSETCCCPIS NALQKVDVQL IPQDLCSEVY RYQVTPRMLC AGYRKGKKDA CQGDSGGPLV

78 CKALSGRWFL AGLVSWGLGC GRPNYFGVYT RITGVISWIQ QVVT
```

By "TMPRSS6 nucleic acid molecule" is meant a polynucleotide encoding a TMPRSS6 polypeptide (Matriptase-2; MT2). An exemplary TMPRSS6 nucleic acid molecule sequence is provided at NCBI Accession No. NM_001289000. A TMPRSS6 nucleic acid sequence having a G at nucleotide position 2321 ("G allele"; "major allele") is provided below:

```
                                                                   (SEQ ID NO: 3)
  1 GGACAAACAG AGGCTCCTGA GGCCTGTGTG CAGGCCCGGC ACCTATCTGC CGCTCCCAAA

61 GGATGCCCGT GGCCGAGGCC CCCCAGGTGG CTGGCGGGCA GGGGGACGGA GGTGATGGCG

121 AGGAAGCGGA GCCGGAGGGG ATGTTCAAGG CCTGTGAGGA CTCCAAGAGA AAAGCCCGGG

181 GCTACCTCCG CCTGGTGCCC CTGTTTGTGC TGCTGGCCCT GCTCGTGCTG GCTTCGGCGG

241 GGGTGCTACT CTGGTATTTC CTAGGGTACA AGGCGGAGGT GATGGTCAGC CAGGTGTACT

301 CAGGCAGTCT GCGTGTACTC AATCGCCACT TCTCCCAGGA TCTTACCCGC CGGGAATCTA

361 GTGCCTTCCG CAGTGAAACC GCCAAAGCCC AGAAGATGCT CAAGGAGCTC ATCACCAGCA

421 CCCGCCTGGG AACTTACTAC AACTCCAGCT CCGTCTATTC CTTTGGGGAG GGACCCCTCA

481 CCTGCTTCTT CTGGTTCATT CTCCAAATCC CCGAGCACCG CCGGCTGATG CTGAGCCCCG
```

-continued

```
 541 AGGTGGTGCA GGCACTGCTG GTGGAGGAGC TGCTGTCCAC AGTCAACAGC TCGGCTGCCG

601 TCCCCTACAG GGCCGAGTAC GAAGTGGACC CCGAGGGCCT AGTGATCCTG GAAGCCAGTG

661 TGAAAGACAT AGCTGCATTG AATTCCACGC TGGGTTGTTA CCGCTACAGC TACGTGGGCC

721 AGGGCCAGGT CCTCCGGCTG AAGGGGCCTG ACCACCTGGC CTCCAGCTGC CTGTGGCACC

781 TGCAGGGCCC CAAGGACCTC ATGCTCAAAC TCCGGCTGGA GTGGACGCTG GCAGAGTGCC

841 GGGACCGACT GGCCATGTAT GACGTGGCCG GGCCCCTGGA GAAGAGGCTC ATCACCTCGG

901 TGTACGGCTG CAGCCGCCAG GAGCCCGTGG TGGAGGTTCT GGCGTCGGGG GCCATCATGG

961 CGGTCGTCTG GAAGAAGGGC CTGCACAGCT ACTACGACCC CTTCGTGCTC TCCGTGCAGC

1021 CGGTGGTCTT CCAGGCCTGT GAAGTGAACC TGACGCTGGA CAACAGGCTC GACTCCCAGG

1081 GCGTCCTCAG CACCCCGTAC TTCCCCAGCT ACTACTCGCC CCAAACCCAC TGCTCCTGGC

1141 ACCTCACGGT GCCCTCTCTG GACTACGGCT TGGCCCTCTG GTTTGATGCC TATGCACTGA

1201 GGAGGCAGAA GTATGATTTG CCGTGCACCC AGGGCCAGTG GACGATCCAG AACAGGAGGC

1261 TGTGTGGCTT GCGCATCCTG CAGCCCTACG CCGAGAGGAT CCCCGTGGTG GCCACGGCCG

1321 GGATCACCAT CAACTTCACC TCCCAGATCT CCCTCACCGG GCCCGGTGTG CGGGTGCACT

1381 ATGGCTTGTA CAACCAGTCG GACCCCTGCC CTGGAGAGTT CCTCTGTTCT GTGAATGGAC

1441 TCTGTGTCCC TGCCTGTGAT GGGGTCAAGG ACTGCCCCAA CGGCCTGGAT GAGAGAAACT

1501 GCGTTTGCAG AGCCACATTC CAGTGCAAAG AGGACAGCAC ATGCATCTCA CTGCCCAAGG

1561 TCTGTGATGG GCAGCCTGAT TGTCTCAACG GCAGCGACGA AGAGCAGTGC CAGGAAGGGG

1621 TGCCATGTGG GACATTCACC TTCCAGTGTG AGGACCGGAG CTGCGTGAAG AAGCCCAACC

1681 CGCAGTGTGA TGGGCGGCCC GACTGCAGGG ACGGCTCGGA TGAGGAGCAC TGTGACTGTG

1741 GCCTCCAGGG CCCCTCCAGC CGCATTGTTG GTGGAGCTGT GTCCTCCGAG GGTGAGTGGC

1801 CATGGCAGGC CAGCCTCCAG GTTCGGGGTC GACACATCTG TGGGGGGGCC CTCATCGCTG

1861 ACCGCTGGGT GATAACAGCT GCCCACTGCT TCCAGGAGGA CAGCATGGCC TCCACGGTGC

1921 TGTGGACCGT GTTCCTGGGC AAGGTGTGGC AGAACTCGCG CTGGCCTGGA GAGGTGTCCT

1981 TCAAGGTGAG CCGCCTGCTC CTGCACCCGT ACCACGAAGA GGACAGCCAT GACTACGACG

2041 TGGCGCTGCT GCAGCTCGAC CACCCGGTGG TGCGCTCGGC CGCCGTGCGC CCCGTCTGCC

2101 TGCCCGCGCG CTCCCACTTC TTCGAGCCCG GCCTGCACTG CTGGATTACG GGCTGGGGCG

2161 CCTTGCGCGA GGGCGCCCTA CGGGCGGATG CTGTGGCCCT ATTTTATGGA TGGAGAAACC

2221 AAGGCTCAGA GACATGTTGC TGCCCCATCA GCAACGCTCT GCAGAAAGTG GATGTGCAGT

2281 TGATCCCACA GGACCTGTGC AGCGAGGTCT ATCGCTACCA GGTGACGCCA CGCATGCTGT

2341 GTGCCGGCTA CCGCAAGGGC AAGAAGGATG CCTGTCAGGG TGACTCAGGT GGTCCGCTGG

2401 TGTGCAAGGC ACTCAGTGGC CGCTGGTTCC TGGCGGGGCT GGTCAGCTGG GGCCTGGGCT

2461 GTGGCCGGCC TAACTACTTC GGCGTCTACA CCCGCATCAC AGGTGTGATC AGCTGGATCC

2521 AGCAAGTGGT GACCTGAGGA ACTGCCCCCC TGCAAAGCAG GGCCCACCTC CTGGACTCAG

2581 AGAGCCCAGG GCAACTGCCA AGCAGGGGGA CAAGTATTCT GGCGGGGGGT GGGGGAGAGA

2641 GCAGGCCCTG TGGTGGCAGG AGGTGGCATC TTGTCTCGTC CCTGATGTCT GCTCCAGTGA

2701 TGGCAGGAGG ATGGAGAAGT GCCAGCAGCT GGGGGTCAAG ACGTCCCCTG AGGACCCAGG

2761 CCCACACCCA GCCCTTCTGC CTCCCAATTC TCTCTCCTCC GTCCCCTTCC TCCACTGCTG

2821 CCTAATGCAA GGCAGTGGCT CAGCAGCAAG AATGCTGGTT CTACATCCCG AGGAGTGTCT

2881 GAGGTGCGCC CCACTCTGTA CAGAGGCTGT TTGGGCAGCC TTGCCTCCAG AGAGCAGATT

2941 CCAGCTTCGG AAGCCCCTGG TCTAACTTGG GATCTGGGAA TGGAAGGTGC TCCCATCGGA
```

-continued

```
3001 GGGGACCCTC AGAGCCCTGG AGACTGCCAG GTGGGCCTGC TGCCACTGTA AGCCAAAAGG

3061 TGGGGAAGTC CTGACTCCAG GGTCCTTGCC CCACCCCTGC CTGCCACCTG GGCCCTCACA

3121 GCCCAGACCC TCACTGGGAG GTGAGCTCAG CTGCCCTTTG GAATAAAGCT GCCTGATCCA

3181 AAAAAAAAAA AAAAAA
```

A TMPRSS6 nucleic acid sequence having an A at nucleotide position 2321 is provided below:

```
                                                         (SEQ ID NO: 4)
   1 GGACAAACAG AGGCTCCTGA GGCCTGTGTG CAGGCCCGGC ACCTATCTGC CGCTCCCAAA

61 GGATGCCCGT GGCCGAGGCC CCCCAGGTGG CTGGCGGGCA GGGGGACGGA GGTGATGGCG

121 AGGAAGCGGA GCCGGAGGGG ATGTTCAAGG CCTGTGAGGA CTCCAAGAGA AAAGCCCGGG

181 GCTACCTCCG CCTGGTGCCC CTGTTTGTGC TGCTGGCCCT GCTCGTGCTG GCTTCGGCGG

241 GGGTGCTACT CTGGTATTTC CTAGGGTACA AGGCGGAGGT GATGGTCAGC CAGGTGTACT

301 CAGGCAGTCT GCGTGTACTC AATCGCCACT TCTCCCAGGA TCTTACCCGC CGGGAATCTA

361 GTGCCTTCCG CAGTGAAACC GCCAAAGCCC AGAAGATGCT CAAGGAGCTC ATCACCAGCA

421 CCCGCCTGGG AACTTACTAC AACTCCAGCT CCGTCTATTC CTTTGGGGAG GGACCCCTCA

481 CCTGCTTCTT CTGGTTCATT CTCCAAATCC CCGAGCACCG CCGGCTGATG CTGAGCCCCG

541 AGGTGGTGCA GGCACTGCTG GTGGAGGAGC TGCTGTCCAC AGTCAACAGC TCGGCTGCCG

601 TCCCCTACAG GGCCGAGTAC GAAGTGGACC CCGAGGGCCT AGTGATCCTG GAAGCCAGTG

661 TGAAAGACAT AGCTGCATTG AATTCCACGC TGGGTTGTTA CCGCTACAGC TACGTGGGCC

721 AGGGCCAGGT CCTCCGGCTG AAGGGGCCTG ACCACCTGGC CTCCAGCTGC CTGTGGCACC

781 TGCAGGGCCC CAAGGACCTC ATGCTCAAAC TCCGGCTGGA GTGGACGCTG GCAGAGTGCC

841 GGGACCGACT GGCCATGTAT GACGTGGCCG GGCCCCTGGA GAAGAGGCTC ATCACCTCGG

901 TGTACGGCTG CAGCCGCCAG GAGCCCGTGG TGGAGGTTCT GGCGTCGGGG GCCATCATGG

961 CGGTCGTCTG GAAGAAGGGC CTGCACAGCT ACTACGACCC CTTCGTGCTC TCCGTGCAGC

1021 CGGTGGTCTT CCAGGCCTGT GAAGTGAACC TGACGCTGGA CAACAGGCTC GACTCCCAGG

1081 GCGTCCTCAG CACCCCGTAC TTCCCCAGCT ACTACTCGCC CCAAACCCAC TGCTCCTGGC

1141 ACCTCACGGT GCCCTCTCTG GACTACGGCT TGGCCCTCTG GTTTGATGCC TATGCACTGA

1201 GGAGGCAGAA GTATGATTTG CCGTGCACCC AGGGCCAGTG GACGATCCAG AACAGGAGGC

1261 TGTGTGGCTT GCGCATCCTG CAGCCCTACG CCGAGAGGAT CCCCGTGGTG GCCACGGCCG

1321 GGATCACCAT CAACTTCACC TCCCAGATCT CCCTCACCGG GCCCGGTGTG CGGGTGCACT

1381 ATGGCTTGTA CAACCAGTCG GACCCCTGCC CTGGAGAGTT CCTCTGTTCT GTGAATGGAC

1441 TCTGTGTCCC TGCCTGTGAT GGGGTCAAGG ACTGCCCCAA CGGCCTGGAT GAGAGAAACT

1501 GCGTTTGCAG AGCCACATTC CAGTGCAAAG AGGACAGCAC ATGCATCTCA CTGCCCAAGG

1561 TCTGTGATGG GCAGCCTGAT TGTCTCAACG GCAGCGACGA AGAGCAGTGC CAGGAAGGGG

1621 TGCCATGTGG GACATTCACC TTCCAGTGTG AGGACCGGAG CTGCGTGAAG AAGCCCAACC

1681 CGCAGTGTGA TGGGCGGCCC GACTGCAGGG ACGGCTCGGA TGAGGAGCAC TGTGACTGTG

1741 GCCTCCAGGG CCCCTCCAGC CGCATTGTTG GTGGAGCTGT GTCCTCCGAG GGTGAGTGGC

1801 CATGGCAGGC CAGCCTCCAG GTTCGGGGTC GACACATCTG TGGGGGGGCC CTCATCGCTG

1861 ACCGCTGGGT GATAACAGCT GCCCACTGCT TCCAGGAGGA CAGCATGGCC TCCACGGTGC

1921 TGTGGACCGT GTTCCTGGGC AAGGTGTGGC AGAACTCGCG CTGGCCTGGA GAGGTGTCCT
```

-continued

```
1981  TCAAGGTGAG CCGCCTGCTC CTGCACCCGT ACCACGAAGA GGACAGCCAT GACTACGACG

2041  TGGCGCTGCT GCAGCTCGAC CACCCGGTGG TGCGCTCGGC CGCCGTGCGC CCCGTCTGCC

2101  TGCCCGCGCG CTCCCACTTC TTCGAGCCCG GCCTGCACTG CTGGATTACG GGCTGGGGCG

2161  CCTTGCGCGA GGGCGCCCTA CGGGCGGATG CTGTGGCCCT ATTTTATGGA TGGAGAAACC

2221  AAGGCTCAGA GACATGTTGC TGCCCCATCA GCAACGCTCT GCAGAAAGTG GATGTGCAGT

2281  TGATCCCACA GGACCTGTGC AGCGAGGTCT ATCGCTACCA AGTGACGCCA CGCATGCTGT

2341  GTGCCGGCTA CCGCAAGGGC AAGAAGGATG CCTGTCAGGG TGACTCAGGT GGTCCGCTGG

2401  TGTGCAAGGC ACTCAGTGGC CGCTGGTTCC TGGCGGGGCT GGTCAGCTGG GGCCTGGGCT

2461  GTGGCCGGCC TAACTACTTC GGCGTCTACA CCCGCATCAC AGGTGTGATC AGCTGGATCC

2521  AGCAAGTGGT GACCTGAGGA ACTGCCCCCC TGCAAAGCAG GGCCCACCTC CTGGACTCAG

2581  AGAGCCCAGG GCAACTGCCA AGCAGGGGGA CAAGTATTCT GGCGGGGGGT GGGGGAGAGA

2641  GCAGGCCCTG TGGTGGCAGG AGGTGGCATC TTGTCTCGTC CCTGATGTCT GCTCCAGTGA

2701  TGGCAGGAGG ATGGAGAAGT GCCAGCAGCT GGGGGTCAAG ACGTCCCCTG AGGACCCAGG

2761  CCCACACCCA GCCCTTCTGC CTCCCAATTC TCTCTCCTCC GTCCCCTTCC TCCACTGCTG

2821  CCTAATGCAA GGCAGTGGCT CAGCAGCAAG AATGCTGGTT CTACATCCCG AGGAGTGTCT

2881  GAGGTGCGCC CCACTCTGTA CAGAGGCTGT TTGGGCAGCC TTGCCTCCAG AGAGCAGATT

2941  CCAGCTTCGG AAGCCCCTGG TCTAACTTGG GATCTGGGAA TGGAAGGTGC TCCCATCGGA

3001  GGGGACCCTC AGAGCCCTGG AGACTGCCAG GTGGGCCTGC TGCCACTGTA AGCCAAAAGG

3061  TGGGGAAGTC CTGACTCCAG GGTCCTTGCC CCACCCCTGC CTGCCACCTG GGCCCTCACA

3121  GCCCAGACCC TCACTGGGAG GTGAGCTCAG CTGCCCTTTG GAATAAAGCT GCCTGATCCA

3181  AAAAAAAAAA AAAAAA
```

By "variant" is meant a polynucleotide or polypeptide sequence that differs from a reference sequence by one or more nucleotides or one or more amino acids. An exemplary TMPRSS6 variant is TMPRSS6 (A736V), resulting from SNP rs855791 (G→A).

By "single nucleotide polymorphism" or "SNP" is meant a naturally occurring DNA sequence variant in which a single nucleotide in the genome differs between members of a biological species or between paired chromosomes in an individual. SNPs can be used as genetic markers for variant alleles. In one embodiment, the TMPRSS6 SNP is rs855791.

By "rs855791" is meant a single nucleotide polymorphism (SNP) in the human TMPRSS6 gene, 2321G→A, resulting in an alanine to valine substitution (A736V) in the catalytic domain of Matriptase-2 (MT2), which is encoded by the TMPRSS6 gene. The allele with highest frequency in the human population (the major allele) is 2321G, encoding 736A. The allele with lowest frequency in the human population (minor allele) is 2321A, encoding 736V.

By "heterozygous" is meant that a chromosomal locus has two different alleles. In one embodiment of the methods described herein, heterozygous refers to a genotype in which one allele has a TMPRSS6 nucleic acid sequence encoding a TMPRSS6 polypeptide having an alanine at amino acid position 736 (e.g., having a G or C at nucleotide position 2321 of a TMPRSS6 nucleic acid molecule) (rs855791 major allele), and the other allele has a variant TMPRSS6 nucleic acid sequence encoding a TMPRSS6 polypeptide comprising a valine at amino acid position 736 (e.g., having an A or T at nucleotide position 2321 of a TMPRSS6 nucleic acid molecule) (rs855791 minor allele).

By "homozygous" is meant that a chromosomal locus has two identical alleles. In certain embodiments of the methods described herein, homozygous refers to a genotype in which both alleles have a TMPRSS6 nucleic acid sequence encoding a TMPRSS6 polypeptide comprising an alanine at amino acid position 736 (e.g., having a G or C at nucleotide position 2321 of a TMPRSS6 nucleic acid molecule) (rs855791 homozygous major allele). In certain embodiments, homozygous refers to a genotype in which both alleles have a TMPRSS6 nucleic acid sequence encoding a TMPRSS6 polypeptide comprising a valine at amino acid position 736 (e.g., having an A or T at nucleotide position 2321 of a TMPRSS6 nucleic acid molecule) (rs855791 homozygous minor allele).

"Determining that a patient has at least one copy of the TMPRSS6 rs855791 major allele" includes, but is not limited to, performing an assay to determine that a patient has at least one copy of the TMPRSS6 rs855791 major allele; ordering an assay to determine that a patient has at least one copy of the TMPRSS6 rs855791 major allele; prescribing an assay to determine that a patient has at least one copy of the TMPRSS6 rs855791 major allele; otherwise directing or controlling that an assay be performed to determine that a patient has at least one copy of the TMPRSS6 rs855791 major allele; and reviewing TMRSS6 genotype assay data or protein or nucleic acid sequence data to determine that a patient has at least one copy of the TMPRSS6 rs855791 major allele.

By "interleukin 6" or "IL-6" or "IL-6 polypeptide" is meant a polypeptide or fragment thereof having at least about 85% or greater amino acid identity to the amino acid sequence provided at NCBI Accession No. NP_000591 and having IL-6 biological activity. IL-6 is a pleotropic cytokine with multiple biologic functions. Exemplary IL-6 biological activities include immunostimulatory and pro-inflammatory activities. An exemplary IL-6 amino acid sequence is provided below:

```
                                                          (SEQ ID NO: 5)
  1 MCVGARRLGR GPCAALLLLG LGLSTVTGLH CVGDTYPSND RCCHECRPGN GMVSRCSRSQ

61 NTVCRPCGPG FYNDVVSSKP CKPCTWCNLR SGSERKQLCT ATQDTVCRCR AGTQPLDSYK

121 PGVDCAPCPP GHFSPGDNQA CKPWTNCTLA GKHTLQPASN SSDAICEDRD PPATQPQETQ

181 GPPARPITVQ PTEAWPRTSQ GPSTRPVEVP GGRAVAAILG LGLVLGLLGP LAILLALYLL

241 RRDQRLPPDA HKPPGGGSFR TPIQEEQADA HSTLAKI
```

By "interleukin 6 (IL-6) nucleic acid" is meant a polynucleotide encoding an interleukin 6 (IL-6) polypeptide. An exemplary interleukin 6 (IL-6) nucleic acid sequence is provided at NCBI Accession No. NM_000600. The exemplary sequence at NCBI Accession No. NM_000600 is provided below.

```
                                                          (SEQ ID NO: 6)
   1 AATATTAGAG TCTCAACCCC CAATAAATAT AGGACTGGAG ATGTCTGAGG CTCATTCTGC

61 CCTCGAGCCC ACCGGGAACG AAAGAGAAGC TCTATCTCCC CTCCAGGAGC CCAGCTATGA

121 ACTCCTTCTC CACAAGCGCC TTCGGTCCAG TTGCCTTCTC CCTGGGGCTG CTCCTGGTGT

181 TGCCTGCTGC CTTCCCTGCC CCAGTACCCC CAGGAGAAGA TTCCAAAGAT GTAGCCGCCC

241 CACACAGACA GCCACTCACC TCTTCAGAAC GAATTGACAA ACAAATTCGG TACATCCTCG

301 ACGGCATCTC AGCCCTGAGA AAGGAGACAT GTAACAGAG TAACATGTGT GAAAGCAGCA

361 AAGAGGCACT GGCAGAAAAC AACCTGAACC TTCCAAAGAT GGCTGAAAAA GATGGATGCT

421 TCCAATCTGG ATTCAATGAG GAGACTTGCC TGGTGAAAAT CATCACTGGT CTTTTGGAGT

481 TTGAGGTATA CCTAGAGTAC CTCCAGAACA GATTTGAGAG TAGTGAGGAA CAAGCCAGAG

541 CTGTGCAGAT GAGTACAAAA GTCCTGATCC AGTTCCTGCA GAAAAAGGCA AAGAATCTAG

601 ATGCAATAAC CACCCCTGAC CCAACCACAA ATGCCAGCCT GCTGACGAAG CTGCAGGCAC

661 AGAACCAGTG GCTGCAGGAC ATGACAACTC ATCTCATTCT GCGCAGCTTT AAGGAGTTCC

721 TGCAGTCCAG CCTGAGGGCT CTTCGGCAAA TGTAGCATGG GCACCTCAGA TTGTTGTTGT

781 TAATGGGCAT TCCTTCTTCT GGTCAGAAAC CTGTCCACTG GGCACAGAAC TTATGTTGTT

841 CTCTATGGAG AACTAAAAGT ATGAGCGTTA GGACACTATT TTAATTATTT TTAATTTATT

901 AATATTTAAA TATGTGAAGC TGAGTTAATT TATGTAAGTC ATATTTATAT TTTTAAGAAG

961 TACCACTTGA AACATTTTAT GTATTAGTTT TGAAATAATA ATGGAAAGTG CTATGCAGT

1021 TTGAATATCC TTTGTTTCAG AGCCAGATCA TTTCTTGGAA AGTGTAGGCT TACCTCAAAT

1081 AAATGGCTAA CTTATACATA TTTTTAAAGA AATATTTATA TTGTATTTAT ATAATGTATA

1141 AATGGTTTTT ATACCAATAA ATGGCATTTT AAAAAATTCA GCAAAAAAAA AAAAAAAAA

1201 A
```

By "interleukin 6 receptor (IL-6R) complex" is meant a protein complex comprising an IL-6 receptor subunit alpha (IL-6Rα) and interleukin 6 signal transducer Glycoprotein 130, also termed interleukin 6 receptor subunit β (IL-6Rβ).

By "interleukin 6 receptor subunit α (IL-6Rα) polypeptide" is meant a polypeptide or fragment thereof having at least about 85% or greater amino acid identity to the amino acid sequence provided at NCBI Accession No. NP_000556 or NP_852004 and having IL-6 receptor biological activity. Exemplary IL-6Rα biological activities include binding to IL-6, binding to glycoprotein 130 (gp130), and regulation of cell growth and differentiation. An exemplary IL-6R sequence is provided below:

(SEQ ID NO: 7)

```
  1 MLAVGCALLA ALLAAPGAAL APRRCPAQEV ARGVLTSLPG DSVTLTCPGV EPEDNATVHW

61 VLRKPAAGSH PSRWAGMGRR LLLRSVQLHD SGNYSCYRAG RPAGTVHLLV DVPPEEPQLS

121 CFRKSPLSNV VCEWGPRSTP SLTTKAVLLV RKFQNSPAED FQEPCQYSQE SQKFSCQLAV

181 PEGDSSFYIV SMCVASSVGS KFSKTQTFQG CGILQPDPPA NITVTAVARN PRWLSVTWQD

241 PHSWNSSFYR LRFELRYRAE RSKTFTTWMV KDLQHHCVIH DAWSGLRHVV QLRAQEEFGQ

301 GEWSEWSPEA MGTPWTESRS PPAENEVSTP MQALTTNKDD DNILFRDSAN ATSLPVQDSS

361 SVPLPTFLVA GGSLAFGTLL CIAIVLRFKK TWKLRALKEG KTSMHPPYSL GQLVPERPRP

421 TPVLVPLISP PVSPSSLGSD NTSSHNRPDA RDPRSPYDIS NTDYFFPR
```

15

By "interleukin 6 receptor subunit β (IL-6Rβ) polypeptide" is meant a polypeptide or fragment thereof having at least about 85% or greater amino acid identity to the amino acid sequence provided at NCBI Accession No. NP_002175, NP_786943, or NP_001177910 and having IL-6 receptor biological activity. Exemplary IL-6Rβ biological activities include binding to IL-6Rα, IL-6 receptor signaling activity, and regulation of cell growth, differentiation, hepcidin expression etc. An exemplary IL-6Rβ sequence is provided below:

binding fragments or derivatives thereof, IL-6R binding polypeptides, such as anti-IL-6R antibodies and antigen binding fragments or derivatives thereof; and synthetic chemical molecules, such as JAK1 and JAK3 inhibitors.

By "IL-6 antibody" or "anti-IL-6 antibody" is meant an antibody that specifically binds IL-6. Anti-IL-6 antibodies include monoclonal and polyclonal antibodies that are specific for IL-6, and antigen-binding fragments or derivatives thereof. IL-6 antibodies are described in greater detail in Section 8.3.6.1 below.

(SEQ ID NO: 8)

```
  1 MLTLQTWLVQ ALFIFLTTES TGELLDPCGY ISPESPVVQL HSNFTAVCVL KEKCMDYFHV

61 NANYIVWKTN HFTIPKEQYT IINRTASSVT FTDIASLNIQ LTCNILTFGQ LEQNVYGITI

121 ISGLPPEKPK NLSCIVNEGK KMRCEWDGGR ETHLETNFTL KSEWATHKFA DCKAKRDTPT

181 SCTVDYSTVY FVNIEVWVEA ENALGKVTSD HINFDPVYKV KPNPPHNLSV INSEELSSIL

241 KLTWTNPSIK SVIILKYNIQ YRTKDASTWS QIPPEDTAST RSSFTVQDLK PFTEYVFRIR

301 CMKEDGKGYW SDWSEEASGI TYEDRPSKAP SFWYKIDPSH TQGYRTVQLV WKTLPPFEAN

361 GKILDYEVTL TRWKSHLQNY TVNATKLTVN LTNDRYLATL TVRNLVGKSD AAVLTIPACD

421 FQATHPVMDL KAFPKDNMLW VEWTTPRESV KKYILEWCVL SDKAPCITDW QQEDGTVHRT

481 YLRGNLAESK CYLITVTPVY ADGPGSPESI KAYLKQAPPS KGPTVRTKKV GKNEAVLEWD

541 QLPVDVQNGF IRNYTIFYRT IIGNETAVNV DSSHTEYTLS SLTSDTLYMV RMAAYTDEGG

601 KDGPEFTFTT PKFAQGEIEA IVVPVCLAFL LTTLLGVLFC FNKRDLIKKH IWPNVPDPSK

661 SHIAQWSPHT PPRHNFNSKD QMYSDGNFTD VSVVEIEAND KKPFPEDLKS LDLFKKEKIN

721 TEGHSSGIGG SSCMSSSRPS ISSSDENESS QNTSSTVQYS TVVHSGYRHQ VPSVQVFSRS

781 ESTQPLLDSE ERPEDLQLVD HVDGGDGILP RQQYFKQNCS QHESSPDISH FERSKQVSSV

841 NEEDFVRLKQ QISDHISQSC GSGQMKMFQE VSAADAFGPG TEGQVERFET VGMEAATDEG

901 MPKSYLPQTV RQGGYMPQ
```

By "IL-6 antagonist" is meant an agent that is capable of decreasing the biological activity of IL-6. IL-6 antagonists include agents that decrease the level of IL-6 polypeptide in serum, including agents that decrease the expression of an IL-6 polypeptide or nucleic acid; agents that decrease the ability of IL-6 to bind to the IL-6R; agents that decrease the expression of the IL-6R; and agents that decrease signal transduction by the IL-6R receptor when bound by IL-6. In preferred embodiments, the IL-6 antagonist decreases IL-6 biological activity by at least about 10%, 20%, 30%, 50%, 70%, 80%, 90%, 95%, or even 100%. As further described in Section 6.3.4 below, IL-6 antagonists include IL-6 binding polypeptides, such as anti-IL-6 antibodies and antigen As used herein, "diuretic efficiency" is calculated as mmol urinary sodium per doubling of loop diuretic dose (mmol Na/doubling of loop diuretic dose) according to the methods described in Hanberg et al., *Circ. Heart Fail.* 2016; 9:e003180, the disclosure of which is incorporated herein by reference in its entirety.

By "diuretic resistant heart failure" is meant heart failure in which the patient's diuretic efficiency is less than 100.

The terms "biomarker" or "marker," as used herein, refers to a molecule that can be detected. Therefore, a biomarker according to the present invention includes, but is not limited to, a nucleic acid, a polypeptide, a carbohydrate, a lipid, an inorganic molecule, an organic molecule, each of which may vary widely in size and properties. A "biomarker" can be a bodily substance relating to a bodily condition or disease. A "biomarker" can be detected using any means known in the art or by a previously unknown means that only becomes apparent upon consideration of the marker by the skilled artisan.

As used herein, "biomarker" in the context of the present invention encompasses, without limitation, proteins, nucleic acids, and metabolites, together with their polymorphisms, mutations, variants, modifications, subunits, fragments, protein-ligand complexes, and degradation products, elements, related metabolites, and other analytes or sample-derived measures. Biomarkers can also include mutated proteins or mutated nucleic acids. Biomarkers also encompass non-blood borne factors or non-analyte physiological markers of health status, such as clinical parameters, as well as traditional laboratory risk factors. As defined by the Food and Drug Administration (FDA), a biomarker is a characteristic (e.g. measurable DNA and/or RNA or a protein) that is "objectively measured and evaluated as an indicator of normal biologic processes, pathogenic processes, or pharmacologic responses to a therapeutic intervention or other interventions". Biomarkers also include any calculated indices created mathematically or combinations of any one or more of the foregoing measurements, including temporal trends and differences. Biomarkers may be measured at any level spatial or temporal localization, including but not limited to within a tumor, within in a cell, or on the membrane of a cell.

By "agent" is meant any compound or composition suitable to be administered in therapy, and explicitly includes chemical compounds; proteins, including antibodies or antigen-binding fragments thereof; peptides; and nucleic acid molecules.

By "subject" or "individual" is meant a human or non-human mammal, including, but not limited to, bovine, equine, canine, ovine, feline, and rodent, including murine and rattus, subjects. A "patient" is a human subject.

As used herein, the terms "treat," treating," "treatment," and the like refer to reducing or ameliorating a disorder, and/or signs or symptoms associated therewith, or slowing or halting the progression thereof. It will be appreciated that, although not precluded, treating a disorder or condition does not require that the disorder, condition or symptoms associated therewith be completely eliminated.

"Pre-treatment" means prior to the first administration of an IL-6 antagonist according the methods described herein. Pre-treatment does not exclude, and often includes, the prior administration of treatments other than an IL-6 antagonist, such as treatment with a diuretic, such as a loop diuretic.

By "biological sample" is meant any tissue, cell, fluid, or other material derived from an organism (e.g., human subject). In certain embodiments, the biological sample is serum, plasma, urine, or whole blood.

As used herein, an "instructional material" includes a publication, a recording, a diagram, or any other medium of expression which can be used to communicate the usefulness of a component of the invention in a kit for detecting biomarkers disclosed herein. The instructional material of the kit of the invention can, for example, be affixed to a container which contains the component of the invention or be shipped together with a container which contains the component. Alternatively, the instructional material can be shipped separately from the container with the intention that the instructional material and the component be used cooperatively by the recipient.

The "level" of one or more biomarkers means the absolute or relative amount or concentration of the biomarker in the sample as determined by measuring mRNA, cDNA, small organic molecules, nucleotides, ions or protein, or any portion thereof such as oligonucleotide or peptide. A level of a biomarker may refer, based on context, to a global level or a level within some subdivision of an organism or within a specific sample, by way of non-limiting example a level may refer to the amount or concentration of a biomarker in a urine sample or the level may refer to the amount or concentration of the same biomarker in a plasma sample.

"Measuring" or "measurement," or alternatively "detecting" or "detection," means determining the presence, absence, quantity or amount (which can be an effective amount) of either a given substance within a clinical or subject-derived sample, including the derivation of qualitative or quantitative concentration levels of such substances, or otherwise determining the values or categorization of a subject's clinical parameters.

A "reference level" of a biomarker means a level of a biomarker that is indicative of the presence or absence of a particular phenotype or characteristic. When the level of a biomarker in a subject is above the reference level of the biomarker it is indicative of the presence of, or relatively heightened level of, a particular phenotype or characteristic. When the level of a biomarker in a subject is below the reference level of the biomarker it is indicative of a lack of or relative lack of a particular phenotype or characteristic.

Other Interpretational Conventions

Unless otherwise specified, antibody constant region residue numbering is according to the EU index as in Kabat.

Ranges: throughout this disclosure, various aspects of the invention can be presented in a range format. Ranges include the recited endpoints. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Unless specifically stated or apparent from context, as used herein the term "or" is understood to be inclusive.

Unless specifically stated or apparent from context, as used herein, the terms "a", "an", and "the" are understood to be singular or plural. That is, the articles "a" and "an" are used herein to refer to one or to more than one (i.e., to at least one) of the grammatical object of the article. By way of example, "an element" means one element or more than one element.

In this disclosure, "comprises," "comprising," "containing," "having," "includes," "including," and linguistic variants thereof have the meaning ascribed to them in U.S. patent law, permitting the presence of additional components beyond those explicitly recited.

Unless specifically stated or otherwise apparent from context, as used herein the term "about" is understood as within a range of normal tolerance in the art, for example within 2 standard deviations of the mean and is meant to encompass variations of ±20% or ±10%, more preferably ±5%, even more preferably ±1%, and still more preferably ±0.1% from the stated value.

Where an antibody equilibrium dissociation constant ($K_D$) is reported, $K_D$ is determined by surface plasmon resonance with the antibody (or antigen-binding fragment thereof) fixed to the chip surface with ligand flowed thereover.

Summary of Experimental Observations

As further described below in Example 1, consecutive heart failure ("HF") patients receiving high dose diuretic therapy at an outpatient treatment center were enrolled in a prospective observational study. Plasma levels of IL-6 were measured to query systemic associations of this pro-inflammatory cytokine with various disease parameters, and urine levels of IL-6 were measured to query IL-6 associations with local inflammation and neurohormonal activation at the level of renal tissues.

Plasma and urine IL-6 levels were only modestly correlated with one another.

Increases in urine levels of IL-6 were significantly correlated in these heart failure patients with measures of renal impairment, such as diuretic resistance, lower estimated glomerular filtration rate ("eGFR"), and increased tissue-level renin-angiotensin-aldosterone system ("RAAS") activation.

Although an inverse association between diuretic efficiency and plasma IL-6 was also observed, upon adjustment for eGFR only urine IL-6 remained significantly associated with risk of low diuretic efficiency in these patients. Furthermore, when urine IL-6 and plasma IL-6 were both entered into a logistic regression model, only urine IL-6 remained associated with risk of low diuretic efficiency while plasma IL-6 showed no such association.

These data demonstrate that urine IL-6 level is a useful biomarker for renal inflammation, and can be used to gauge renal dysfunction in the setting of heart failure (cardiorenal syndrome). The data further suggest that serial measurements of urine IL-6 can be used to measure the renal benefits of treatments administered to patients with heart failure, notably heart failure patients with cardiorenal syndrome.

The urine IL-6 data, and to some extent the plasma IL-6 data, predict that treatment with an IL-6 antagonist should be effective to reduce renal inflammation in heart failure patients, that is, to treat symptoms of cardiorenal syndrome. However, because infection is often a precipitating cause of acute decompensation in heart failure patients, it is important to limit anti-cytokine and other immunosuppressive therapies to those heart failure patients who are likely to respond with improved renal and/or cardiac function. The cost of chronic IL-6 antagonist therapy also militates for limiting treatment to those heart failure patients who are likely to respond with improved renal and/or cardiac function.

Figure 1B:
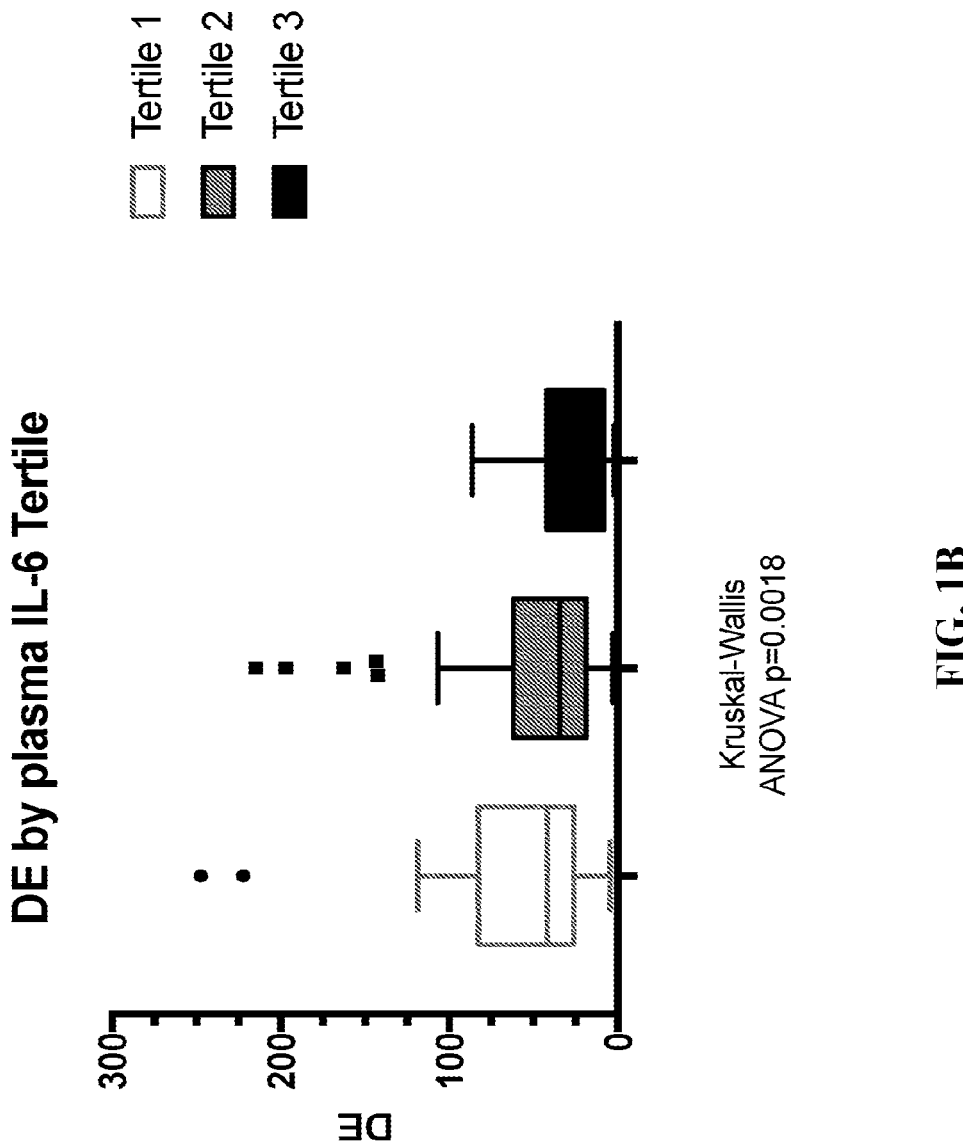
FIG. 1B is a bar graph showing diuretic efficiency ("DE") by tertiles of plasma IL-6 in the 129 heart failure ("HF") patients whose data is shown in FIG. 1A. Whiskers extend from the 10$^{th}$ to 90$^{th}$ percentile.

As detailed below in Example 2, the analysis conducted in Example 1 was expanded to 129 patients. FIG. 1A is a bar graph showing diuretic efficiency ("DE") by tertiles of urine IL-6, confirming the inverse correlation of urinary IL-6 level with diuretic efficiency observed in the 98 patient subset. FIG. 1B is a bar graph showing diuretic efficiency ("DE") by tertiles of plasma IL-6 in these 129 patients, confirming an inverse correlation of plasma IL-6 levels with diuretic efficiency.

The genotype of each of the 129 patients at the rs855791 single nucleotide polymorphism ("SNP") in transmembrane protease serine 6 ("TMPRSS6") was assessed. The TMPRSS6 polypeptide, also known as Matriptase-2 (MT2), cleaves hemojuvelin and inhibits bone morphogenetic protein signaling. The rs855791 (G2321A) SNP alters the TMPRSS6 protein sequence: the allele with highest frequency in the human population (the major allele) is 2321G, encoding 736A; the allele with lowest frequency in the human population (minor allele) is 2321A, encoding 736V.

Figure 2A:
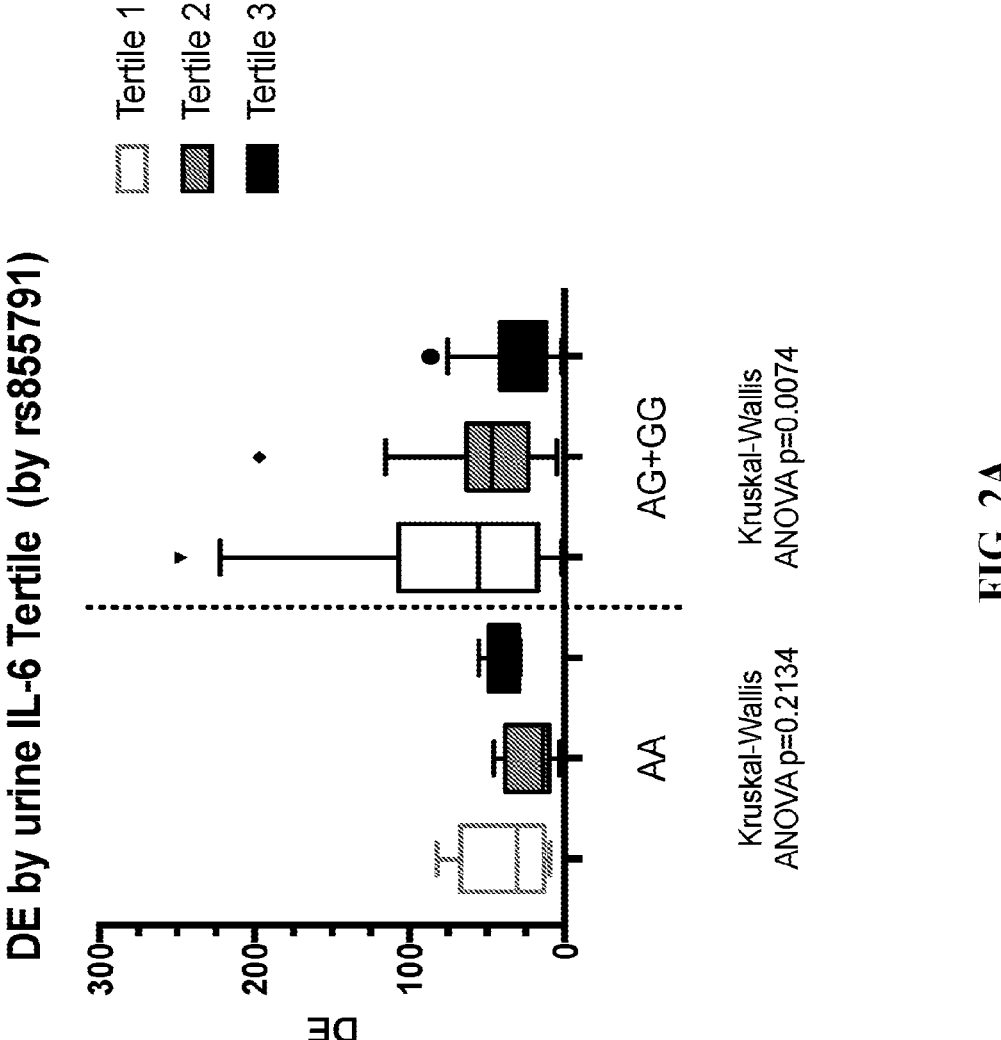
FIG. 2A plots DE by tertiles of urine IL-6 in the patients reported in FIGS. 1A and 1B further stratified by genotype, with the left panel showing results for patients homozygous for the TMPRSS6 rs855791 SNP minor allele (2321G→A; A736V) and right panel showing results for patients having at least one copy of the TMPRSS6 rs855791 SNP major allele (2321G; A736).

As shown in FIG. 2A, urine levels of IL-6 were inversely correlated with diuretic efficiency only in the patients having at least one copy of the major allele of the TMPRSS6 rs855791 SNP (FIG. 2A, right panel, "AG+GG"); urine levels of IL-6 are not significantly correlated with diuretic efficiency in patients homozygous for the minor allele (FIG. 2A, left panel, "AA").

Figure 2B:
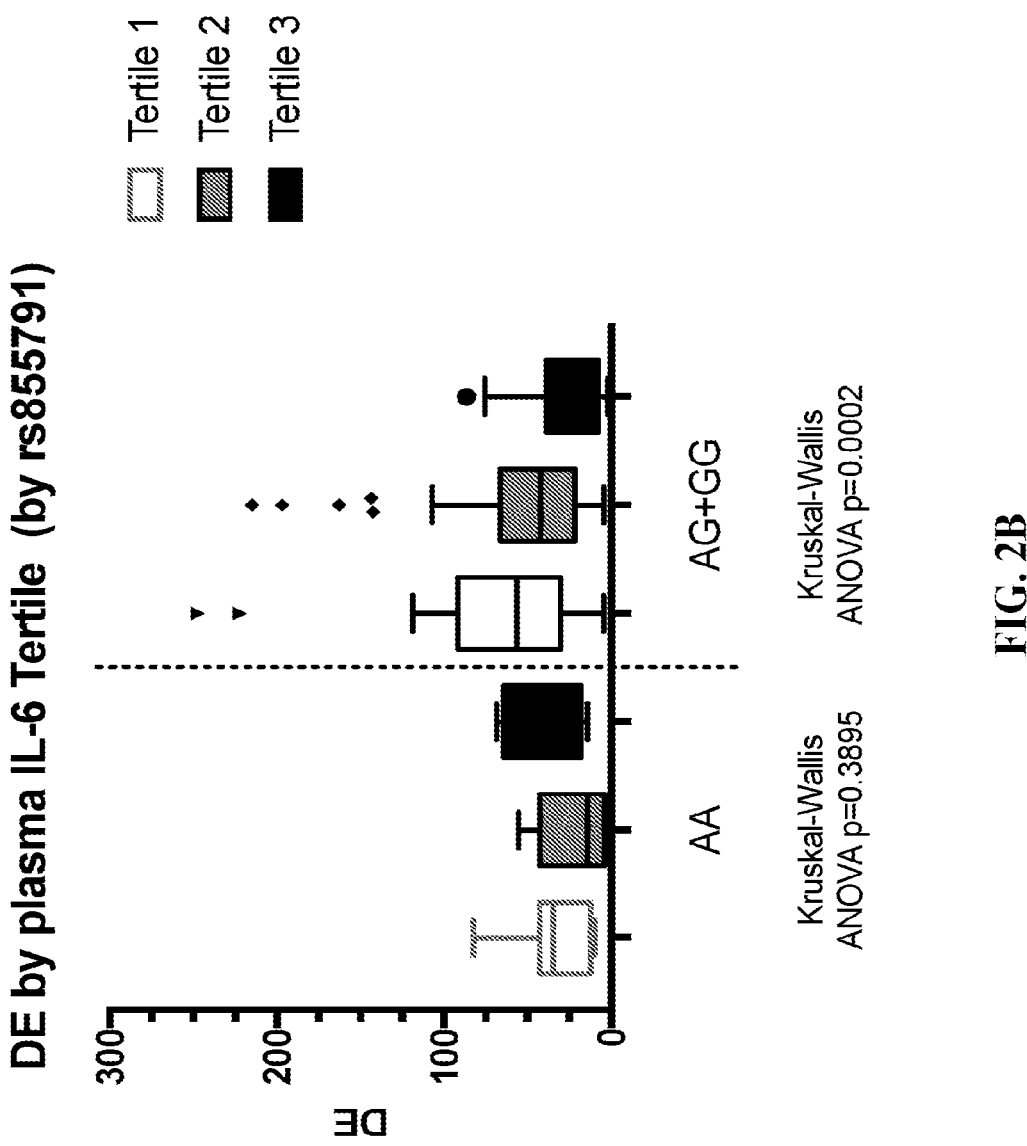
FIG. 2B plots DE by tertiles of plasma IL-6 in the patients reported in FIGS. 1A and 1B further stratified by genotype, with the left panel showing results for patients homozygous for the TMPRSS6 rs855791 SNP minor allele (2321G→A; A736V) and right panel showing results for patients having at least one copy of the TMPRSS6 rs855791 SNP major allele (2321G; A736).

As shown in FIG. 2B, plasma levels of IL-6 correlated inversely with diuretic efficiency only in the patients having at least one copy of the major allele of the TMPRSS6 rs855791 SNP (FIG. 2B, right panel, "AG+GG"); plasma levels of IL-6 are not significantly correlated with diuretic efficiency in patients homozygous for the minor allele (FIG. 2B, left panel, "AA").

These data suggested that diuretic resistance (low diuretic efficiency) in heart failure patients could be treated with an IL-6 antagonist, but only in those having at least one copy of the TMPRSS6 rs855791 major allele.

In mouse M1 CCD cells, which are genotypically analogous to human cells homozygous for the TMPRSS6 rs855791 major allele, the addition of IL-6 correlated with the expression of ion transporters, NKCC2, ENaC-beta, and NCC. Increased expression of these ion transporters provides a putative mechanism for IL-6 mediated diuretic resistance. And because the increased expression is not known to be linked to hepcidin expression, these data suggested that IL-6 antagonism could be effective in treating diuretic resistance even in patients homozygous for the TMPRSS6 rs855791 minor allele.

Secondary analysis of data from two large clinical trials in different heart failure patient populations confirmed the association of diuretic resistance with IL-6 level (Example 5), independently of TMPRSS6 rs855791 genotype (Example 6), providing evidence that IL-6 antagonism should also be effective in treating diuretic resistance in patients homozygous for the TMPRSS6 rs855791 minor allele.

Methods of Treating Diuretic Resistance

Accordingly, in a first aspect, methods are provided for treating a patient who requires diuresis but is resistant to diuretics. The methods comprise administering, in combination with a diuretic, a therapeutically effective amount of an IL-6 antagonist to the patient.

In certain embodiments, the patient has elevated pre-treatment urine levels of IL-6. In some embodiments, the patient has elevated pre-treatment plasma IL-6 levels. In certain embodiments, the patient has elevated pre-treatment levels of IL-6 in urine and in plasma.

In some embodiments, the patient has diuretic-resistant heart failure. In various embodiments, the patient has cardiorenal syndrome.

In some embodiments, the patient has been determined to have at least one copy of the TMPRSS6 rs855791 major allele. In other embodiments, the patient is homozygous for the TMPRSS6 rs855791 minor allele.

Diuretic Efficiency

In the methods described herein, the patient in need of the IL-6 antagonist treatment has a disease or condition that requires diuresis, and is diuretic resistant.

In certain embodiments, the patient has been treated or is being treated with a thiazide diuretic, such as chlorothiazide (Diuril®), chlorthalidone, hydrochlorothiazide (Microzide®), indapamide, or metolazone. In certain embodiments, the patient has been treated or is being treated with a loop diuretic, such as bumetanide (Bumex®), ethacrynic acid (Edecrin®), furosemide (Lasix®), or torsemide (Demadex®). In certain embodiments, the patient has been treated or is being treated with a potassium-sparing diuretic, such as amiloride, eplerenone (Inspra®), spironolactone (Aldactone®), or triamterene (Dyrenium®). In some embodiments, the patient has been treated or is being treated with more than one diuretic. In some embodiments, the patient has been treated or is being treated with a plurality of different types of diuretics.

By definition, the patient resistant to diuretics has a low diuretic efficiency. Diuretic efficiency is calculated as the increase in sodium output per doubling of the loop diuretic dose, centered on a dose of 40 mg of IV furosemide equivalents: diuretic efficiency=(mmol Na output)/($\log_2$(administered loop diuretic dose)−4.32). See Hanberg et al., *Circ. Heart Fail.* 2016; 9:e003180, the disclosure of which is incorporated herein by reference in its entirety.

In some embodiments, the patient has a diuretic efficiency of less than 500, such as less than 450, 400, 350, 300, 250, or 200. In some embodiment, the patient has a diuretic efficiency of less than 200, such as less than 195, 190, 185, 180, 175, 170, 165, 160, 155, or 150. In some embodiments, the patient has a diuretic efficiency of less than 150, such as less than 145, 140, 135, 130, 125, 120, 110, 105, or 100. In some embodiments, the patient has a diuretic efficiency of less than 100, such as less than 95, 90, 85, 80, 75, 70, 65, 60, 55, or 50. In particular embodiments, the patient has a diuretic efficiency of less than 50, such as less than 45, 40, 35, 30, or even less than 25, 20, 15, or 10.

In some embodiments, the patient resistant to diuretics requires a diuretic treatment of no less than 40 mg of furosemide (or equivalent) daily. In some of these embodiments, the patient requires a diuretic treatment of no less than 80 mg of furosemide (or equivalent) daily. In some of these embodiments, the patient requires a diuretic treatment of no less than 120 mg of furosemide (or equivalent) daily.

Pre-Treatment IL-6 Levels

Pre-Treatment Levels of IL-6 in Urine

In certain embodiments, the patient has pre-treatment urine levels of IL-6 of more than 5.0 pg IL-6/g creatinine, 6.0 pg IL-6/g creatinine, 7.0 pg IL-6/g creatinine, 8.0 pg IL-6/g creatinine, 9.0 pg IL-6/g creatinine, or 10.0 pg IL-6/g creatinine. In certain embodiments, the patient has pre-treatment IL-6 urine levels of more than 11.0 pg IL-6/g creatinine, 12.0 pg IL-6/g creatinine, 13.0 pg IL-6/g creatinine, 14.0 pg IL-6/g creatinine, or 15.0 pg IL-6/g creatinine. In further embodiments, the patient has pre-treatment IL-6 levels in urine of more than 16.0 pg IL-6/g creatinine, 17.0 pg IL-6/g creatinine, 18.0 pg IL-6/g creatinine, 19.0 pg IL-6/g creatinine, or 20.0 pg IL-6/g creatinine. In particular embodiments, the patient has pre-treatment IL-6 levels in urine of more than 21.0 pg IL-6/g creatinine, 22.0 pg IL-6/g creatinine, 23.0 pg IL-6/g creatinine, 24.0 pg IL-6/g creatinine, 25.0 pg IL-6/g creatinine, 26.0 pg IL-6/g creatinine, 27.0 pg IL-6/g creatinine, 28.0 pg IL-6/g creatinine, 29.0 pg IL-6/g creatinine, or even more than 30.0 pg IL-6/g creatinine. In certain embodiments, the patient has pre-treatment urine IL-6 levels of more than 35.0 pg/g creatinine.

In certain embodiments, the patient has pre-treatment urine levels of more than 14.2 pg IL-6/g creatinine ("elevated urine IL-6 levels"). In other embodiments, the patient has pre-treatment urine levels of less than 14.2 pg IL-/g creatinine.

In certain embodiments, the patient has levels of IL-6 in urine prior to treatment with an IL-6 antagonist and prior to treatment with a loop diuretic of more than 5.0 pg IL-6/g creatinine, 6.0 pg IL-6/g creatinine, 7.0 pg IL-6/g creatinine, 8.0 pg IL-6/g creatinine, 9.0 pg IL-6/g creatinine, or 10.0 pg IL-6/g creatinine. In some of these embodiments, the patient has IL-6 urine levels of more than 11.0 pg IL-6/g creatinine, 12.0 pg IL-6/g creatinine, 13.0 pg IL-6/g creatinine, 14.0 pg IL-6/g creatinine, or 15.0 pg IL-6/g creatinine. In further embodiments, the patient has levels of IL-6 in urine prior to treatment with an IL-antagonist and prior to treatment with a loop diuretic of more than 16.0 pg IL-6/g creatinine, 17.0 pg IL-6/g creatinine, 18.0 pg IL-6/g creatinine, 19.0 pg IL-6/g creatinine, or 20.0 pg IL-6/g creatinine. In particular embodiments, the patient has IL-6 levels in urine of more than 21.0 pg IL-6/g creatinine, 22.0 pg IL-6/g creatinine, 23.0 pg IL-6/g creatinine, 24.0 pg IL-6/g creatinine, 25.0 pg IL-6/g creatinine, 26.0 pg IL-6/g creatinine, 27.0 pg IL-6/g creatinine, 28.0 pg IL-6/g creatinine, 29.0 pg IL-6/g creatinine, or even more than 30.0 pg IL-6/g creatinine. In certain embodiments, the patient has urine IL-6 levels prior to treatment with an IL-antagonist and prior to treatment with a loop diuretic of more than 35.0 pg/g creatinine.

In certain embodiments, the patient has levels of IL-6 in urine prior to treatment with an IL-6 antagonist and prior to treatment with a loop diuretic of more than 14.2 pg IL-6/g creatinine. In other embodiments, the patient has levels of IL-6 in urine prior to treatment with an IL-antagonist and prior to treatment with a loop diuretic of less than 14.2 pg IL-/g creatinine.

Pre-Treatment Levels of IL-6 in Plasma

In various embodiments, the patient has elevated pre-treatment plasma IL-6 levels.

In certain embodiments, the patient has pre-treatment plasma levels of IL-6 of more than 2.0 pg/mL. In other embodiments, the patient has pre-treatment plasma levels of IL-6 of less than 2.0 pg/mL.

In certain embodiments, the patient has pre-treatment plasma levels of IL-6 of more than 1.0 pg/ml, 1.1 pg/ml, 1.2 pg/ml, 1.3 pg/ml, 1.4 pg/ml, 1.5 pg/ml, 1.6 pg/ml, 1.7 pg/ml, 1.8 pg/ml, 1.9 pg/ml, or 2.0 pg/ml. In certain embodiments, the patient has pre-treatment plasma levels of IL-6 of more than 2.1 pg/ml, 2.2 pg/ml, 2.3 pg/ml, 2.4 pg/ml, 2.5 pg/ml, 2.6 pg/ml, 2.7 pg/ml, 2.8 pg/ml, 2.9 pg/ml, or 3.0 pg/ml. In certain embodiments, the patient has pre-treatment plasma levels of IL-6 of more than 3.1 pg/ml, 3.2 pg/ml, 3.3 pg/ml, 3.4 pg/ml, 3.5 pg/ml, 3.6 pg/ml, 3.7 pg/ml, 3.8 pg/ml, or 3.9 pg/ml.

In some embodiments, the patient has a pre-treatment IL-6 level of greater than 2 pg/mL, such as great than 3 pg/mL, 4 pg/mL, 5 pg/mL, 6 pg/mL, 8 pg/mL, 10 pg/mL, 15 pg/mL, or 20 pg/mL. In certain embodiments, the patient has a pre-treatment IL-6 level of greater than 3 pg/mL. In certain embodiments, the patient has a pre-treatment IL-6 level of greater than 5 pg/mL. In certain embodiments, the patient has a pre-treatment IL-6 level of greater than 10 pg/mL.

Measurement of Pre-Treatment IL-6 Levels

Concentrations of IL-6 in urine, plasma, and serum can be determined using any standard assay known in the art. When IL-6 is measured in urine, the level may be indexed or normalized to another biomarker, in certain embodiments urinary creatinine.

In particular embodiments, concentrations are measured using the MesoScale Discovery (MSD) platform (Meso Scale diagnostics, Gaithersburg, MD, USA).

Heart Failure

In typical embodiments of the methods described herein, the patient has heart failure.

In certain embodiments, the patient has NYHA functional class I heart failure. In certain embodiments, the patient has NYHA functional class II heart failure. In certain embodiments, the patient has NYHA functional class III heart failure. In certain embodiments, the patient has NYHA functional class IV heart failure.

In certain embodiments, the patient has acute heart failure. In certain embodiments, the patient has chronic heart failure.

In certain embodiments, the patient has a type of heart failure selected from Table 1 below.

TABLE 1

| ICD-10-CM | Description |
| --- | --- |
| I50 | Heart failure |
| | Heart failure complicating abortion or ectopic or molar pregnancy, heart failure following surgery, heart failure due to hypertension, heart failure due to hypertension with chronic kidney disease, obstetric surgery and procedures, rheumatic heart failure |
| I50.9 | Heart failure, unspecified |
| | Biventricular (heart) failure NOS |
| | Cardiac, heart or myocardial failure NOS |
| | Congestive heart disease |
| | Congestive heart failure |
| | Right ventricular failure |
| | (secondary to left heart failure) |
| I50.1 | Left ventricular failure |
| | Cardiac asthma |
| | Edema of lung with heart disease NOS |
| | Edema of lung with heart failure |
| | Left heart failure |
| | Pulmonary edema with heart disease NOS |
| | Pulmonary edema with heart failure |
| I50.20 | Unspecified systolic (congestive) heart failure |
| I50.21 | Acute systolic (congestive) heart failure |
| I50.22 | Chronic systolic (congestive) heart failure |
| I50.23 | Acute on chronic systolic (congestive) heart failure |
| I50.30 | Unspecified diastolic (congestive) heart failure |
| I50.31 | Acute diastolic (congestive) heart failure |
| I50.32 | Chronic diastolic (congestive) heart failure |
| I50.33 | Acute on chronic diastolic (congestive) heart failure |
| I50.40 | Unspecified combined systolic (congestive) and diastolic (congestive) heart failure |
| I50.41 | Acute combined systolic (congestive) and diastolic (congestive) heart failure |
| I50.42 | Chronic combined systolic (congestive) and diastolic (congestive) heart failure |
| I50.43 | Acute on chronic combined systolic (congestive) and diastolic (congestive) heart failure |
| I50.1 | Left ventricular failure |
| | Heart failure, unspecified |
| | Biventricular (heart) failure NOS |
| | Cardiac, heart or myocardial failure NOS |
| | Congestive heart disease |
| | Congestive heart failure |
| | Right ventricular failure |
| | (secondary to left heart failure) |

In certain embodiments, the patient has cardiorenal syndrome. In particular embodiments, the patient has cardiorenal syndrome type 1. In particular embodiments, the patient has cardiorenal syndrome type 2. In particular embodiments, the patient has cardiorenal syndrome type 3. In particular embodiments, the patient has cardiorenal syndrome type 4.

In certain embodiments, the patient has diuretic resistant heart failure. In certain of these embodiments, the heart failure patient has a diuretic efficiency of less than 100, 95, 90, 85, 80, 75, 70, 65, 60, 55, or 50. In particular embodiments, the patient has a diuretic efficiency of less than 45, 40, 35, 30, or even less than 25, 20, 15, or 10.

8.3.4. Kidney Disease

In some embodiments of methods described herein, the patient has kidney disease.

In certain embodiments, the patient has diuretic resistant kidney disease. In certain of these embodiments, the kidney disease patient has a diuretic efficiency of less than 100, 95, 90, 85, 80, 75, 70, 65, 60, 55, or 50. In particular embodiments, the patient has a diuretic efficiency of less than 45, 40, 35, 30, or even less than 25, 20, 15, or 10.

In particular embodiments, the patient has hepatorenal syndrome.

TMPRSS6 rs855791 Genotype

In certain embodiments, the patient has previously been determined to have at least one copy of the TMPRSS6 rs855791 major allele. In other embodiments, the method further comprises the earlier step of determining that the patient has at least one copy of the TMPRSS6 rs855791 major allele.

Preferably, the genotype at both alleles is determined, thus permitting identification and discrimination of patients who are homozygous for the TMPRSS6 rs855791 major allele, heterozygous for the major and minor TMPRSS6 rs855791 alleles, and homozygous for the TMPRSS6 rs855791 minor allele.

The absence (major allele) or presence (minor allele) of SNP rs855791 (2321G→A) in the TMPRSS6 gene is determined using standard techniques.

Typically, PCR is used to amplify a biological sample obtained from the patient.

In certain embodiments, the absence or presence of polymorphism is detected concurrently with amplification using real-time PCR (RT-PCR). In certain embodiments, the RT-PCR assay employs 5' nuclease (TaqMan® probes), molecular beacons, and/or FRET hybridization probes. *Reviewed in Espy et al., Clin. Microbiol. Rev.* 2006 January; 19(1): 165-256, incorporated herein by reference in its entirety. In typical embodiments, a commercially available assay is used. In select embodiments, the commercially available assay is selected from the group consisting of TaqMan™ SNP Genotyping Assays (ThermoFisher); PCR SNP Genotyping Assay (Qiagen); Novallele Genotyping Assays (Canon); and SNP Type™ assays (formerly SNPtype) (Fluidigm).

In certain embodiments, the absence or presence of polymorphism is detected following amplification using hybridization with a probe specific for SNP rs855791, restriction endonuclease digestion, nucleic acid sequencing, primer extension, microarray or gene chip analysis, mass spectrometry, and/or a DNAse protection assay. In certain embodiments, the allelic variants are called by sequencing. In certain embodiments, Sanger sequencing is used. In certain embodiments, one of a variety of next-generation sequencing techniques is used, including for example a sequencing technique selected from the group consisting of microarray sequencing, Solexa sequencing (Illumina), Ion Torrent (Life Technologies), SOliD (Applied Biosystems), pyrosequencing, single-molecule real-time sequencing (Pacific Bio), nanopore sequencing and tunneling currents sequencing.

In certain embodiments, the absence or presence of polymorphisms is detected using the procedures set forth in Example 2 below.

IL-6 Antagonists

The IL-6 antagonist used in the methods described herein is capable of decreasing the biological activity of IL-6.

Anti-IL-6 Antibodies

In certain embodiments, the IL-6 antagonist is an anti-IL-6 antibody or antigen-binding fragment or derivative thereof.

In certain embodiments, the IL-6 antagonist is a full-length anti-IL-6 monoclonal antibody. In particular embodiments, the full-length monoclonal antibody is an IgG antibody. In certain embodiments, the full-length monoclonal antibody is an IgG1, IgG2, IgG3, or IgG4 antibody. In certain embodiments, the IL-6 antagonist is a polyclonal composition comprising a plurality of species of full-length anti-IL-6 antibodies, each of the plurality having unique CDRs. In certain embodiments, the IL-6 antagonist is an antibody fragment selected from Fab, Fab', and F(ab')2 fragments. In certain embodiments, the IL-6 antagonist is a scFv, a disulfide-linked Fv (dsFv), or a single domain antibody, such as a camelid-derived VHH single domain Nanobody. In certain embodiments, the IL-6 antagonist is immunoconjugate or fusion comprising an IL-6 antigen-binding fragment. In certain embodiments, the antibody is bispecific or multispecific, with at least one of the antigen-binding portions having specificity for IL-6.

In certain embodiments, the antibody is fully human. In certain embodiments, the antibody is humanized. In certain embodiments, the antibody is chimeric and has non-human V regions and human C region domains. In certain embodiments, the antibody is murine.

In typical embodiments, the anti-IL-6 antibody has a $K_D$ for binding human IL-6 of less than 100 nM. In certain embodiments, the anti-IL-6 antibody has a $K_D$ for binding human IL-6 of less than 75 nM, 50 nM, 25 nM, 20 nM, 15 nM, or 10 nM. In particular embodiments, the anti-IL-6 antibody has a $K_D$ for binding human IL-6 of less than 5 nM, 4 nM, 3 nM, or 2 nM. In selected embodiments, the anti-IL-6 antibody has a $K_D$ for binding human IL-6 of less than 1 nM, 750 pM, or 500 pM. In specific embodiments, the anti-IL-6 antibody has a $K_D$ for binding human IL-6 of no more than 500 pM, 400 pM, 300 pM, 200 pM, or 100 pM.

In typical embodiments, the anti-IL-6 antibody neutralizes the biological activity of IL-6. In certain embodiments, the neutralizing antibody prevents binding of IL-6 to the IL-6 receptor.

In typical embodiments, the anti-IL-6 antibody has an elimination half-life following intravenous administration of at least 7 days. In certain embodiments, the anti-IL-6 antibody has an elimination half-life of at least 14 days, at least 21 days, or at least 30 days.

In certain embodiments, the anti-IL-6 antibody has a human IgG constant region with at least one amino acid substitution that extends serum half-life as compared to the unsubstituted human IgG constant domain.

In certain embodiments, the IgG constant domain comprises substitutions at residues 252, 254, and 256, wherein the amino acid substitution at amino acid residue 252 is a substitution with tyrosine, the amino acid substitution at amino acid residue 254 is a substitution with threonine, and the amino acid substitution at amino acid residue 256 is a substitution with glutamic acid ("YTE"). See U.S. Pat. No. 7,083,784, incorporated herein by reference in its entirety. In certain extended half-life embodiments, the IgG constant domain comprises substitutions selected from T250Q/M428L (Hinton et al., *J. Immunology* 176:346-356 (2006)); N434A (Yeung et al., *J. Immunology* 182:7663-7671 (2009)); or T307A/E380A/N434A (Petkova et al., *International Immunology*, 18: 1759-1769 (2006)).

In certain embodiments, the elimination half-life of the anti-IL-6 antibody is increased by utilizing the FcRN-binding properties of human serum albumin. In certain embodiments, the antibody is conjugated to albumin (Smith et al., *Bioconjug. Chem.*, 12: 750-756 (2001)). In certain embodiments, the anti-IL-6 antibody is fused to bacterial albumin-binding domains (Stork et al., *Prot. Eng. Design Science* 20: 569-76 (2007)). In certain embodiments, the anti-IL-6 antibody is fused to an albumin-binding peptide (Nguygen et al., *Prot Eng Design Sel* 19: 291-297 (2006)). In certain embodiments, the anti-IL-antibody is bispecific, with one specificity being to IL-6, and one specificity being to human serum albumin (Ablynx, WO 2006/122825 (bispecific Nanobody)).

In certain embodiments, the elimination half-life of the anti-IL-6 antibody is increased by PEGylation (Melmed et al., *Nature Reviews Drug Discovery* 7: 641-642 (2008)); by HPMA copolymer conjugation (Lu et al., *Nature Biotechnology* 17: 1101-1104 (1999)); by dextran conjugation (*Nuclear Medicine Communications,* 16: 362-369 (1995)); by conjugation with homo-amino-acid polymers (HAPs; HAPylation) (Schlapschy et al., *Prot Eng Design Sel* 20: 273-284 (2007)); or by polysialylation (Constantinou et al., *Bioconjug. Chem.* 20: 924-931 (2009)).

MEDI5117 and Derivatives

In certain embodiments, the anti-IL-6 antibody or antigen-binding portion thereof comprises all six CDRs of MEDI5117. In particular embodiments, the antibody or antigen-binding portion thereof comprises the MEDI5117 heavy chain V region and light chain V region. In specific embodiments, the antibody is the full-length MEDI5117 antibody. The MEDI5117 antibody is described in WO 2010/088444 and US 2012/0034212, the disclosures of which are incorporated herein by reference in their entireties. The MEDI5117 antibody has the following CDR and heavy and light chain sequences:

```
MEDI5117 VH CDR1
                                    (SEQ ID NO: 9)
SNYMI

MEDI5117 VH CDR2
                                    (SEQ ID NO: 10)
DLYYYAGDTYYADSVKG

MEDI5117 VH CDR3
                                    (SEQ ID NO: 11)
WADDHPPWIDL

MEDI5117 VL CDR1
                                    (SEQ ID NO: 12)
RASQGISSWLA

MEDI5117 VL CDR2
                                    (SEQ ID NO: 13)
KASTLES

MEDI5117 VL CDR3
                                    (SEQ ID NO: 14)
QQSWLGGS

MEDI5117 Heavy chain
                                    (SEQ ID NO: 15)
EVQLVESGGGLVQPGGSLRLSCAASGFTISSNYMIWVRQAPGKGLEWVSD

LYYYAGDTYYADSVKGRFTMSRDISKNTVYLQMNSLRAEDTAVYYCARWA

DDHPPWIDLWGRGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKRVEPKSCDKTHTCPPCPAPELLGGPSVFLFPPKP

KDTLYITREPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLSPGK

MEDI5117 Light chain
                                    (SEQ ID NO: 16)
DIQMTQSPSTLSASVGDRVTITCRASQGISSWLAWYQQKPGKAPKVLIYK
```

-continued
```
ASTLESGVPSRFSGSGSGTEFTLTISSLQPDDFATYYCQQSWLGGSFGQG

TKLEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC
```

In certain embodiments, the anti-IL-6 antibody is a derivative of MED5117.

In certain embodiments, the MED5117 derivative includes one or more amino acid substitutions in the MED5117 heavy and/or light chain V regions.

In certain embodiments, the derivative comprises fewer than 25 amino acid substitutions, fewer than 20 amino acid substitutions, fewer than 15 amino acid substitutions, fewer than 10 amino acid substitutions, fewer than 5 amino acid substitutions, fewer than 4 amino acid substitutions, fewer than 3 amino acid substitutions, fewer than 2 amino acid substitutions, or 1 amino acid substitution relative to the original $V_H$ and/or $V_L$ of the MEDI5117 anti-IL-6 antibody, while retaining specificity for human IL-6.

In certain embodiments, the MED5117 derivative comprises an amino acid sequence that is at least 45%, at least 50%, at least 55%, at least 60%, at least 65%, at least 70%, at least 75%, at least 80%, at least 85%, at least 90%, at least 95%, or at least 99% identical to the amino acid sequence of the VH and VL domain of MEDI5117. The percent sequence identity is determined using BLAST algorithms using default parameters.

In certain embodiments, the MED5117 derivative comprises an amino acid sequence in which the CDRs comprise an amino acid sequence that is at least 45%, at least 50%, at least 55%, at least 60%, at least 65%, at least 70%, at least 75%, at least 80%, at least 85%, at least 90%, at least 95%, or at least 99% identical to the amino acid sequence of the respective CDRs of MEDI5117. The percent sequence identity is determined using BLAST algorithms using default parameters.

In certain embodiments, the $V_H$ and/or $V_L$ CDR derivatives comprise conservative amino acid substitutions at one or more predicted nonessential amino acid residues (i.e., amino acid residues which are not critical for the antibody to specifically bind to human IL-6).

Other Anti-IL-6 Antibodies

In certain embodiments, the anti-IL-6 antibody comprises the six CDRs from an antibody selected from the group consisting of siltuximab, gerilimzumab, sirukumab, clazaki-zumab, olokizumab, elsilimomab, VX30 (VOP-R003; Vaccinex), EB-007 (EBI-029; Eleven Bio), ARGX-109 (Ar-GEN-X), FM101 (Femta Pharmaceuticals, Lonza) and ALD518/BMS-945429 (Alder Biopharmaceuticals, Bristol-Myers Squibb). In certain embodiments, the anti-IL-6 antibody comprises the heavy chain V region and light chain V region from an antibody selected from the group consisting of siltuximab, gerilimzumab, sirukumab, clazakizumab, olokizumab, VX30 (VOP-R003; Vaccinex), EB-007 (EBI-029; Eleven Bio), ARGX-109 (ArGEN-X), FM101 (Femta Pharmaceuticals, Lonza) and ALD518/BMS-945429 (Alder Biopharmaceuticals, Bristol-Myers Squibb). In particular embodiments, the anti-IL-6 antibody is an antibody selected from the group consisting of siltuximab, gerilimzumab, sirukumab, clazakizumab, olokizumab, VX30 (VOP-R003; Vaccinex), EB-007 (EBI-029; Eleven Bio), ARGX-109 (Ar-GEN-X), FM101 (Femta Pharmaceuticals, Lonza) and ALD518/BMS-945429 (Alder Biopharmaceuticals, Bristol-Myers Squibb).

In certain embodiments, the anti-IL-6 antibody comprises the six CDRs from an antibody selected from those described in US 2016/0168243, US 2016/0130340, US 2015/0337036, US 2015/0203574, US 2015/0140011, US 2015/0125468, US 2014/0302058, US 2014/0141013, US 2013/0280266, US 2013/0017575, US 2010/0215654, US 2008/0075726, U.S. Pat. No. 5,856,135, US 2006/0240012, US 2006/0257407, or U.S. Pat. No. 7,291,721, the disclosures of which are incorporated herein by reference in their entireties.

Anti-IL-6 Receptor Antibodies

In certain embodiments, the IL-6 antagonist is an anti-IL-6 receptor antibody or antigen-binding fragment or derivative thereof.

In certain embodiments, the IL-6 antagonist is a full-length anti-IL-6 receptor monoclonal antibody. In particular embodiments, the full-length monoclonal antibody is an IgG antibody. In certain embodiments, the full-length monoclonal antibody is an IgG1, IgG2, IgG3, or IgG4 antibody. In certain embodiments, the IL-6 antagonist is a polyclonal composition comprising a plurality of species of full-length anti-IL-6 receptor antibodies, each of the plurality having unique CDRs. In certain embodiments, the IL-6 antagonist is an antibody fragment selected from Fab and Fab' frag-ments. In certain embodiments, the IL-6 antagonist is a scFv, a single domain antibody, including a camelid-derived VHH single domain Nanobody. In certain embodiments, the anti-body is bispecific or multispecific, with at least one of the antigen-binding portions having specificity for IL-6R.

In certain embodiments, the antibody is fully human. In certain embodiments, the antibody is humanized. In certain embodiments, the antibody is chimeric and has non-human V regions and human C region domains. In certain embodi-ments, the antibody is murine.

In typical embodiments, the anti-IL-6 receptor antibody has a $K_D$ for binding human IL-6R of less than 100 nM. In certain embodiments, the anti-IL-6R antibody has a $K_D$ for binding human IL-6R of less than 75 nM, 50 nM, 25 nM, 20 nM, 15 nM, or 10 nM. In particular embodiments, the anti-IL-6 receptor antibody has a $K_D$ for binding human IL-6R of less than 5 nM, 4 nM, 3 nM, or 2 nM. In selected embodiments, the anti-IL-6 receptor antibody has a $K_D$ for binding human IL-6R of less than 1 nM, 750 pM, or 500 pM. In specific embodiments, the anti-IL-6 receptor antibody has a $K_D$ for binding human IL-6R of no more than 500 pM, 400 pM, 300 pM, 200 pM, or 100 pM.

In typical embodiments, the anti-IL-6R reduces the bio-logical activity of IL-6.

In typical embodiments, the anti-IL-6R antibody has an elimination half-life following intravenous administration of at least 7 days. In certain embodiments, the anti-IL-6R antibody has an elimination half-life of at least 14 days, at least 21 days, or at least 30 days.

In certain embodiments, the anti-IL-6R antibody has a human IgG constant region with at least one amino acid substitution that extends serum half-life as compared to the unsubstituted human IgG constant domain.

In certain embodiments, the IgG constant domain com-prises substitutions at residues 252, 254, and 256, wherein the amino acid substitution at amino acid residue 252 is a substitution with tyrosine, the amino acid substitution at amino acid residue 254 is a substitution with threonine, and the amino acid substitution at amino acid residue 256 is a substitution with glutamic acid ("YTE"). See U.S. Pat. No. 7,083,784, incorporated herein by reference in its entirety. In certain extended half-life embodiments, the IgG constant domain comprises substitutions selected from T250Q/

M428L (Hinton et al., J. Immunology 176:346-356 (2006)); N434A (Yeung et al., J. Immunology 182:7663-7671 (2009)); or T307A/E380A/N434A (Petkova et al., International Immunology, 18: 1759-1769 (2006)).

In certain embodiments, the elimination half-life of the anti-IL-6R antibody is increased by utilizing the FcRN-binding properties of human serum albumin. In certain embodiments, the antibody is conjugated to albumin (Smith et al., Bioconjug. Chem., 12: 750-756 (2001)). In certain embodiments, the anti-IL-6R antibody is fused to bacterial albumin-binding domains (Stork et al., Prot. Eng. Design Science 20: 569-76 (2007)). In certain embodiments, the anti-IL-6 antibody is fused to an albumin-binding peptide (Nguygen et al., Prot Eng Design Sel 19: 291-297 (2006)). In certain embodiments, the anti-IL-antibody is bispecific, with one specificity being to IL-6R, and one specificity being to human serum albumin (Ablynx, WO 2006/122825 (bispecific Nanobody)).

In certain embodiments, the elimination half-life of the anti-IL-6R antibody is increased by PEGylation (Melmed et al., Nature Reviews Drug Discovery 7: 641-642 (2008)); by HPMA copolymer conjugation (Lu et al., Nature Biotechnology 17: 1101-1104 (1999)); by dextran conjugation (Nuclear Medicine Communications, 16: 362-369 (1995)); by conjugation with homo-amino-acid polymers (HAPs; HAPylation) (Schlapschy et al., Prot Eng Design Sel 20: 273-284 (2007)); or by polysialylation (Constantinou et al., Bioconjug. Chem. 20: 924-931 (2009)).

In certain embodiments, the anti-IL-6R antibody or antigen-binding portion thereof comprises all six CDRs of tocilizumab. In particular embodiments, the antibody or antigen-binding portion thereof comprises the tocilizumab heavy chain V region and light chain V region. In specific embodiments, the antibody is the full-length tocilizumab antibody.

In certain embodiments, the anti-IL-6R antibody or antigen-binding portion thereof comprises all six CDRs of sarilumab. In particular embodiments, the antibody or antigen-binding portion thereof comprises the sarilumab heavy chain V region and light chain V region. In specific embodiments, the antibody is the full-length sarilumab antibody.

In certain embodiments, the anti-IL-6R antibody or antigen-binding portion thereof comprises all six CDRs of VX30 (Vaccinex), ARGX-109 (arGEN-X), FM101 (Formatech), SA237 (Roche), NI-1201 (NovImmune), or an antibody described in US 2012/0225060.

In certain embodiments, the anti-IL-6R antibody or antigen-binding portion thereof is a single domain antibody. In particular embodiments, the single domain antibody is a camelid VHH single domain antibody. In specific embodiments, the antibody is vobarilizumab (ALX-0061) (Ablynx NV).

Anti-IL-6:IL-6R Complex Antibodies

In certain embodiments, the IL-6 antagonist is an antibody specific for the complex of IL-6 and IL-6R. In certain embodiments, the antibody has the six CDRs of an antibody selected from those described in US 2011/0002936, which is incorporated herein by reference in its entirety.

JAK and STAT Inhibitors

IL-6 is known to signal via the JAK-STAT pathway.

In certain embodiments, the IL-6 antagonist is an inhibitor of the JAK signaling pathway. In certain embodiments, the JAK inhibitor is a JAK1-specific inhibitor. In certain embodiments, the JAK inhibitor is a JAK3-specific inhibitor. In certain embodiments, the JAK inhibitor is a pan-JAK inhibitor.

In certain embodiments, the JAK inhibitor is selected from the group consisting of tofacitinib (Xeljanz), decemotinib, ruxolitinib, upadacitinib, baricitinib, filgotinib, lestaurtinib, pacritinib, peficitinib, INCB-039110, ABT-494, INCB-047986 and AC-410.

In certain embodiments, the IL-6 antagonist is a STAT3 inhibitor. In a specific embodiment, the inhibitor is AZD9150 (AstraZeneca, Isis Pharmaceuticals), a STAT3 antisense molecule.

Additional IL-6 Antagonists

In certain embodiments, the IL-6 antagonist is an antagonist peptide.

In certain embodiments, the IL-6 antagonist is C326 (an IL-6 antagonist by Avidia, also known as AMG220), or FE301, a recombinant protein inhibitor of IL-6 (Ferring International Center S.A., Conaris Research Institute AG). In certain embodiments, the anti-IL-6 antagonist comprises soluble gp130, FE301 (Conaris/Ferring).

Dosage Regimens

Antibodies, Antigen-Binding Fragments, Peptides

In typical embodiments, antibody, antigen-binding fragments, and peptide IL-6 antagonists are administered parenterally.

In some parenteral embodiments, the IL-6 antagonist is administered intravenously. In certain intravenous embodiments, the IL-6 antagonist is administered as a bolus. In certain intravenous embodiments, the IL-6 antagonist is administered as an infusion. In certain intravenous embodiments, the IL-6 antagonist is administered as a bolus followed by infusion. In some parenteral embodiments, the IL-6 antagonist is administered subcutaneously.

In certain embodiments, the antibody, antigen-binding fragment, or peptide IL-6 antagonist is administered in a dose that is independent of patient weight or surface area (flat dose).

In certain embodiments, the intravenous flat dose is 1 mg, 2 mg, 3 mg, 4 mg, 5 mg, 6 mg, 7 mg, 8 mg, 9 mg, or 10 mg. In certain embodiments, the intravenous flat dose is 11 mg, 12 mg, 13 mg, 14 mg, 15 mg, 16 mg, 17 mg, 18 mg, 19 mg, or 20 mg. In certain embodiments, the intravenous flat dose is 25 mg, 30 mg, 40 mg, or 50 mg. In certain embodiments, the intravenous flat dose is 60 mg, 70 mg, 80 mg, 90 mg, or 100 mg. In certain embodiments, the intravenous flat dose is 1-10 mg, 10-15 mg, 15-20 mg, 20-30 mg, 30-40 mg, or 40-50 mg. In certain embodiments, the intravenous flat dose is 1-40 mg, or 50-100 mg.

In certain embodiments, the subcutaneous flat dose is 10 mg, 20 mg, 30 mg, 40 mg, 50 mg, 60 mg, 70 mg, 80 mg, 90 mg, or 100 mg. In certain embodiments, the subcutaneous flat dose is 110 mg, 120 mg, 130 mg, 140 mg, 150 mg, 160 mg, 170 mg, 180 mg, 190 mg, or 200 mg. In certain embodiments, the subcutaneous flat dose is 210 mg, 220 mg, 230 mg, 240 mg, or 250 mg. In certain embodiments, the subcutaneous flat dose is 10-100 mg, 100-200 mg, or 200-250 mg. In certain embodiments, the subcutaneous flat dose is 10-20 mg, 20-30 mg, 30-40 mg, 40-50 mg, 50-60 mg, 60-70 mg, 70-80 mg, 80-90 mg, or 90-100 mg. In certain embodiments, the subcutaneous flat dose is 100-125 mg, 125-150 mg, 150-175 mg, 175-200 mg, or 200-250 mg.

In certain embodiments, the antibody, antigen-binding fragment, or peptide IL-6 antagonist is administered as a patient weight-based dose.

In certain embodiments, the antagonist is administered at an intravenous dose of 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg or 1.0 mg/kg. In certain embodiments, the antagonist is administered at a dose of 1.5 mg/kg, 2 mg/kg, 2.5 mg/kg, 3 mg/kg, 3.5 mg/kg, 4 mg/kg, 4.5 mg/kg, or 5 mg/kg.

In certain embodiments, the subcutaneous weight-based dose is 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg or 1.0 mg/kg. In certain embodiments, the antagonist is adminis- tered at a dose of 1.5 mg/kg, 2 mg/kg, 2.5 mg/kg, 3 mg/kg, 3.5 mg/kg, 4 mg/kg, 4.5 mg/kg, or 5 mg/kg.

In various intravenous embodiments, the IL-6 antagonist is administered once every 7 days, once every 14 days, once every 21 days, once every 28 days, or once a month. In various subcutaneous embodiments, the IL-6 antagonist is administered once every 14 days, once every 28 days, once a month, once every two months (every other month), or once every three months.

In certain preferred embodiments, the IL-6 antagonist is the MEDI5117 antibody. In certain embodiments, MEDI5117 is administered in a flat dose of 1-30 mg IV once every week. In certain embodiments, the MEDI5117 anti- body is administered in a flat dose of 1, 2, 3, 4, 5, 7.5, 10, 15, 20, 25, or 30 mg IV once every week. In certain embodiments, the MEDI5117 antibody is administered in a flat dose of 25-250 mg s.c. once every month to once every three months. In particular embodiments, MEDI5117 is administered at a dose of 30 mg, 45 mg, 60 mg, 75 mg, 100 mg, 120 mg, 125 mg, 150 mg, 175 mg, 200 mg, 225 mg, 240 mg, or 250 mg s.c. once every month, once every two months, or once every 3 months.

In certain embodiments, the IL-6 antagonist is tocili- zumab. In certain embodiments, tocilizumab is administered s.c. in a starting dose for patients ≥100 kg of 162 mg once every week. In certain embodiments, tocilizumab is admin- istered intravenously at a dose of 4 mg/kg once every 4 weeks followed by an increase to 8 mg/kg every 4 weeks based on clinical response.

JAK and STAT Inhibitors

In typical embodiments, small molecule JAK inhibitors and STAT inhibitors are administered orally.

In certain embodiments, the inhibitor is administered once or twice a day at an oral dose of 1-10 mg, 10-20 mg, 20-30 mg, 30-40 mg, or 40-50 mg. In certain embodiments, the inhibitor is administered once or twice a day at a dose of 50-60 mg, 60-70 mg, 70-80 mg, 80-90 mg, or 90-100 mg. In certain embodiments, the inhibitor is administered at a dose of 5, 10, 15, 20, 25, 30, 35, 40, 45, or 50 mg PO once or twice a day. In certain embodiments, the inhibitor is admin- istered at a dose of 75 mg PO QD or BID, 100 mg PO QD or BID.

In certain embodiments, the JAK inhibitor is tofacitinib, and is administered at a dose of 5 mg PO BID or 11 mg PO qDay, In certain embodiments, the JAK inhibitor is decernotinib, and is administered at a dose of 25 mg, 50 mg, 100 mg, or 150 mg PO BID.

In certain embodiments, the inhibitor is ruxolitinib, and is administered at dose of 25 mg PO BID, 20 mg PO BID, 15 mg PO BID, 10 mg PO BID, or 5 mg PO BID.

Treating to Goal

In certain embodiments, the IL-6 antagonist is adminis- tered at a dose, on a schedule, and for a period sufficient to increase diuretic efficiency. In certain of these embodiments, the IL-6 antagonist is administered at a dose, on a schedule, and for a period sufficient to increase diuretic efficiency to normal levels.

In certain embodiments, the IL-6 antagonist is adminis- tered at a dose, on a schedule, and for a period sufficient to increase eGFR, and in certain of these embodiments, the IL-6 antagonist is administered at a dose, on a schedule, and for a period sufficient to increase eGFR to normal levels.

IL-6 Level Monitoring

In certain embodiments, the impact of treatment with IL-6 antagonists on cardiorenal parameters may be monitored by measuring a level of IL-6 in a urine or plasma sample from the patient. It is specifically contemplated that the methods of the invention may be used to monitor the efficacy of treatments for cardiorenal syndrome and may motivate, for example, a change of dose or therapeutic.

Accordingly, in certain embodiments, the method further comprises the subsequent step of determining the level of IL-6 in urine, in plasma, or in both urine and plasma. In certain of these embodiments, the method further comprises a final step of adjusting the dose of at least one subsequent administration of IL-6 antagonist based on IL-6 level deter- mined in the immediately preceding step.

Additional Therapeutic Agents

In certain embodiments of the methods described herein, the method further comprises administering at least one therapeutic agent additional to the IL-6 antagonist, wherein the additional therapeutic agent treats one or more cardio- vascular or renal symptoms of heart failure. Specific treat- ment will be determined on a case by case basis by the attending physician.

Standard Heart Failure Agents

In certain embodiments, the additional therapeutic agent is a diuretic.

In particular embodiments, the diuretic is a loop diuretic. In select embodiments, the loop diuretic is selected from the group consisting of furosemide, torsemide, bumetanide, and ethacrynic acid. In particular embodiments, the loop diuretic is furosemide. In certain embodiments, furosemide is admin- istered orally. In certain embodiments, furosemide is admin- istered intravenously. In certain embodiments, the diuretic is a thiazide diuretic. In particular embodiments, the thiazide diuretic is chlorothiazide, hydrochlorothiazide, chlorthali- done, indapamide, or metolazone. In certain embodiments, the diuretic is a potassium sparing diuretic.

In certain embodiments, the additional therapeutic agent is an ACE inhibitor. In certain embodiments, the ACE inhibitor is selected from the group consisting of benazepril, captopril, enalapril, fosinopril, lisinopril, moexipril, perin- dopril, quinapril, ramipril and trandolapril.

In certain embodiments, the additional therapeutic agent is an angiotensin receptor blocker ("ARB"). In certain embodiments, the ARB is eprosartan, olmesartan, valsartan, telmisartan, losartan, azilsartan medoxomil, candesartan, or irbesartan.

In certain embodiments, the additional therapeutic agent is a β-blocker, a calcium antagonist, or a mineralocorticoid receptor antagonist.

In certain embodiments, the additional therapeutic agent is a natriuretic peptide, such as a B-type natriuretic peptide or N-terminal pro-B-type natriuretic peptide.

In certain embodiments, the additional therapeutic agent is an adenosine antagonist, such as rolofylline.

Specific treatment will be determined on a case-by-case basis by the attending physician.

Nitroxyl Donors

In certain embodiments, the additional therapeutic agent is a nitroxyl donor, and the method further comprises administering a therapeutically effective amount of the nitroxyl donor.

In particular embodiments, the nitroxyl donor is selected from the compounds described in one or more of U.S. Pat. Nos. 9,499,511; 9,487,498; 9,464,061; 9,458,127; 9,221, 780; 9,181,213; 9,156,804; 9,115,064; 9,018,411; 8,987,326; RE45,314; 8,674,132; 8,227,639; and 8,030,356, the disclosures of which are incorporated herein by reference in their entireties.

In selected embodiments, the nitroxyl donor is selected from the compounds described in U.S. Pat. No. RE45,314. In specific embodiments, the nitroxyl donor is selected from the compounds described in U.S. Pat. No. 9,156,804.

Sodium-Free Chloride Supplementation

In certain embodiments, the additional therapeutic agent is a sodium free chloride salt. In certain embodiments, the agent is lysine chloride.

Methods of Improving Treatment of Heart Failure

In another aspect, methods are provided for improving treatment of heart failure by discontinuing therapy that is ineffective, thereby reducing side effects and reducing cost without loss of treatment efficacy. The methods comprise discontinuing administration of an IL-6 antagonist to a patient with heart failure, wherein the patient has been determined to be homozygous for the TMPRSS6 rs855791 minor allele. In one series of embodiments, the patient has previously been determined to be homozygous for the TMPRSS6 rs855791 minor allele. In another series of embodiments, the method further comprises the earlier step of determining that the patient is homozygous for the TMPRSS6 rs855791 minor allele.

In certain embodiments, the patient has elevated pre-treatment urine levels of IL-6. In certain embodiments, the patient has elevated pre-treatment plasma levels of IL-6. In certain embodiments, the patient has elevated pre-treatment urine and elevated pre-treatment plasma levels of IL-6.

In particular embodiments, the patient has cardiorenal syndrome.

Diagnostic, Prognostic, and Treatment Guidance Methods

In another aspect, methods are provided for determining if a subject would benefit from IL-6 antagonist treatment for heart failure. The method comprises measuring a level of IL-6 in a urine sample or plasma sample from the subject, comparing the measured level of IL-6 to a predetermined reference level, and determining whether or not the measured level of IL-6 is greater than the corresponding reference level, wherein when the measured level of IL-6 is greater than the corresponding reference level, IL-6 antagonist treatment is recommended.

IL-6 may be measured in plasma or in urine according to the methods set forth in Section 6.3.2.3 above. Reference levels for IL-6 in urine and plasma may be determined by measuring IL-6 levels in a reference population. A person of skill in the art is able to determine a reference level for the level of a biomarker in a population based on clinical experience and common levels of the biomarker in samples from the population.

Figures 3A, 3B:
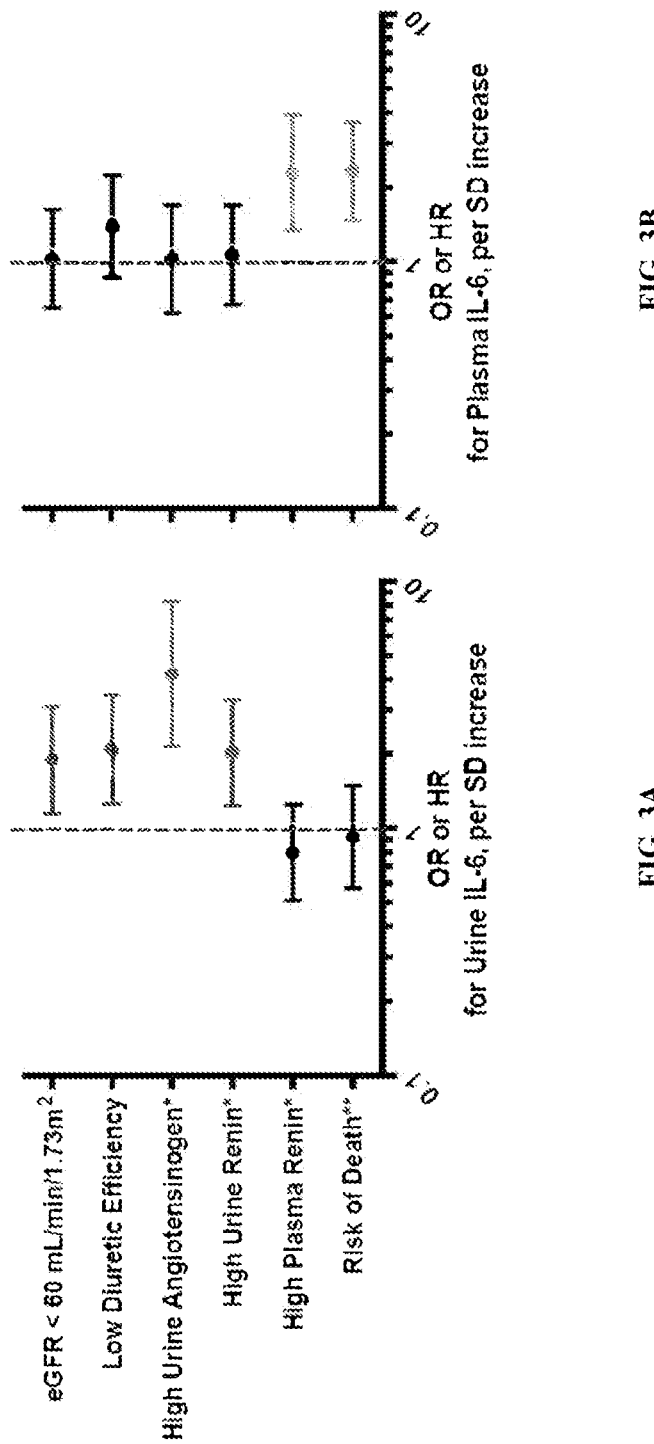
FIGS. 3A and 3B plot the association in a 98 patient subset of the 129 patients reported in FIGS. 1 and 2 of (A) Urine IL-6 levels and (B) Plasma IL-6 levels with the following clinical determinations: Reduced kidney function, low diuretic efficiency ("DE"), increased neurohormonal activation, and risk of mortality. Whiskers represent 95% confidence interval ("CI"). All analyses adjusted for both urine and plasma levels of IL-6. Urine IL-6 levels are indexed to urinary creatinine. Due to the skewed distribution of urine and plasma IL-6 variables, a log transform was applied before performing logistic and Cox regressions. Abbreviations: OR=Odds ratio. HR=Hazards ratio. IL=interleukin. SD=standard deviation. eGFR=estimated glomerular filtration rate. *=adjusted for use of angiotensin converting enzyme inhibitor (ACE-I) or angiotensin receptor blocker (ARB). **=adjusted for baseline characteristics including age, race, amino terminal pro B-type natriuretic peptide (NT-proBNP), use of ACE-I or ARB, home loop diuretic dose, and eGFR.

In further aspects, methods are provided for determining if a subject is in need of IL-6 antagonist treatment for impaired glomerular filtration, low diuretic efficiency, high urine angiotensin, high plasma renin, or is at risk of mortality due to cardiorenal syndrome using the above described method. As shown in FIG. 3 and discussed in Example 1 hereinbelow, high levels of IL-6 in urine or plasma are associated with these parameters.

Kits

In a further aspect, a kit is provided. In general, kits will comprise detection reagents that are suitable for detecting the presence of biomarkers of interest and with instructions for use in accordance with the methods of the invention. The kit may comprise antibodies or other immunohistochemical reagents capable of binding to IL-6. The kit may contain capture and detection antibodies suitable for performing an ELISA for measuring IL-6 in urine or plasma. In certain embodiments the kit may contain tools and reagents for preparing urine and plasma samples for the ELISA or for indexing IL-6 in urine to the concentration of another biomarker, in certain embodiments IL-6 is indexed against creatinine.

Further Embodiments

Further embodiments are provided in the following numbered embodiments.

1. A method of treating heart failure, comprising:
   administering a therapeutically effective amount of an IL-6 antagonist to a patient with heart failure,
   wherein the patient has been determined to have at least one copy of the TMPRSS6 rs855791 major allele.
2. The method of embodiment 1, wherein the patient has previously been determined to have at least one copy of the TMPRSS6 rs855791 major allele.
3. The method of embodiment 1, further comprising the earlier step of: determining that the patient has at least one copy of the TMPRSS6 rs855791 major allele.
4. The method of any one of embodiments 1-3, wherein the patient has elevated pre-treatment urine levels of IL-6.
5. The method of any one of embodiments 1-4, wherein the patient has elevated pre-treatment plasma levels of IL-6.
6. The method of any one of embodiments 1-5, wherein the patient has acute heart failure.
7. The method of any one of embodiments 1-5, wherein the patient has chronic heart failure.
8. The method of any one of embodiments 1-7, wherein the patient has cardiorenal syndrome.
9. The method of embodiment 8, wherein the patient has cardiorenal syndrome type 4.
10. The method of any one of embodiments 1-9, wherein the patient has diuretic resistant heart failure.
11. The method of embodiment 10, wherein the patient's diuretic efficiency is less than 95.
12. The method of embodiment 11, wherein the patient's diuretic efficiency is less than 90.
13. The method of embodiment 12, wherein the patient's diuretic efficiency is less than 85.
14. The method of embodiment 13, wherein the patient's diuretic efficiency is less than 80.
15. The method of embodiment 14, wherein the patient's diuretic efficiency is less than 75.
16. The method of embodiment 15, wherein the patient's diuretic efficiency is less than 70.
17. The method of embodiment 16, wherein the patient's diuretic efficiency is less than 65.
18. The method of any one of embodiments 1-17, wherein the IL-6 antagonist is an anti-IL-6 antibody, or antigen-binding fragment or derivative thereof.
19. The method of embodiment 18, wherein the anti-IL-6 antibody or antigen-binding fragment or derivative has a $K_D$ for binding human IL-6 of less than 100 nM.
20. The method of embodiment 19, wherein the antibody or antigen-binding fragment or derivative has a $K_D$ for binding human IL-6 of less than 50 nM.
21. The method of embodiment 20, wherein the antibody or antigen-binding fragment or derivative has a $K_D$ for binding human IL-6 of less than 10 nM.

22. The method of embodiment 21, wherein the antibody or antigen-binding fragment or derivative has a $K_D$ for binding human IL-6 of less than 1 nM.

23. The method of any one of embodiments 18-22, wherein the anti-IL-6 antibody or antigen-binding fragment or derivative has an elimination half-life following intravenous administration of at least 7 days.

24. The method of embodiment 23, wherein the anti-IL-6 antibody or antigen-binding fragment or derivative has an elimination half-life following intravenous administration of at least 14 days.

25. The method of embodiment 24, wherein the anti-IL-6 antibody or antigen-binding fragment or derivative has an elimination half-life following intravenous administration of at least 21 days.

26. The method of embodiment 25, wherein the anti-IL-6 antibody or antigen-binding fragment or derivative has an elimination half-life following intravenous administration of at least 30 days.

27. The method of any one of embodiments 18-26, wherein the IL-6 antagonist is a full-length monoclonal anti-IL-6 antibody.

28. The method of embodiment 27, wherein the antibody is an IgG1 or IgG4 antibody.

29. The method of embodiment 28, wherein the antibody is an IgG1 antibody.

30. The method of any one of embodiments 18-29, wherein the anti-IL-6 antibody or antigen-binding fragment or derivative is fully human.

31. The method of any one of embodiments 18-29, wherein the anti-IL-6 antibody or antigen-binding fragment or derivative is humanized.

32. The method of any one of embodiments 18-31, wherein the anti-IL-6 antibody or antigen-binding fragment or derivative comprises all six variable region CDRs of MED5117.

33. The method of embodiment 32, wherein the antibody comprises the VH and VL of MED5117.

34. The method of embodiment 33, wherein the antibody is MED5117.

35. The method of any one of embodiments 18-31, wherein the anti-IL-6 antibody or antigen-binding fragment or derivative comprises all six variable region CDRs of an antibody selected from the group consisting of siltuximab, gerilimzumab, sirukumab, clazakizumab, olokizumab, elsilimomab, VX30 (VOP-R003; Vaccinex), EB-007 (EBI-029; Eleven Bio), ARGX-109 (ArGEN-X), FM101 (Femta Pharmaceuticals, Lonza) and ALD518/BMS-945429 (Alder Biopharmaceuticals, Bristol-Myers Squibb).

36. The method of embodiment 35, wherein the anti-IL-6 antibody or antigen-binding fragment or derivative comprises the heavy chain V region and light chain V region from an antibody selected from the group consisting of siltuximab, gerilimzumab, sirukumab, clazakizumab, olokizumab, VX30 (VOP-R003; Vaccinex), EB-007 (EBI-029; Eleven Bio), ARGX-109 (ArGEN-X), FM101 (Femta Pharmaceuticals, Lonza) and ALD518/BMS-945429 (Alder Biopharmaceuticals, Bristol-Myers Squibb).

37. The method of embodiment 36, wherein the anti-IL-6 antibody or antigen-binding fragment or derivative is an antibody selected from the group consisting of siltuximab, gerilimzumab, sirukumab, clazakizumab, olokizumab, VX30 (VOP-R003; Vaccinex), EB-007 (EBI-029; Eleven Bio), ARGX-109 (ArGEN-X), FM101 (Femta Pharmaceuticals, Lonza) and ALD518/BMS-945429 (Alder Biopharmaceuticals, Bristol-Myers Squibb).

38. The method of any one of embodiments 18-26, wherein the IL-6 antagonist is a single domain antibody, a Vim Nanobody, an Fab, or a scFv.

39. The method of any one of embodiments 1-17, wherein the IL-6 antagonist is an anti-IL-6R antibody, or antigen-binding fragment or derivative thereof 40. The method of embodiment 39, wherein the anti-IL-6R antibody, antigen-binding fragment, or derivative comprises the 6 CDRs of tocilizumab.

41. The method of embodiment 39, wherein the anti-IL-6R antibody, antigen-binding fragment, or derivative comprises the 6 CDRs of vobarilizumab.

42. The method of any one of embodiments 1-17, wherein the IL-6 antagonist is a JAK inhibitor.

43. The method of embodiment 42, wherein the JAK inhibitor is selected from the group consisting of tofacitinib (Xeljanz), decemotinib, ruxolitinib, upadacitinib, baricitinib, filgotinib, lestaurtinib, pacritinib, peficitinib, INCB-039110, ABT-494, INCB-047986 and AC-410.

44. The method of any one of embodiments 1-17, wherein the IL-6 antagonist is a STAT3 inhibitor.

45. The method of any one of embodiments 18-41, wherein the IL-6 antagonist is administered parenterally.

46. The method of embodiment 45, wherein the IL-6 antagonist is administered subcutaneously.

47. The method of any one of embodiments 42 or 43, wherein the IL-6 antagonist is administered orally.

48. The method of any one of embodiments 1-47, wherein the IL-6 antagonist is administered at a dose, on a schedule, and for a period sufficient to increase diuretic efficiency.

49. The method of embodiment 48, wherein the IL-6 antagonist is administered at a dose, on a schedule, and for a period sufficient to increase diuretic efficiency to normal levels.

50. The method of any one of embodiments 1-49, wherein the IL-6 antagonist is administered at a dose, on a schedule, and for a period sufficient to increase eGFR.

51. The method of embodiment 50, wherein the IL-6 antagonist is administered at a dose, on a schedule, and for a period sufficient to increase eGFR to normal levels.

52. The method of any one of embodiments 1-51, further comprising the subsequent step of determining the level of IL-6 in urine.

53. The method of any one of embodiments 1-51, further comprising the subsequent step of determining the level of IL-6 in plasma.

54. The method of any one of embodiments 1-51, further comprising the subsequent step of determining the level of IL-6 in urine and in plasma.

55. The method of any one of embodiments 52-54, further comprising a final step of adjusting the dose of IL-6 antagonist for subsequent administration based on IL-6 level determined in the immediately preceding step.

56. A method of determining if a subject requires treatment for cardiorenal syndrome, the method comprising:
   a) measuring a level of IL-6 in a urine or plasma sample from the subject,
   b) comparing the measured level of IL-6 to a predetermined reference level, c) determining whether or not the measured level of IL-6 is greater than the corresponding reference level, wherein when the measured level of IL-6 is greater than the corresponding reference level, the subject has cardiorenal syndrome, and treatment is recommended.

57. A method of determining if a subject requires treatment for impaired glomerular filtration, comprising:
a) measuring a level of IL-6 in a urine sample from the subject,
b) comparing the measured level of IL-6 to a predetermined reference level,
c) determining whether or not the measured level of IL-6 is greater than the corresponding reference level, wherein when the measured level of IL-6 is greater than the corresponding reference level, the subject has impaired glomerular filtration, and treatment is recommended.

58. A method of determining if a subject requires treatment for low diuretic efficiency, comprising:
a) measuring a level of IL-6 in a urine sample from the subject,
b) comparing the measured level of IL-6 to a predetermined reference level,
c) determining whether or not the measured level of IL-6 is greater than the corresponding reference level, wherein when the measured level of IL-6 is greater than the corresponding reference level, the subject has low diuretic efficiency, and treatment is recommended.

59. A method of determining if a subject requires treatment for high urine angiotensin, comprising:
a) measuring a level of IL-6 in a urine sample from the subject,
b) comparing the measured level of IL-6 to a predetermined reference level,
c) determining whether or not the measured level of IL-6 is greater than the corresponding reference level, wherein when the measured level of IL-6 is greater than the corresponding reference level, the subject has high urine angiotensin, and treatment is recommended.

60. A method of determining if a subject requires treatment for high plasma renin, comprising:
a) measuring a level of IL-6 in a plasma sample from the patient,
b) comparing the measured level of IL-6 to a predetermined reference level,
c) determining whether or not the measured level of IL-6 is greater than the corresponding reference level, wherein when the measured level of IL-6 is greater than the corresponding reference level, the subject has high plasma renin, and treatment is recommended.

61. A method of determining if a subject is at risk of mortality due to cardiorenal syndrome and requires treatment, comprising:
a) measuring a level of IL-6 in a plasma sample from the patient,
b) comparing the measured level of IL-6 to a predetermined reference level, c) determining whether or not the measured level of IL-6 is greater than the corresponding reference level, wherein when the measured level of IL-6 is greater than the corresponding reference level, the subject is at risk of mortality due to cardiorenal syndrome, and treatment is recommended.

62. The method of any one of embodiments 56-61, wherein the patient is a heart failure patient.

63. The method of any of embodiments 56-62, wherein the level of IL-6 is measured using an enzyme-linked immunosorbent assay (ELISA).

64. A method of treating cardiorenal syndrome in a patient comprising:
a) measuring a level of IL-6 in a urine sample or a plasma sample from the patient,
b) comparing the measured level of IL-6 to a predetermined reference level,
c) determining whether or not the measured level of IL-6 is greater than the corresponding reference level wherein when the measured level of IL-6 is greater than the corresponding reference level, treatment for cardiorenal syndrome is administered.

65. The method of embodiment 64, wherein the patient is a heart failure patient.

66. The method of embodiment 64 or embodiment 65, wherein the level of IL-6 is measured using an enzyme-linked immunosorbent assay (ELISA).

67. The method of any one of embodiments 64-66, wherein the treatment administered for cardiorenal syndrome comprises administering one or more of at least one diuretic, angiotensin-converting-enzyme inhibitor, angiotensin receptor blocker, natriuretic peptide, adenosine antagonist, an IL-6 antagonist, or any combination thereof.

68. The method of embodiment 67, wherein treating cardiorenal syndrome comprises administering at least one anti-IL-6 antibody or anti-IL-6R antibody.

69. A kit comprising reagents for an assay for measuring a level of IL-6 and written instructions, the written instructions comprising:
a) measuring a level of IL-6 in a urine or plasma sample from the subject,
b) comparing the measured level of IL-6 to a predetermined reference level,
c) determining whether or not the measured level of IL-6 is greater than the corresponding reference level, wherein when the measured level of IL-6 is greater than the corresponding reference level, the subject has cardiorenal syndrome, and treatment is recommended.

70. The kit of embodiment 69, wherein the instructions direct the kit for use on a heart failure patient.

71. The kit of embodiment 69 or 70, wherein the kit contains reagents for measuring the level of IL 6 using an enzyme-linked immunosorbent assay (ELISA).

Experimental Examples

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, practice the claimed methods of the present invention. The following working examples therefore, specifically point out the preferred embodiments of the present invention, and are not to be construed as limiting in any way the remainder of the disclosure.

The materials and methods employed in the experiments disclosed herein are now described.

Example 1: Urine and Plasma IL-6 Associations in Heart Failure Patients

Methods. Consecutive heart failure ("HF") patients receiving high dose diuretic therapy at the Yale Transitional Care Clinic (YTCC) were enrolled in the prospective observational study.

The YTCC is an outpatient clinic with a focus on diuretic and fluid status management. Patients present for 4-8 hours of treatment, during which they receive 1-3 doses of loop diuretic. The dosing protocol is determined by patient fluid status; the choice of oral (PO) torsemide or intravenous (IV) bumetanide is at the discretion of the treating physician. During the treatment period all urine produced is saved in a cumulative collection container and sent to the clinical laboratory for electrolyte measurements at the conclusion of the visit. A cumulative urine collection is conducted during the treatment period. Additional spot urine samples are saved both before and one hour after diuretic administration.

Assays. A Randox RxDaytona™ automated clinical chemistry analyzer was used to measure urine and serum electrolytes using ion selective electrodes. Urea, creatinine, bicarbonate and cystatin C were measured using Randox reagents per the manufacturer's instructions (Randox Laboratories™, UK). Concentrations of interleukin 10 and IL-6 were measured using the MesoScale Discovery (MSD) platform (Meso Scale Diagnostics™, Gaithersburg, MD, USA). Levels of amino terminal pro B-type natriuretic peptide (NT-proBNP) were measured at the Yale clinical laboratory on a Roche Elecsys 120 analyzer (Roche Diagnostics, Indianapolis, USA). Plasma renin activity (PRA), angiotensinogen and active renin were measured using commercially available competitive ELISA kits from ALPCO™ per manufacturer's instructions (ALPCO™, Salem, NH, USA). Total renin was also analyzed using commercially available ELISA kits (R&D Systems™, Minneapolis, USA). The total renin immunoassay kit from R&D Systems™ recognizes both active renin and prorenin. The assay's mean detectable limit is 4.43 pg/ml for total renin and 0.81 pg/ml for active renin. Liquid chromatography mass spectrometry was used to measure levels of bumetanide and torsemide in urine. Ultra-high performance liquid chromatography was performed on the Agilent Infinity 1290 UPLC System™. Chromatographic separation was achieved on the Zorbax Bonus RP™ 2.1×50 mm 1.8μ column with a flow rate of 0.6 ml/min. The mobile phase contained of 0.1% Formic acid (Buffer A) and 80% acetonitrile in 0.1% Formic acid (Buffer B). Mass spectrometry was performed on Agilent Q-TOF System™ (Agilent™, Santa Clara, CA, USA) in positive ion mode.

Calculations and Definitions. eGFR was calculated using the Chronic Kidney Disease Epidemiology Collaboration (CKD-EPI) formula. Doses of loop diuretics were converted to furosemide equivalents with 1 mg bumetanide=20 mg torsemide=40 mg intravenous furosemide=80 mg oral furosemide. As published previously, diuretic efficiency was defined as the increase in urinary sodium output over the treatment period per each doubling of the loop diuretic dose, centered on 40 mg of furosemide equivalents; this scale was chosen to account for the sigmoidal dose-response curve of these drugs. Urinary diuretic excretion was calculated by multiplying the concentration of diuretic in the urine by the volume of urine produced in the first 3 hours after diuretic administration; this quantity of estimated diuretic was then normalized to the administered diuretic dose in furosemide equivalents, taking into account the published urinary clearance of the particular diuretic received by the patient (bumetanide or torsemide). Fractional excretions of sodium and potassium were calculated using the formula: Fractional excretion of X (FEX)=[X]Urine*[Creatinine]Serum/([X] Serum or plasma*[Creatinine]Urine). Urine proteins including renin, angiotensinogen and IL-6 were indexed to urinary creatinine. A low urine IL-6 was defined as a value less than the median of 14.2 pg/g of urinary creatinine. A low plasma IL-6 was defined as a value less than the median of 2.0 pg/mL. High levels of urine and plasma renin and angiotensinogen were defined as values greater than or equal to the cohort medians of these variables.

Statistical Analysis. Values reported are mean+/−SD, median (quartile 1-quartile 3) and percentage. Correlations between continuous variables are Spearman's rho with the exception of adjusted correlations. Pearson's chi-squared test was used to compare categorical variables between groups. To compare continuous variables between groups, either Student's t-test or the Wilcoxon Rank Sum test was used. A log transformation was applied to skewed variables including plasma IL-6, urine IL-6 and NT-pro-BNP before entering them into multivariable models and partial correlation analyses. Logistic regression was used to evaluate association between the odds of low diuretic efficiency, an eGFR <60 mL/min/1.73 m$^2$, or high levels of urine or plasma neurohormonal parameters with plasma and urine levels of IL-6, both on a univariate level and with adjustment for plasma or urine IL-6 and/or eGFR. Cox proportional hazards modeling was used to evaluate time-to-event associations with all-cause mortality. Statistical analysis was performed with IBM SPSS Statistics version 23 (IBM Corp., Armonk, NY) and Stata version 13 (StataCorp™, College Station, TX). Statistical significance was defined as 2-tailed $p<0.05$ for all analyses.

The baseline characteristics of our population are described in Table 2, below. In this subset, 98 patients underwent determination of IL-6 levels in blood and urine. The median (IQR) pre-diuretic level of urine IL-6 was 14.2 pg/g of creatinine (5.6-36.2 pg/g) whereas the median level of plasma IL-6 was 2.0 pg/mL (1.2-3.9 pg/mL). Plasma and urine IL-6 levels were only modestly correlated (r=0.40, p<0.001). Notably, those with lower than median levels of urine IL-6 tended to be younger, Caucasian, more often on angiotensin receptor blocker (ARB) or angiotensin converting enzyme (ACE-I) therapy, more likely to have heart failure with reduced ejection fraction (HFrEF), a higher GFR and substantially lower plasma levels of NT-proBNP levels. The profile of patients defined by a lower than median plasma IL-6 was somewhat different, but largely reflected the same trends.

TABLE 2

| Baseline Characteristics | | | | | | | |
|---|---|---|---|---|---|---|---|
| | Overall Cohort (n = 98) | Low Urine IL-6 (n = 49) | High Urine IL-6 (n = 49) | p-value | Low Plasma IL-6 (n = 49) | High Plasma IL-6 (n = 49) | p-value |
| Demographics | | | | | | | |
| Age | 67.9 ± 13.5 | 62.1 ± 13.2 | 73.8 ± 11.2 | <0.001* | 65.8 ± 15.1 | 70.1 ± 11.5 | 0.12 |
| Black race, % | 36 | 57 | 15 | <0.001* | 47 | 26 | 0.04* |
| Male sex, % | 44 | 49 | 39 | 0.31 | 49 | 39 | 0.31 |
| Past Medical History, % | | | | | | | |
| Hypertension | 91 | 94 | 88 | 0.29 | 96 | 86 | 0.08 |
| Diabetes | 47 | 55 | 39 | 0.11 | 37 | 57 | 0.04* |
| Gout | 13 | 10 | 16 | 0.37 | 10 | 16 | 0.37 |
| Ischemic etiology | 30 | 33 | 27 | 0.46 | 33 | 27 | 0.46 |
| Post-discharge follow-up visit | 63 | 71 | 55 | 0.09 | 61 | 65 | 0.68 |
| Baseline Medications, % | | | | | | | |
| ACEI or ARB | 55 | 65 | 45 | 0.04* | 67 | 43 | 0.02* |
| Beta-blocker | 77 | 82 | 71 | 0.23 | 82 | 71 | 0.23 |
| Thiazide-type diuretic | 14 | 12 | 16 | 0.56 | 6 | 22 | 0.02* |
| MRA | 33 | 37 | 29 | 0.39 | 31 | 35 | 0.67 |
| Digoxin | 10 | 12 | 8 | 0.50 | 8 | 12 | 0.50 |
| Home loop diuretic dose (mg furosemide equivalents) | 80 (60-160) | 80 (60-160) | 100 (80-160) | 0.60 | 80 (40-120) | 160 (80-200) | 0.002* |
| Physical Exam | | | | | | | |
| Weight (kg) | 98.2 ± 33.4 | 106.0 ± 37.9 | 90.4 ± 26.4 | 0.02* | 98.4 ± 31.5 | 98.0 ± 35.5 | 0.95 |
| BMI | 34.8 ± 10.8 | 36.7 ± 11.3 | 32.5 ± 9.9 | 0.09 | 33.5 ± 8.4 | 36.2 ± 13.0 | 0.28 |
| Systolic blood pressure (mmHg) | 122.6 ± 18.9 | 120.6 ± 19.1 | 124.5 ± 18.7 | 0.32 | 123.4 ± 18.9 | 121.7 ± 19.1 | 0.65 |
| Heart rate (beats per minute): | 75.9 ± 13.2 | 75.6 ± 13.2 | 76.2 ± 13.4 | 0.82 | 74.9 ± 13.3 | 76.8 ± 13.2 | 0.48 |
| Echocardiogram | | | | | | | |
| Left ventricular ejection fraction (%) | 45 (27-56) | 35 (25-50) | 51 (31-59) | 0.03* | 39 (29-54) | 45 (26-57) | 0.56 |
| Ejection fraction ≥40% | 53% | 43% | 63% | 0.04* | 49% | 57% | 0.42 |
| Laboratory Values | | | | | | | |
| Sodium (mmol/L) | 136 (134-140) | 137 (134-138) | 139 (134-141) | 0.06 | 138 (135-140) | 136 (132-140.0) | 0.12 |
| Chloride (mmol/L) | 96 (95-102) | 100 (96-102) | 98 (95-102) | 0.50 | 101 (98-103) | 96 (91-101) | <0.001* |
| Hypochloremia, % | 34 | 27 | 42 | 0.13 | 14 | 55 | <0.001* |
| Potassium (mmol/L) | 4.1 (3.7-4.5) | 4.2 (3.8-4.6) | 4.1 (3.6-4.3) | 0.053 | 4.1 (3.7-4.5) | 4.1 (3.7-4.4) | 0.64 |
| Bicarbonate (mmol/L) | 23.9 (21.7-26.4) | 23.1 (21.6-25.3) | 24.9 (22.2-27.9) | 0.03* | 23.1 (21.5-25.2) | 25.0 (22.6-28.0) | 0.03* |
| Blood urea nitrogen (mg/dL) | 29.0 (20.0-47.0) | 27.0 (17.5-44.0) | 32.0 (24.0-48.0) | 0.10 | 27.0 (19.0-39.0) | 36.0 (23.0-65.0) | 0.04* |
| Serum creatinine (mg/dL) | 1.5 ± 0.8 | 1.4 ± 0.6 | 1.7 ± 0.9 | 0.046* | 1.3 ± 0.5 | 1.8 ± 1.0 | 0.007* |
| BUN/Creatinine ratio | 24.0 ± 8.3 | 24.1 ± 8.1 | 23.9 ± 8.5 | 0.92 | 23.6 ± 8.0 | 24.5 ± 8.5 | 0.58 |
| Estimated glomerular filtration rate (eGFR) (mL/min/1.73 m$^2$) | 54.9 ± 28.2 | 64.3 ± 30.1 | 45.7 ± 22.8 | <0.001* | 61.4 ± 27.2 | 48.3 ± 27.8 | 0.02* |
| eGFR <60 mL/min/1.73 m$^2$ | 61% | 48% | 73% | 0.01* | 55% | 67% | 0.24 |
| Albumin (g/dL) | 3.8 ± 0.4 | 3.9 ± 0.4 | 3.8 ± 0.4 | 0.045* | 4.0 ± 0.4 | 3.7 ± 0.4 | <0.001* |
| Hemoglobin (g/dL) | 12.2 ± 2.3 | 12.7 ± 2.2 | 11.7 ± 2.3 | 0.04* | 12.8 ± 2.0 | 11.5 ± 2.4 | 0.004* |
| Diuretic Parameters | | | | | | | |
| Diuretic dose administered (mg furosemide equivalents) | 140 (40-240) | 80 (40-160) | 160 (80-280) | 0.001* | 80 (40-160) | 160 (80-320) | <0.001* |
| Diuretic administered, % | | | | | | | |
| IV Bumetanide: | 45 | 27 | 63 | <0.001* | 33 | 57 | 0.02* |
| Torsemide: | 55 | 73 | 37 | | 67 | 43 | |

ACE-I = angiotensin-converting enzyme inhibitor.

ARB = angiotensin receptor blocker.

MRA = mineralocorticoid receptor antagonist.

IL = interleukin

BUN = blood urea nitrogen.

BNP = brain natriuretic peptide.

BMI = body mass index.

*p < 0.05.

TABLE 3

| | Overall Cohort (n = 98) | Low Urine IL-6 (n = 49) | High Urine IL-6 (n = 49) | p-value | Low Plasma IL-6 (n = 49) | High Plasma IL-6 (n= 49) | p-value |
|---|---|---|---|---|---|---|---|
| | | | Plasma and Urine Biomarkers at Baseline | | | | |
| Plasma Biomarkers | | | | | | | |
| IL-6 (pg/mL) | 2.0 (1.2-3.9) | 1.4 (0.9-2.9) | 2.8 (1.5-6.1) | <0.001* | 1.2 (0.9-1.4) | 3.9 (2.9-6.8) | <0.001* |
| IL-10 (pg/mL) | 0.3 (0.2-0.7) | 0.3 (0.2-0.4) | 0.5 (0.3-0.8) | 0.001* | 0.3 (0.2-0.5) | 0.5 (0.3-0.8) | 0.01* |
| IL-10/IL-6 ratio | 0.2 (0.1-0.4) | 0.2 (0.1-0.3) | 0.2 (0.1-0.4) | 0.73 | 0.3 (0.2-0.6) | 0.1 (0.1-0.2) | <0.001* |
| Total renin (pg/mL) | 1167.7 (734.7-2759.7) | 1169.2 (734.7-3013.5) | 1166.3 (816.0-2390.9) | 0.97 | 909.6 (595.2-1517.9) | 1784.4 (921.6-3868.7) | <0.001* |
| Active renin (pg/mL) | 36.8 (8.4-162.8) | 79.0 (7.7-184.2) | 28.1 (12.0-139.4) | 0.38 | 13.0 (4.4-160.7) | 49.1 (15.7-169.2) | 0.07 |
| Angiotensinogen (ng/mL) | 167.9 (54.1, 445.3) | 193.9 (48.2, 518.1) | 160.3 (58.3, 430.2) | 0.81 | 178.8 (31.6, 481.2) | 167.2 (75.5, 445.3) | 0.50 |
| NT pro-BNP (pg/mL) | 1825.0 (681.0-5030.0) | 840.0 (256.0-3115.0) | 3115.0 (1440.0-6070.0) | <0.001* | 1440.0 (412.0-3010.0) | 3390.0 (792.0-6410.0) | 0.01* |
| Urine Biomarkers | | | | | | | |
| IL-6 (pg/g of creatinine) | 14.2 (5.6-36.2) | 5.6 (2.5-7.7) | 36.2 (20.7-68.9) | <0.001* | 7.0 (3.2-19.1) | 21.2 (9.2-45.3) | <0.001* |
| IL-6 (pg/mL) | 1.2 (0.5-2.6) | 0.5 (0.2-0.7) | 2.5 (1.6-4.0) | <0.001* | 0.8 (0.4-1.9) | 1.7 (0.6-3.2) | 0.03* |
| Renin (pg/mg of creatinine) | 0.3 (0.1-0.8) | 0.2 (0.1-0.5) | 0.6 (0.3-1.2) | <0.001* | 0.2 (0.1-0.6) | 0.5 (0.2-1.5) | <0.001* |
| Renin (pg/mL) | 28.2 (10.2-88.3) | 19.9 (7.5-53.1) | 37.0 (13.4-109.6) | 0.01* | 23.7 (7.5-53.1) | 35.9 (12.3-109.6) | 0.06 |
| Angiotensinogen (pg/mg creatinine) | 18.7 (5.4-126.3) | 6.2 (3.3-19.0) | 123.5 (17.3-549.7) | <0.001* | 7.3 (3.7-39.7) | 33.7 (12.3-318.9) | 0.002* |
| Angiotensinogen (pg/mL) | 1530 (624-10941) | 966 (231-1567) | 5850 (1518-53865) | <0.001* | 1105 (463-5801) | 2153 (966-23952) | 0.02* |
| $FE_{Na}$ (%) | 0.5 (0.2-1.3) | 0.4 (0.2-1.2) | 0.5 (0.2-1.4) | 0.22 | 0.4 (0.1-1.0) | 0.7 (0.3-1.8) | 0.02* |
| $FE_K$ (%) | 18.4 (11.7-39.3) | 15.5 (9.9-32.5) | 21.6 (15.2-44.6) | 0.02* | 15.8 (9.6-24.5) | 24.5 (13.9-50.3) | 0.001* |
| $FE_{Urea}$ (%) | 63.6 (44.8-81.3) | 59.5 (44.4-80.5) | 65.5 (44.9-81.6) | 0.62 | 66.7 (47.5-82.8) | 58.2 (44.6-76.0) | 0.20 |

IL = interleukin.
NT pro-BNP = N-terminal pro b-type natriuretic peptide.
$FE_{Na}$ = fractional excretion of sodium.
$FE_K$ = fractional excretion of potassium.
$FE_{Urea}$ = fractional excretion of urea.

Kidney Function and IL-6

As shown in Table 2, eGFR was lower in patients with high urine or plasma IL-6, but this association was only significant between eGFR and urine IL-6 (p=0.01). A correlation between both plasma IL-6 and eGFR (r=−0.26, p=0.01) as well as urine IL-6 and eGFR (r=−0.38, p<0.001) was observed. However, on adjustment for urine IL-6, there was no longer a significant association between plasma IL-6 and eGFR (p=0.20), whereas a significant association remained between urine IL-6 and eGFR after adjustment for plasma IL-6 (partial r=−0.32, p=0.002). Similarly, the risk of reduced eGFR as defined by an eGFR <60 mL/min/1.73 m² was increased with higher levels of urine IL-6 (OR=1.9 per SD increase, 95% CI=1.2, 3.1, p=0.006) and not with higher levels of plasma IL-6 (OR=1.3 per SD increase, 95% CI=0.8-2.0, p=0.25).

Diuretic Response and IL-6

There was an inverse association between diuretic efficiency and both urine IL-6 (r=−0.43, p<0.001) and plasma IL-6 (r=−0.31, p=0.002; FIG. 3). Odds for a low diuretic efficiency increased with higher levels of either urine IL-6 (OR=2.3 per SD increase, 95% CI 1.4-3.8, p=0.001) or plasma IL-6 (OR=1.7 per SD increase, 95% CI=1.1-2.7, p=0.02). Upon adjustment for eGFR, only urine IL-6 remained significantly associated with risk of low diuretic efficiency (adjusted OR=1.8 per SD increase, 95% CI 1.1-3.1, p=0.02; FIG. 3). Furthermore, when urine IL-6 and plasma IL-6 were both entered into a logistic regression model, only urine IL-6 remained associated with risk of low diuretic efficiency (adjusted OR=2.1 per SD increase, 95% CI 1.3-3.5, p=0.004) while plasma IL-6 showed no such association (OR=1.4, 95% CI 0.9-2.2, p=0.17).

Neurohormonal Activation

Plasma IL-6 was associated with higher levels of plasma renin (Table 3 and FIG. 3). Notably, higher levels of plasma IL-6 conferred additional risk of high plasma total renin (OR=1.9 per SD increase, 95% CI 1.2-3.0, p=0.008), and this persisted despite adjustment for use of ACE-I or ARB and urine IL-6 levels (adjusted OR=2.3 per SD increase, 95% CI 1.3-3.9, p=0.003). Urine IL-6 was not associated with increased risk of high plasma renin (OR=1.0, 95% CI 0.7-1.5, p=0.98).

Urine IL-6 was strongly associated with high levels of tissue level RAAS activation as measured by urine angiotensinogen (OR=4.2 per SD increase, 95% CI 2.2-7.9, p<0.001) and urine renin (OR=2.1 per SD increase, 95% CI 1.3-3.4, p=0.002; FIG. 3). These associations persisted after adjustment for plasma IL-6 levels and ACE-I or ARB use (adjusted OR for high urine angiotensinogen=4.2 per SD increase, 95% CI 2.2-8.3, p<0.001; adjusted OR for high urine renin=2.0 per SD increase, 95% CI 1.2-3.3, p=0.005). Plasma IL-6 did not demonstrate a univariate association with risk of high urine renin (OR=1.3 per SD increase, 95% CI 0.9-2.0, p=0.16). Although a trend toward association with urine angiotensinogen (OR=1.5 per SD increase, 95% CI 0.98-2.3, p=0.06) was observed, it was eliminated with adjustment for urine IL-6 (adjusted OR=1.1, 95% CI 0.7-1.7, p=0.76).

Association with Survival

Over a median follow-up time of 713 days, 32 deaths occurred. Consistent with previous reports, increases in plasma IL-6 were associated with a higher risk of mortality (univariate HR=2.8 per SD increase, 95% CI 2.0-4.0, p<0.001). Plasma IL-6 remained associated with mortality after multivariable adjustment for baseline characteristics including age, race, baseline NT-proBNP levels, use of ACE-I or ARB, home loop diuretic dose and eGFR (adjusted HR=2.3 per SD increase, 95% CI=1.5-3.7, p<0.001). In contrast, urine IL-6 was not associated the risk of mortality (univariate HR=1.3 per SD increase, 95% CI 0.9-1.8, p=0.15; adjusted HR=1.02, 95% CI=0.6-1.6, p=0.93).

SUMMARY

Plasma and urine IL-6 levels capture distinctive aspects of the role of IL-6 in cardiorenal disease pathophysiology. Plasma IL-6 levels are associated with global measures of disease severity such as risk of mortality. In contrast, urine IL-6, likely a measure of kidney inflammation, is strongly correlated with multiple measures of cardiorenal syndrome ("CRS") in these heart failure patients, including diuretic resistance, renin angiotensin aldosterone and system (RAAS) activation, and lower estimated glomerular filtration rate (eGFR).

These data demonstrate that urine IL-6 level is a useful biomarker for renal inflammation, and is particularly useful in assessing renal symptoms in heart failure patients. In addition, serial urine IL-6 levels should prove useful in monitoring and assessing the renal benefit of therapeutic interventions in heart failure.

Example 2: TMPRSS6 Genotype Stratifies Heart Failure Patients Whose Renal Symptoms are Predicted to be Responsive to IL-6 Antagonists The data obtained in Example 1 also predict that treatment with an IL-6 antagonist should be effective in reducing renal inflammation in heart failure patients.

However, because infection is often a precipitating cause of acute decompensation in heart failure patients, it is important to limit anti-cytokine and other immunosuppressive therapies to those heart failure patients who are likely to respond with improved renal and/or cardiac function. The cost of chronic IL-6 antagonist therapy also militates for limiting treatment to those heart failure patients who are likely to respond with improved renal and/or cardiac function.

Analysis conducted in Example 1 was expanded to 129 patients. FIG. 1A is a bar graph showing diuretic efficiency ("DE") by tertiles of urine IL-6, confirming the inverse correlation of urinary IL-6 with diuretic efficiency observed in the 98 patient subset. FIG. 1B is a bar graph showing diuretic efficiency ("DE") by tertiles of plasma IL-6 in these 129 patients, confirming an inverse correlation of plasma IL-6 with diuretic efficiency (uncorrected by urinary IL-6 levels).

Each patient's genotype at the rs855791 single nucleotide polymorphism ("SNP") in transmembrane protease serine 6 ("TMPRSS6") was further assessed. The TMPRSS6 polypeptide, also known as Matriptase-2 (MT2), cleaves hemojuvelin and inhibits bone morphogenetic protein signaling. The rs855791 (G2321A) SNP alters the TMPRSS6 protein sequence: the allele with highest frequency in the human population (the major allele) is 2321G, encoding 736A; the allele with lowest frequency in the human population (minor allele) is 2321A, encoding 736V.

Genomic DNA was isolated from buffy coats using ReliaPrep large volume HT gDNA isolation system on the HSM Instrument (Promega, Madison, USA). The purity of the isolated DNA was assessed by Nanodrop. Genotyping was carried out at the Yale Centre for Genome analysis. Whole genome genotyping was done using Infinium® Exome-24 v1.0 BeadChip Kit from Illumina using standard protocols suggested by the manufacturer (Illumina, Inc., San Diego, CA). The amplification, fragmentation, precipitation, resuspension and hybridization steps were done manually. The arrays were scanned on the Illumina Hiscan instrument. The Illumina HiScan or iScan System scans the BeadChip, using a laser to excite the fluorophore of the single-base extension product on the beads. The scanner records high resolution images of the light emitted from the fluorophores. The Illumina GenomeStudio Genotyping Module, included with the Illumina Infinium Assay system, was used for extracting genotyping data from intensity data files (*.idat files) collected from the Illumina HiScan System. The Infinium Exome-24 v1.0 BeadChip contains over 240,000 putative functional exonic variants selected from over 12,000 individual human exome and whole-genome sequences. The >240,000 markers represent diverse populations, including European, African, Chinese, and Hispanic individuals, and a range of common conditions, such as type 2 diabetes, cancer, metabolic, and psychiatric disorders. Detailed Illumina genotyping protocol is available at support.illumina.com (infinium_hts_assay_protocol_user_guide_15045738_a.pdf) . The details of the SNPs in this exome chip are available at support.illumina.com/downloads/infinium-exome-24-v1-0-product-files.html.

As shown in FIG. 2A, urine levels of IL-6 were inversely correlated with diuretic efficiency only in the patients having at least one copy of the major allele of the TMPRSS6 rs855791 SNP (FIG. 2A, right panel, "AG+GG"); urine levels of IL-6 are not significantly correlated with diuretic efficiency in patients homozygous for the minor allele (FIG. 2A, left panel, "AA").

As shown in FIG. 2B, plasma levels of IL-6 correlated inversely with diuretic efficiency only in the patients having at least one copy of the major allele of the TMPRSS6 rs855791 SNP (FIG. 2B, right panel, "AG+GG"); plasma levels of IL-6 are not significantly correlated with diuretic efficiency in patients homozygous for the minor allele (FIG. 2B, left panel, "AA").

These data indicate that treatment of heart failure with an IL-6 antagonist will only improve renal symptoms in heart failure patients having at least one copy of the TMPRSS6 rs855791 major allele.

Example 3: Correlation of IL-6 with the Expression of NKCC2, ENaC-Beta, and NCC in the Absence or Presence of Ruxolitinib Methods The mouse M1 CCD cell line (American Type Culture Collection (ATCC), Cat# CRL-2038) was maintained the cell culture medium containing equal amount of DMEM (Sigma-Aldrich, Cat#D6046) and Han F12 (Sigma-Aldrich, Cat#11765-047), supplemented with 5% Fetal Bovine Serum (FBS), 1% Penicillin-Streptomycin (Thermo Fisher Scientific, Cat#15140-122), 1% Insulin-Transferrin-Selenium (Thermo Fisher Scientific, Cat#51500-056) and 100 nM Dexamethasone (Sigma-Aldrich, Cat# D4902-100MG).

M1 CCD cells were seeded at 1 million/well in 6-well plate in the cell culture medium, and incubated overnight in a 37° C., 5% $CO_2$ incubator on Day 0. The cell culture medium was changed to DMEM/F12 serum-free medium on Day 1 and the cells were incubated overnight in a 37° C., 5% $CO_2$ incubator. On Day 2, the serum-free medium was removed and the cell culture medium was added to each well. Ruxolitinib (Selleckchem, Cat# S1378) was added at the final concentration of 1 μM or 100 μM 10 min before the addition of IL-6 (Sigma-Aldrich, Cat# SRP3096-20UG) at the final concentration of 10 ng/mL, 100 ng/mL, or 500 ng/mL. A control well without Ruxolitinib or IL-6 was included. The cells were treated for 24 hours with IL-6 and/or Ruxolitinib. The cells of each well were washed with once with 1×PBS and collected in 250 μL 1×PIPA buffer (10×, Millipore, Cat#20-188) supplemented with 1% protease inhibitor cocktail (100×, Thermo Fisher Scientific, Cat#78430). The sample were analyzed by immunoblotting using anti-NKCC2 antibody (Millipore, Cat# AB3562P), anti-ENaC-beta antibody (Millipore, Cat# AB3532P), or anti-NCC antibody (Millipore, Cat# AB3553) and the protein expression was quantified. Each experiment was done in triplicate.

Results

Figure 4A:
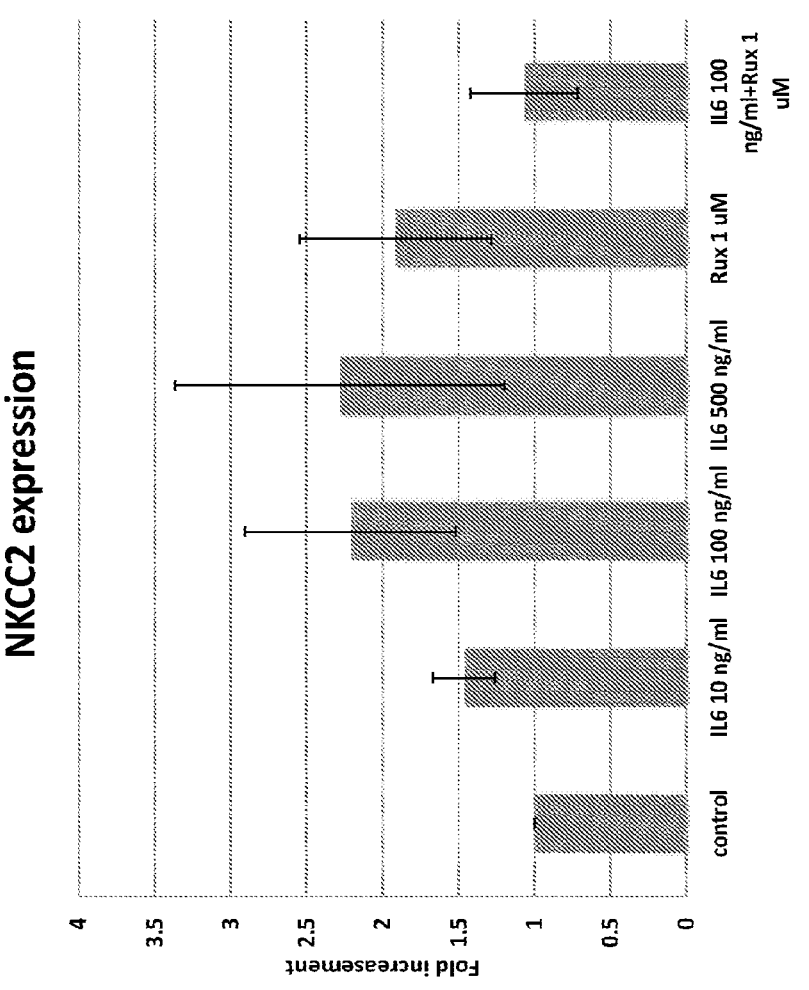
FIGS. 4A, 4B, and 4C show the expression of NKCC2, ENaC-beta, and NCC in M1 CCD cells after treatment with IL-6 and/or Ruxolitinib, with FIG. 4A showing the expression of NKCC2 after the treatment with IL-6 and/or Ruxolitinib.
Figure 4B:
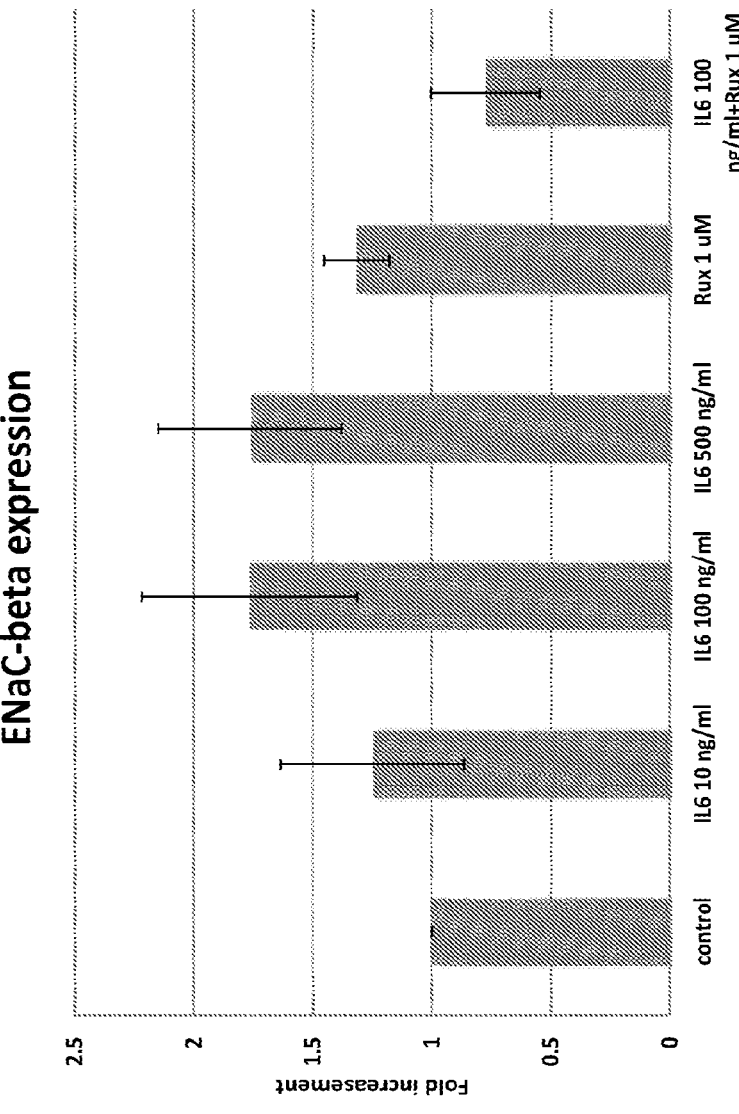
Figure 4C:
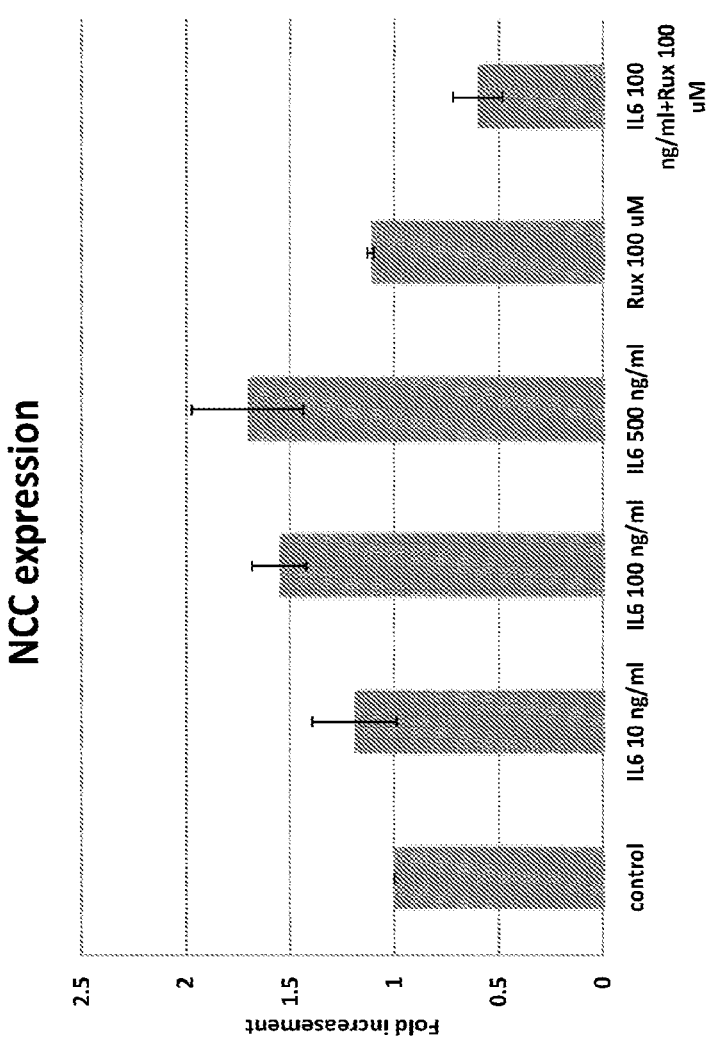

We examined the expression of NKCC2 (Na—K—Cl cotransporter 2), ENaC-beta (epithelial sodium channel, beta subunit), and NCC (sodium-chloride symporter) proteins in mouse M1 CCD cell line after treatment of IL-6 in the absence or presence of a JAK inhibitor, Ruxolitinib. The mouse M1 CCD cells are genotypically analogous to human cells homozygous for the TMPRSS6 rs855791 major allele. As shown in FIGS. 4A, 4B, and 4C, the treatment of IL-6 increased the expression of NKCC2, ENaC-beta, and NCC. Ruxolitinib blocked the effect of IL-6 on the ion transporter proteins.

Increased expression of these ion transporters provides a putative mechanism for IL-6 mediated diuretic resistance.

Because the increased expression is not known to be linked to hepcidin expression, these data suggested that IL-6 antagonism could be effective in treating diuretic resistance even in patients homozygous for the TMPRSS6 rs855791 minor allele.

Example 4: Correlation of IL-6 with the Expression of NKCC2, ENaC-Beta, and NCC in the Absence or Presence of Spironolactone Methods The mouse M1 CCD cell line (American Type Culture Collection (ATCC), Cat# CRL-2038) was maintained the cell culture medium containing equal amount of DMEM (Sigma-Aldrich, Cat#D6046) and Han F12 (Sigma-Aldrich, Cat#11765-047), supplemented with 5% Fetal Bovine Serum (FBS), 1% Penicillin-Streptomycin (Thermo Fisher Scientific, Cat#15140-122), 1% Insulin-Transferrin-Selenium (Thermo Fisher Scientific, Cat#51500-056) and 100 nM Dexamethasone (Sigma-Aldrich, Cat# D4902-100MG).

M1 CCD cells were seeded at 1 million/well in 6-well plate in the cell culture medium, and incubated overnight in a 37° C., 5% $CO_2$ incubator on Day 0. The cell culture medium was changed to DMEM/F12 serum-free medium on Day 1 and the cells were incubated overnight in a 37° C., 5% $CO_2$ incubator. On Day 2, the serum-free medium was removed and the cell culture medium was added to each well. Spironolactone (Selleckchem, Cat#54054) was added at the final concentration of 1 μM or 100 μM 10 min before the addition of IL-6 (Sigma-Aldrich, Cat# SRP3096-20UG) at the final concentration of 10 ng/mL, 100 ng/mL, or 500 ng/mL. A control well without Spironolactone or IL-6 was included. The cells were treated for 24 hours with IL-6 and/or Spironolactone. The cells of each well were washed with once with 1×PBS and collected in 250 μL 1×PIPA buffer (10×, Millipore, Cat#20-188) supplemented with 1% protease inhibitor cocktail (100×, Thermo Fisher Scientific, Cat#78430). The sample were analyzed by immunoblotting using anti-NKCC2 antibody (Millipore, Cat# AB3562P), anti-ENaC-beta antibody (Millipore, Cat# AB3532P), or anti-NCC antibody (Millipore, Cat# AB3553) and the protein expression was quantified. Each experiment was done in triplicate.

Results

Figure 5A:
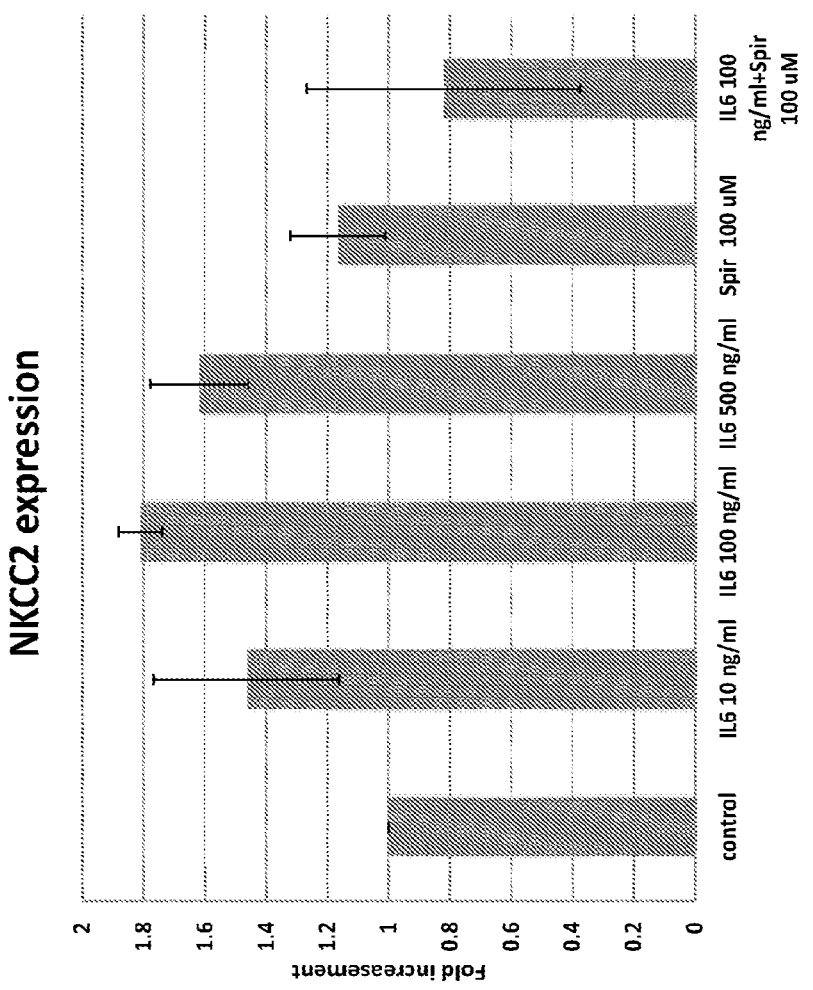
FIGS. 5A, 5B, and 5C show the expression of NKCC2, ENaC-beta, and NCC in M1 CCD cells after treatment with IL-6 and/or Spironolactone, with FIG. 5A showing the expression of NKCC2 after the treatment with IL-6 and/or Spironolactone.
Figure 5B:
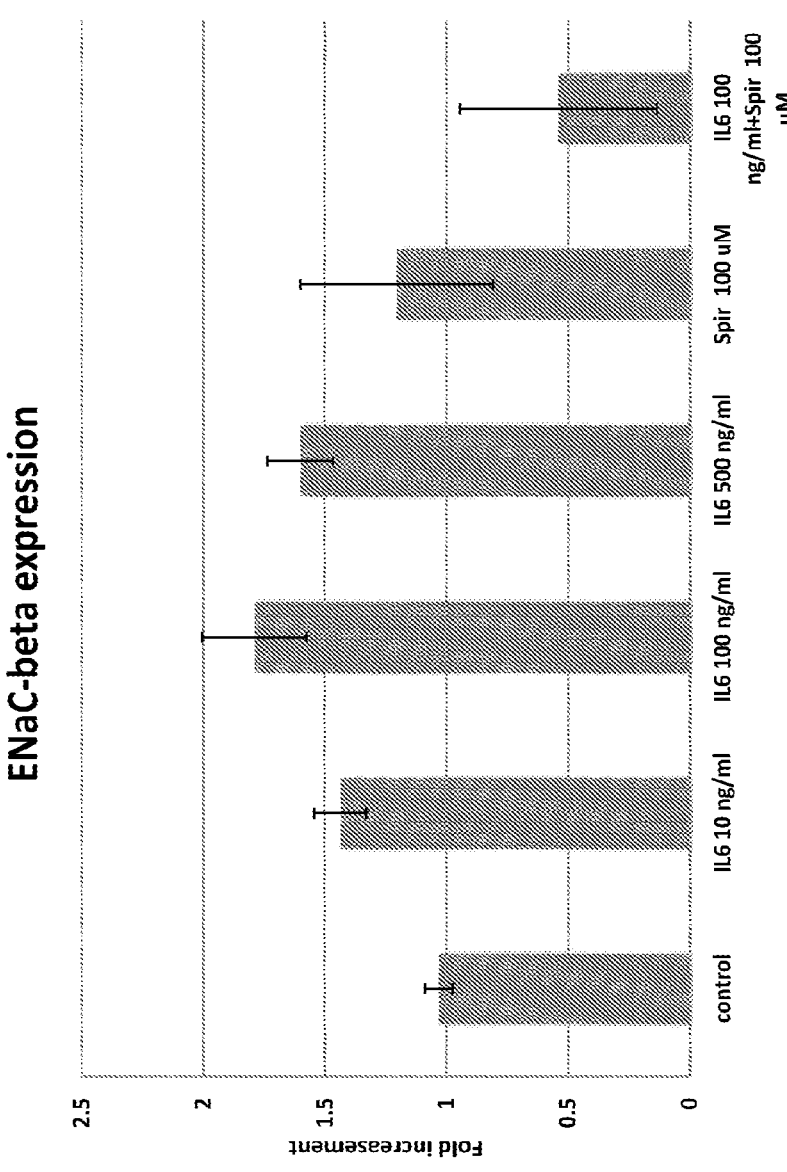
Figure 5C:
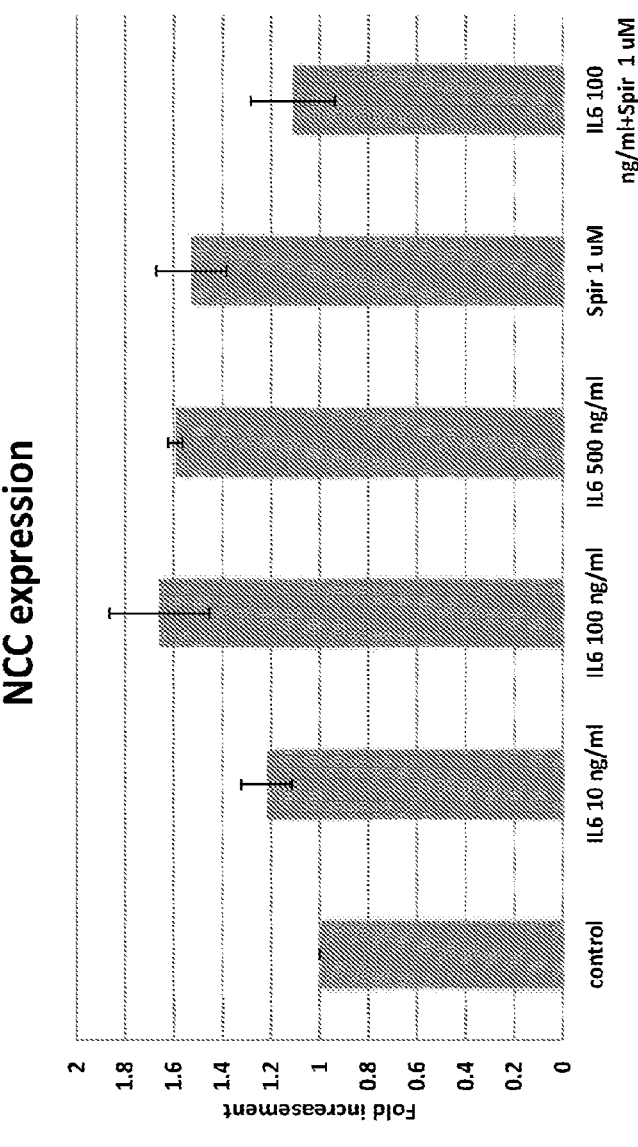

We examined the expression of NKCC2 (Na—K—Cl cotransporter 2), ENaC-beta (epithelial sodium channel, beta subunit), and NCC (sodium-chloride symporter) proteins in mouse M1 CCD cell line after treatment of IL-6 in the absence or presence of a potassium-sparing diuretic, Spironolactone. The mouse M1 CCD cells are genotypically analogous to human cells homozygous for the TMPRSS6 rs855791 major allele. As shown in FIGS. 5A, 5B, and 5C, the treatment of IL-6 increased the expression of NKCC2, ENaC-beta, and NCC. Spironolactone blocked the effect of IL-6 on the ion transporter proteins.

Increased expression of these ion transporters provides a putative mechanism for IL-6 mediated diuretic resistance.

Because the increased expression is not known to be linked to hepcidin expression, these data suggested that IL-6 antagonism could be effective in treating diuretic resistance even in patients homozygous for the TMPRSS6 rs855791 minor allele.

Example 5: Association of IL-6 with Diuretic Response in Patients Hospitalized for Acute Heart Failure (HF)

Methods. Data from the PROTECT trial (Weatherley et al., 2010, J. Card. Fail. 16:25-35; Massie et al., 2010, N. Engl. J. Med. 363:1419-1428) was analyzed according to tertiles of IL-6. The PROTECT trial was a randomized placebo-controlled trial testing the effect of Adenosine A1-Receptor Antagonist Rolofylline on dyspnea relief, risk of worsening renal function and clinical outcomes. The key inclusion and exclusion criteria of the trial are shown below.

TABLE A

| Inclusion | Exclusion |
| --- | --- |
| >18 years | Acute contrast-induced nephropathy |
| History of HF >14 days with diuretic therapy | Temp >38 or sepsis requiring IV |
| Hospitalized for ADHF* requiring IV diuretic | antimicrobial treatment |

TABLE A-continued

| Inclusion | Exclusion |
|---|---|
| therapy | Serum potassium <3.5 mEq/L |
| Within 24 hrs of presentation to the hospital | Ongoing or planned IV therapy for ADHF |
| Anticipated need for IV furosemide >40mg/ | with positive inotropic agents, vasopressors, |
| day for at least 24 hr | vasodilators |
| Impaired renal function defined as creatinine | BNP <500 pg/mL or NT-pro- |
| clearance of admission between 20 and 80 | BNP <2000 pg/mL |
| mL/min (Cockcroft-Gault) | Ongoing or planned treatment with |
| Systolic blood pressure >95 mm Hg | ultrafiltration |
| | Severe pulmonary disease |
| | Clinical evidence of acute coronary |
| | syndrome in the 2 weeks before screening |
| | Hgb <8 g/dL, or Hct <25%, or the |
| | need for a blood transfusion |
| | Systolic blood pressure $160 mm Hg at |
| | randomization |

*ADHF: dyspnea at rest or with minimal exertion and signs of fluid overload manifested by at least one of the following at time of randomization: JVP >8 cm, or Pulmonary rales ≥1/3 up the lung fields, not clearing with cough, or ≥2 Þ peripheral edema, or presacral edema In total, 2033 patients with ADHF were included in the PROTECT study. Of these patients, IL-6 was measured by Singulex in 1445 patients at admission (baseline), 1462 patients at day 2 (24 hr after baseline) and 1445 patients at day 7. Diuretic response was defined as weight change on day 4 per 40 mg of furosemide (or equivalent doses) administered from baseline to day 3. The primary endpoint of this study was all-cause mortality at 180 days.

Statistical analysis. Baseline characteristics are presented according to tertiles of IL-6. Differences between tertiles of baseline characteristics were tested using one-way analysis of variance (ANOVA), Kruskal Wallis or chi2-test where appropriate. Univariable linear regression was performed using diuretic response as the dependent variable and (log-transformed) IL-6 at baseline as the independent variable correcting for clinically relevant variables associated with diuretic response. Survival analysis was performed using Cox regression analysis correcting for clinically relevant variables and the PROTECT risk model (O'Connor et al., 2012, *Eur. J. Heart Fail.* 14:605-612). The PROTECT risk model includes: previous hospitalization for HF, edema, systolic blood pressure, sodium levels, BUN, creatinine and albumin at admission.

Figure 6:
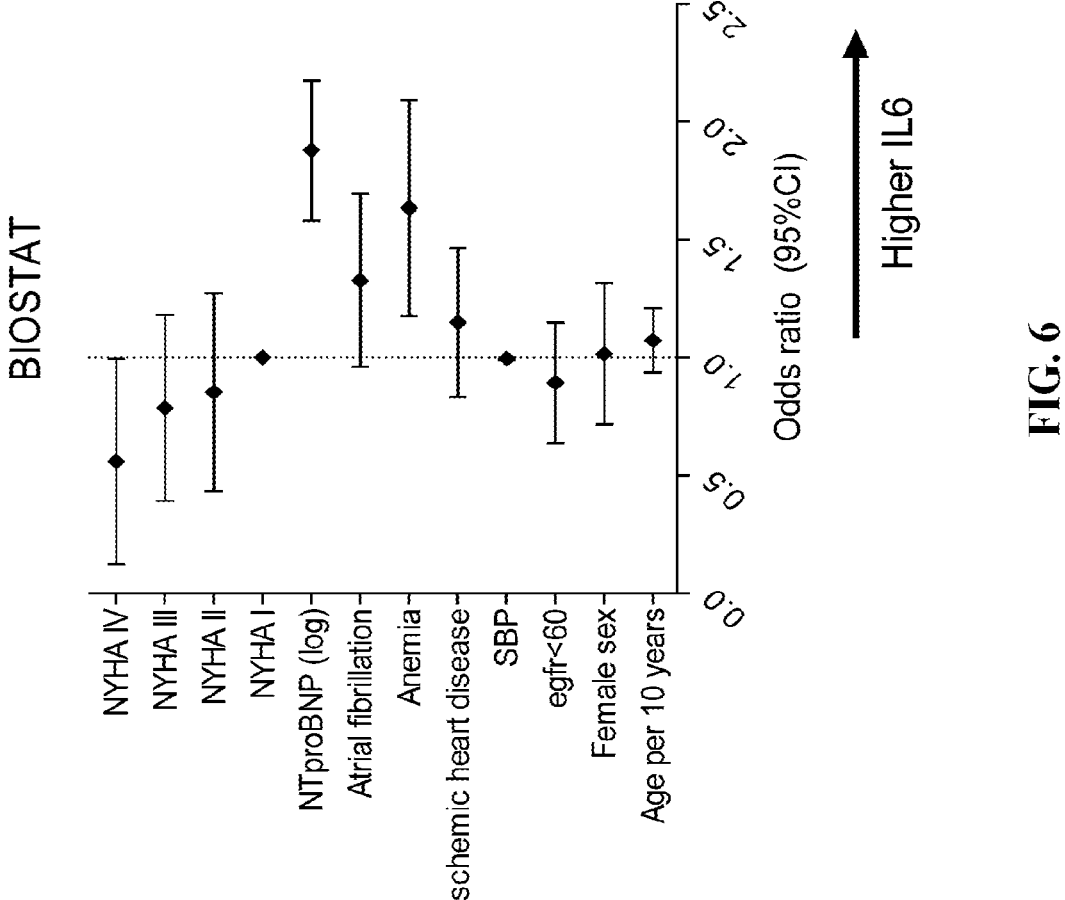
FIG. 6 shows the association of baseline characteristics with higher levels of IL-6 in the PROTECT trial described in Example 5.

Results. The baseline characteristics of the population are described in Table 4, below. Higher levels of IL-6 at baseline are associated with higher levels of BNP, anemia, eGFR <60 and older age (FIG. 6).

TABLE 4

Baseline Characteristics

| Factor | 1st tertile | 2nd tertile | 3rd tertile | p-value |
|---|---|---|---|---|
| N | 531 | 530 | 530 | |
| Demographics | 0.66-7.8 pg/mL | 7.9-16.1 pg/mL | 16.2-274.2 pg/mL | |
| Age | 69.2 (11.5) | 70.8 (11.0) | 72.5 (10.8) | <0.001 |
| Sex | 347 (65.3%) | 349 (65.8%) | 354 (66.8%) | 0.88 |
| BMI | 28.3 (5.8) | 28.8 (6.0) | 29.1 (6.2) | 0.093 |
| eGFR | 52.5 (20.2) | 47.2 (19.3) | 44.9 (17.4) | <0.001 |
| NYHA class | | | | |
| I/II | 107 (21.0%) | 71 (14.1%) | 96 (19.2%) | 0.008 |
| III | 267 (52.4%) | 263 (52.2%) | 237 (47.4%) | |
| IV | 136 (26.7%) | 170 (33.7%) | 167 (33.4%) | |
| LVEF | 30 (25, 40) | 30 (20, 40) | 30 (22, 40) | 0.35 |
| HFpEF | 42 (15.6%) | 39 (16.3%) | 38 (14.9%) | 0.92 |
| Systolic BP | 126.2 (17.4) | 124.5 (17.5) | 123.6 (17.4) | 0.043 |
| Diastolic BP | 75.3 (11.2) | 73.5 (12.1) | 72.3 (11.9) | <0.001 |
| Heart Rate | 79.2 (14.6) | 79.4 (15.8) | 81.3 (16.0) | 0.052 |
| Respiratory rate | 20.6 (4.3) | 21.2 (4.1) | 21.7 (4.9) | <0.001 |
| Atrial fibrillation | 95 (45.5%) | 92 (43.6%) | 78 (39.4%) | 0.45 |
| Valve disease | 196 (37.0%) | 195 (36.8%) | 208 (39.5%) | 0.61 |
| Mitral regurgitation | 174 (32.8%) | 178 (33.6%) | 184 (34.8%) | 0.78 |
| Aortic stenosis | 18 (3.4%) | 16 (3.0%) | 32 (6.0%) | 0.027 |
| Aortic regurgitation | 43 (8.1%) | 18 (3.4%) | 38 (7.2%) | 0.004 |
| Heart failure (HF) | 510 (96.0%) | 505 (95.3%) | 501 (94.5%) | 0.51 |
| Hospitalization for HF previous year | 258 (48.6%) | 266 (50.2%) | 259 (48.9%) | 0.86 |
| No. of HF hospitalizations, median (IQR) | 1.0 (1.0, 2.0) | 1.0 (1.0, 2.0) | 1.0 (1.0, 2.0) | 0.62 |
| Ischemic heart disease | 362 (68.4%) | 396 (74.9%) | 365 (68.9%) | 0.037 |
| Myocardial infarction | 255 (48.3%) | 296 (56.0%) | 242 (45.7%) | 0.003 |
| Hypertension | 424 (79.8%) | 422 (79.6%) | 428 (80.8%) | 0.89 |
| Stroke or PVD | 78 (14.7%) | 102 (19.3%) | 117 (22.2%) | 0.007 |
| Anemia | 174 (36.3%) | 216 (47.2%) | 238 (50.6%) | <0.001 |

TABLE 4-continued

Baseline Characteristics

| Factor | 1st tertile | 2nd tertile | 3rd tertile | p-value |
|---|---|---|---|---|
| Thyroid disease | 60 (11.3%) | 61 (11.5%) | 57 (10.8%) | 0.92 |
| Depression | 28 (5.3%) | 41 (7.7%) | 35 (6.6%) | 0.27 |
| Hyperlipidemia | 298 (56.1%) | 267 (50.5%) | 244 (46.0%) | 0.004 |
| Current smoker | 92 (17.4%) | 114 (21.6%) | 105 (19.8%) | 0.23 |
| COPD or asthma | 106 (20.0%) | 102 (19.2%) | 112 (21.2%) | 0.73 |
| Diabetes mellitus | 247 (46.5%) | 229 (43.2%) | 258 (48.7%) | 0.2 |
| History of Atrial Fibrillation/Flutter | 260 (49.2%) | 291 (55.0%) | 310 (58.8%) | 0.007 |
| AICD | 73 (13.7%) | 106 (20.0%) | 68 (12.8%) | 0.002 |
| Biventricular pacemaker | 54 (10.2%) | 60 (11.3%) | 47 (8.9%) | 0.41 |
| Pacemaker | 50 (9.5%) | 66 (12.5%) | 65 (12.3%) | 0.22 |
| Medication | | | | |
| Beta-blockers | 417 (78.7%) | 396 (74.7%) | 385 (72.6%) | 0.068 |
| ACEIs | 353 (66.6%) | 312 (58.9%) | 330 (62.3%) | 0.033 |
| ARBs | 85 (16.0%) | 85 (16.0%) | 71 (13.4%) | 0.38 |
| ACE-I/ARB | 424 (80.0%) | 390 (73.6%) | 393 (74.2%) | 0.026 |
| MRA | 264 (49.8%) | 226 (42.6%) | 229 (43.2%) | 0.033 |
| Digoxin | 159 (30.0%) | 153 (28.9%) | 146 (27.5%) | 0.68 |
| Nitrates | 136 (25.7%) | 146 (27.6%) | 135 (25.5%) | 0.68 |
| Hydralazine | 17 (3.2%) | 15 (2.8%) | 13 (2.5%) | 0.76 |
| CCBs | 74 (14.0%) | 71 (13.4%) | 81 (15.3%) | 0.67 |
| Signs and symptoms | | | | |
| Orthopnea | 445 (84.3%) | 440 (84.5%) | 435 (82.5%) | 0.65 |
| Dyspnea at rest (NYHA IV) | 264 (50.6%) | 304 (59.1%) | 327 (64.8%) | <0.001 |
| Angina pectoris | 134 (25.2%) | 117 (22.1%) | 111 (21.0%) | 0.24 |
| CCS Class III & IV | 48 (36.4%) | 38 (33.0%) | 29 (26.6%) | 0.27 |
| Edema | 82 (15.4%) | 151 (28.5%) | 184 (34.8%) | <0.001 |
| Jugular venous distension | 190 (39.7%) | 195 (40.5%) | 199 (41.6%) | 0.82 |
| Edema & raised JVP | 127 (26.5%) | 148 (30.7%) | 150 (31.4%) | 0.2 |
| Rales | 37 (7.0%) | 55 (10.4%) | 62 (11.7%) | 0.027 |

The association of IL-6 levels and diuretic response is shown in Table 5, below. The diuretic response was defined as weight change on day 4 per 40 mg of furosemide (or equivalent doses) administered from baseline to day 3.

TABLE 5

Diuretic Response

| | Beta | p-value |
|---|---|---|
| Univariable | 0.06 | 0.027 |
| Model 1 (age, sex) | 0.06 | 0.030 |
| Model 2 (model 1 + eGFR, BMI) | 0.06 | 0.035 |

Figure 7A:
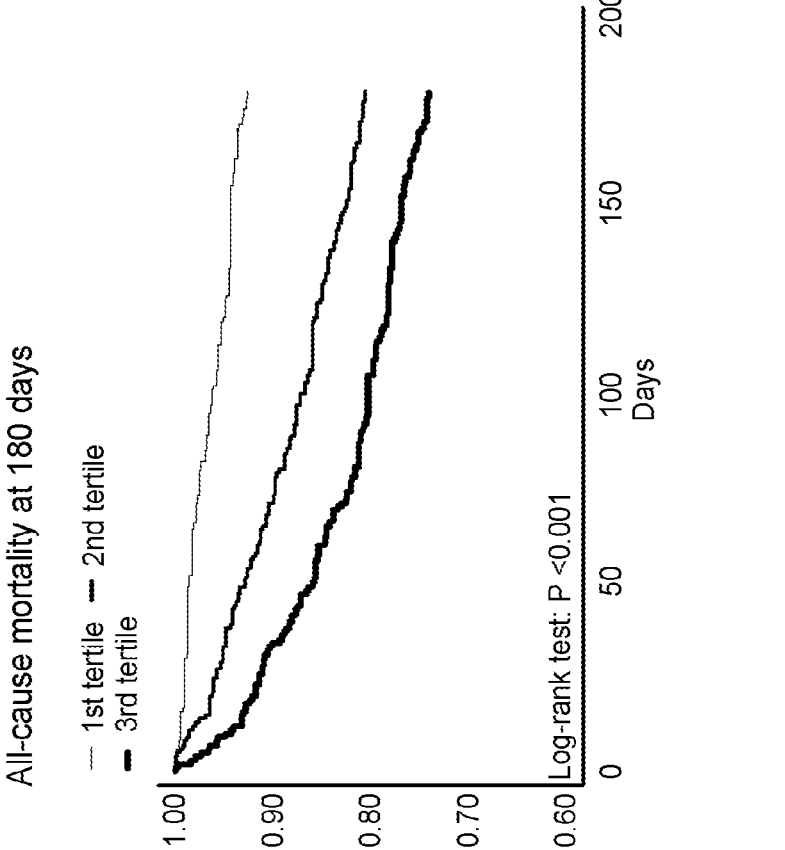
FIGS. 7A and 7B show the Kaplan-Meier survival curve by tertiles of IL-6, with FIG. 7A showing the all-cause mortality at 180 days and FIG. 7B showing all-cause mortality or cardiovascular related rehospitalization at 60 days.
Figure 7B:
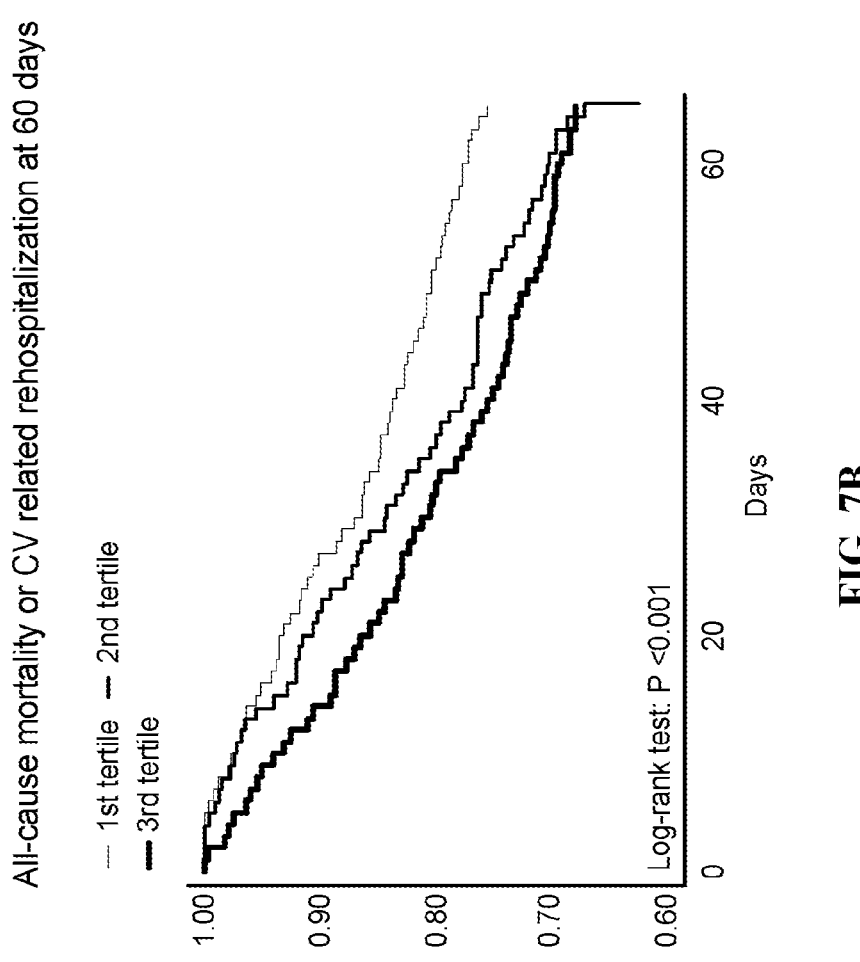

Table 6 and FIGS. 7A and 7B show the association of IL-6 levels with all-cause mortality at 180 days and the association of IL-6 levels with all-cause mortality at 60 days and/or cardiovascular related rehospitalization (CV hosp).

TABLE 6

Cox Regression Results

| | All-cause mortality at 180 days | 60 days mortality and/or CV hosp |
|---|---|---|
| Univariable | 1.59 (1.43-1.76) <0.001 | 1.14 (1.04-1.26) 0.007 |
| Model 1 | 1.57 (1.41-1.74) <0.001 | 1.14 (1.04-1.26) 0.007 |
| Model 2 | 1.55 (1.39-1.72) <0.001 | 1.11 (1.00-1.22) 0.049 |
| Model 3 | 1.50 (1.35-1.68) <0.001 | 1.09 (0.99-1.21) 0.087 |

TABLE 6-continued

Cox Regression Results

| | All-cause mortality at 180 days | 60 days mortality and/or CV hosp |
|---|---|---|
| PROTECT model | 1.41 (1.26-1.58) <0.001 | 1.06 (0.95-1.17) 0.309 |

Figure 8A:
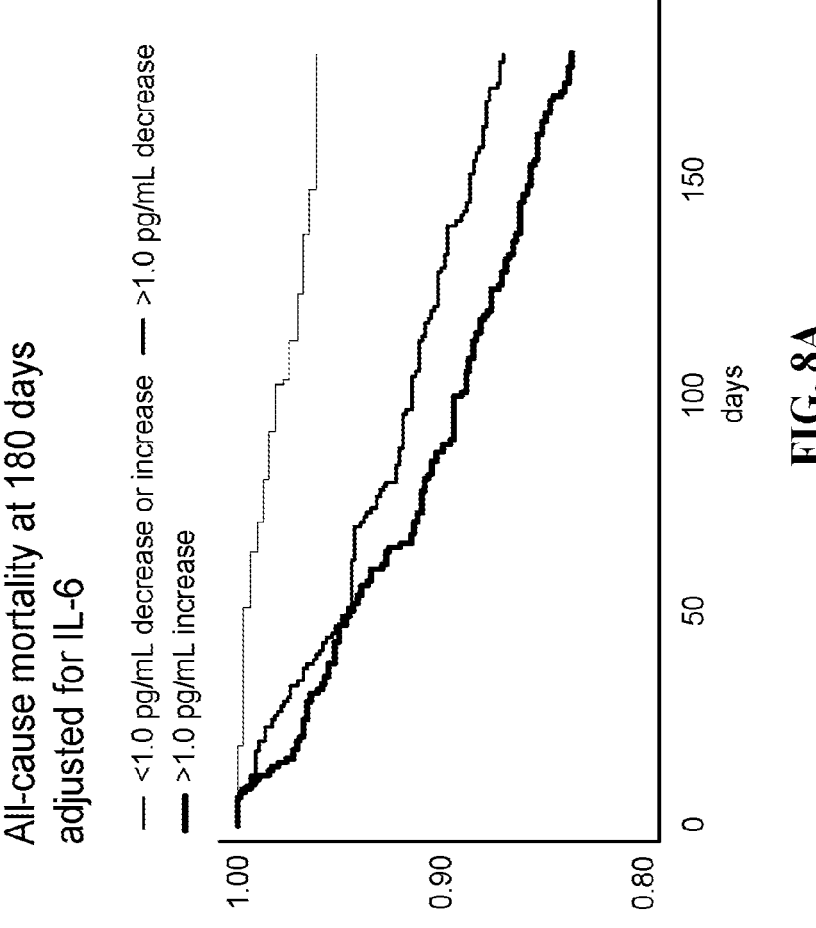
FIGS. 8A and 8B show the Kaplan-Meier survival curve for change of IL-6 between baseline and day 7, with FIG. 8A showing the all-cause mortality at 180 days and FIG. 8B showing all-cause mortality or cardiovascular related rehospitalization at 60 days.
Figure 8B:
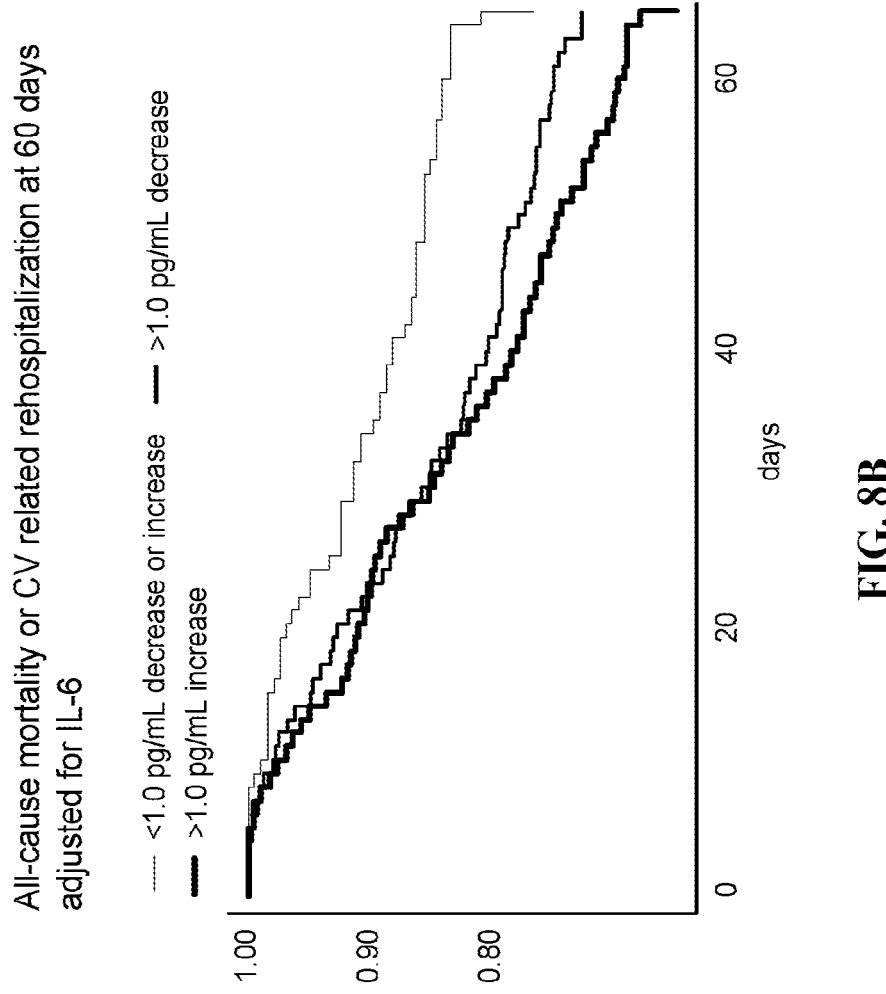

Model 1: age, sex
Model 2: model 1 + eGFR, BMI
Model 3: model 2 + BNP
PROTECT model: age, previous hospitalization for HF, edema at admission, sodium, bun (log), creatinine (log) and albumin Table 7 and FIGS. 8A and 8B show that an increase in IL-6 levels at day 7 compared to the baseline predicts adverse outcomes.

TABLE 7

Cox Regression Results

| | >1 pg/mL decrease | <1.0 pg/mL increase/decrease | >1.0 pg/mL increase |
|---|---|---|---|
| | 180 days all-cause mortality | | |
| Univariable | 2.13 (1.16-3.91) 0.014 | ref | 3.01 (1.65-5.49) <0.001 |
| Model 1 | 1.79 (0.96-3.32) 0.066 | ref | 2.80 (1.53-5.11) 0.001 |
| Model 2 | 1.80 (0.95-3.44) 0.073 | ref | 2.65 (1.41-4.97) 0.002 |
| Model 3 | 1.65 (0.87-3.16) 0.128 | ref | 2.35 (1.25-4.44) 0.008 |
| PROTECT | 1.71 (0.90-3.26) 0.101 | ref | 2.38 (1.30-4.47) 0.007 |

TABLE 7-continued

Cox Regression Results

| | >1 pg/mL decrease | <1.0 pg/mL increase/decrease | >1.0 pg/mL increase |
|---|---|---|---|
| | 60 days mortality and/or CV hosp | | |
| Univariable | 1.31 (0.91-1.92) 0.146 | ref | 1.83 (1.26-2.65) 0.001 |
| Model 1 | 1.31 (0.89-1.92) 0.002 | ref | 1.81 (1.25-2.62) 0.002 |
| Model 2 | 1.29 (0.88-1.92) 0.187 | ref | 1.70 (1.16-2.48) 0.006 |
| Model 3 | 1.28 (0.86-1.89) 0.223 | ref | 1.67 (1.14-2.45) 0.008 |
| PROTECT | 1.20 (0.81-1.78) 0.353 | ref | 1.57 (1.07-2.30) 0.020 |

Model 1: age, sex
Model 2: model 1 + eGFR, BMI
Model 3: model 2 + BNP
PROTECT model: age, previous hospitalization for HF, edema at admission, sodium, bun (log), creatinine (log) and albumin

Example 6: Association of IL-6 Levels with Outcomes in a Worsening Heart Failure Population Methods. Data from the BIOlogy Study to TAilored Treatment in Chronic Heart Failure (BIOSTAT-CHF) study was analyzed to investigate the association of IL-6 with outcomes in patients with worsening heart failure. In brief, BIOSTAT-CHF was a multicenter, multinational, prospective, observational study including 2516 patients from 69 centers in 11 European countries (Voors et al., 2016, *Eur. J. Heart Fail.* 18:716-726). We performed secondary analyses in the BIOSTAT-CHF study, excluding patients with ferritin <100 from subsequent analysis. Inclusion criteria for the index cohort include: patients with >18 years of age, having symptoms of new-onset or worsening HF, confirmed either by a LVEF of ≤40% or BNP and/or NT-proBNP plasma levels >400 pg/ml or >2,000 pg/ml, respectively. Furthermore, these patients had not been previously treated with an ACEi/ARBs and/or beta-blocker or they were receiving ≤50% of the target doses of these drugs at the time of inclusion and anticipated initiation or up-titration of ACEi/ARBs and beta-blockers. All patients needed to be treated with loop diuretics.

TABLE B

Inclusion criteria

Age >18
Diagnosed with HF
Previous documented admission with HF requiring diuretic treatment
Treated with furosemide >20 mg/day or equivalent
Not previously treated or receiving <50% of target doses of ACE inhibitors/ARBs and/or beta-blockers according to 2008 ESC guidelines
Anticipated uptitration of ACE inhibitors/ARBs and/or beta-blockers In total, IL-6 was measured in 2329 patients with worsening HF from the BIOSTAT-CHF study. The primary outcome of this study was a composite outcome of all-cause mortality and hospitalization for HF.

Statistical analyses. Baseline characteristics are presented according to tertiles of IL-6. Differences between tertiles of baseline characteristics were tested using one-way analysis of variance (ANOVA), Kruskal Wallis or chi2-test where appropriate. Survival analysis was performed using Cox regression analysis correcting for clinically relevant variables and the BIOSTAT-CHF risk model. The BIOSTAT-CHF risk model for all-cause mortality and/or hospitalization for heart failure includes: age, N-terminal pro-B-type natriuretic peptide (NT-proBNP), hemoglobin (Hb), the use of a beta-blocker at time of inclusion, a HF-hospitalization in year before inclusion, peripheral edema, systolic blood pressure, high-density lipoprotein cholesterol and sodium (Voors et al., 2017, *Eur. J. Heart Fail.* 19:627-634). We performed interaction analysis between ferritin levels and IL-6 for the primary outcome. To investigate the association of IL-6 with outcomes depending on the position of the TMPRS6 SNP (rs855791).

Figure 9:
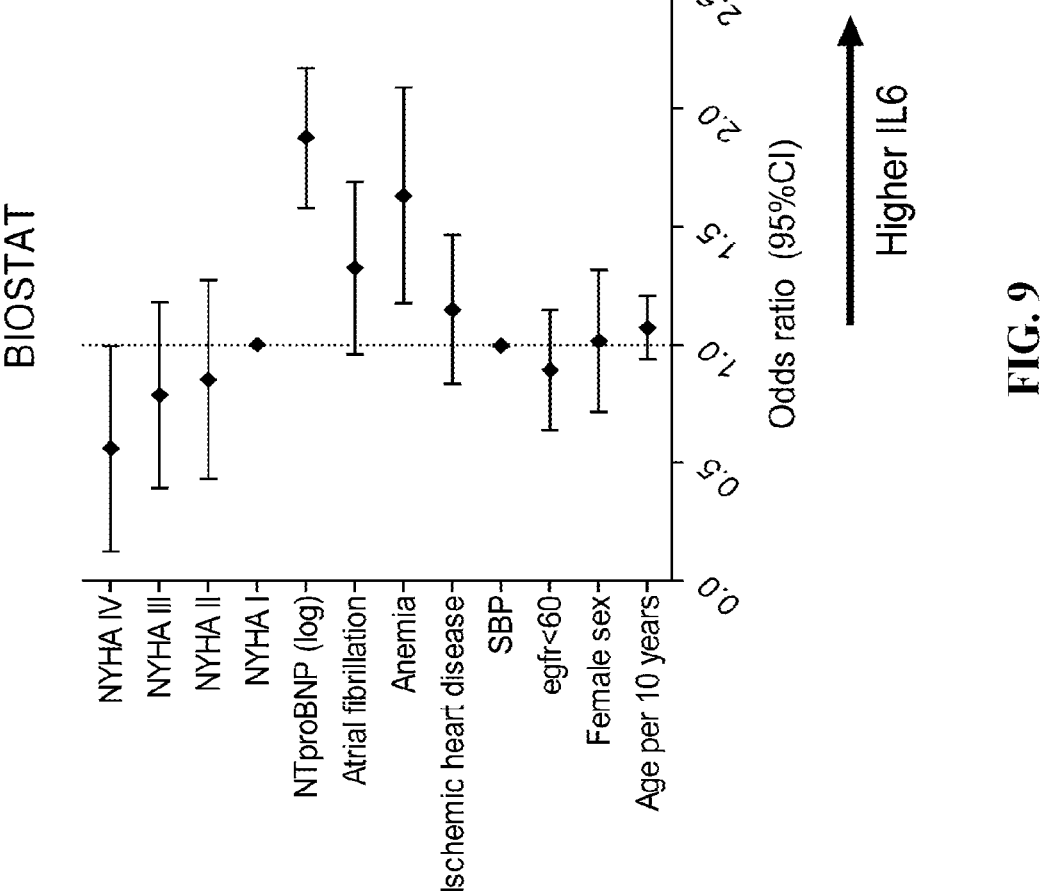
FIG. 9 shows the association of baseline characteristics with higher levels of IL-6 in the BIOSTAT-CHF study described in Example 6.

Results. The baseline characteristics of the population are described in Table 8, below. Higher levels of IL-6 at baseline are associated with higher levels of NTproBNP and Anemia (FIG. 9).

TABLE 8

Baseline Characteristics

| Factor | 1st tertile | 2nd tertile | 3rd tertile | p-value |
|---|---|---|---|---|
| N | 781 | 775 | 773 | |
| Demographics | 0.3-3.4 pg/mL | 3.5-7.8 pg/mL | 7.9-260.7 pg/mL | |
| Age | 66.3 (12.2) | 69.3 (11.7) | 70.9 (11.7) | <0.001 |
| Female | 200 (25.6%) | 200 (25.8%) | 212 (27.4%) | 0.67 |
| HF status | | | | |
| HFrEF | 607 (84.1%) | 568 (81.6%) | 524 (78.3%) | <0.001 |
| HFmrEF | 92 (12.7%) | 74 (10.6%) | 87 (13.0%) | |
| HFpEF | 23 (3.2%) | 54 (7.8%) | 58 (8.7%) | |
| BMI | 27.9 (5.1) | 27.7 (5.6) | 27.7 (5.6) | 0.77 |
| Ischemic etiology | 329 (43.2%) | 353 (46.4%) | 357 (46.7%) | 0.31 |
| NYHA | | | | |
| I | 70 (9.0%) | 82 (10.6%) | 62 (8.0%) | 0.005 |
| II | 400 (51.2%) | 355 (45.8%) | 320 (41.4%) | |
| III | 199 (25.5%) | 216 (27.9%) | 251 (32.5%) | |
| IV | 22 (2.8%) | 25 (3.2%) | 33 (4.3%) | |
| NA | 90 (11.5%) | 97 (12.5%) | 107 (13.8%) | |
| Systolic BP | 126.4 (20.0) | 124.3 (22.4) | 123.7 (23.5) | 0.034 |
| Diastolic BP | 76.7 (12.7) | 74.8 (13.4) | 73.5 (14.0) | <0.001 |
| LVEF | 30.6 (8.9) | 30.9 (11.1) | 31.3 (11.7) | 0.54 |

TABLE 8-continued

| | Baseline Characteristics | | | |
|---|---|---|---|---|
| Factor | 1st tertile | 2nd tertile | 3rd tertile | p-value |
| Heart Rate | 76.4 (18.2) | 80.1 (18.9) | 83.6 (21.0) | <0.001 |
| Signs and symptoms | | | | |
| Peripheral edema | | | | |
| Not Present | 352 (57.2%) | 253 (39.7%) | 180 (26.4%) | <0.001 |
| Ankle | 170 (27.6%) | 188 (29.5%) | 221 (32.5%) | |
| Below Knee | 83 (13.5%) | 156 (24.5%) | 194 (28.5%) | |
| Above Knee | 10 (1.6%) | 40 (6.3%) | 86 (12.6%) | |
| Elevated JVP | | | | |
| No | 420 (76.5%) | 318 (58.9%) | 289 (53.7%) | <0.001 |
| Yes | 106 (19.3%) | 190 (35.2%) | 216 (40.1%) | |
| Uncertain | 23 (4.2%) | 32 (5.9%) | 33 (6.1%) | |
| Hepatomegaly | 75 (9.6%) | 128 (16.6%) | 132 (17.1%) | <0.001 |
| Orthopnea | 168 (21.6%) | 273 (35.3%) | 361 (46.8%) | <0.001 |
| Medical history | | | | |
| Anemia | 158 (23.6%) | 271 (38.1%) | 348 (47.0%) | <0.001 |
| Atrial fibrillation | 293 (37.5%) | 372 (48.0%) | 387 (50.1%) | <0.001 |
| Diabetes mellitus | 208 (26.6%) | 270 (34.8%) | 276 (35.7%) | <0.001 |
| COPD | 113 (14.5%) | 126 (16.3%) | 163 (21.1%) | 0.002 |
| Renal disease | 152 (19.5%) | 229 (29.5%) | 261 (33.8%) | <0.001 |
| Hypertension | 486 (62.2%) | 496 (64.0%) | 473 (61.2%) | 0.51 |
| Peripheral artery disease | 60 (7.7%) | 92 (11.9%) | 105 (13.6%) | <0.001 |
| Stroke | 59 (7.6%) | 84 (10.8%) | 76 (9.8%) | 0.075 |
| PCI | 163 (20.9%) | 166 (21.4%) | 173 (22.4%) | 0.76 |
| CABG | 120 (15.4%) | 122 (15.7%) | 156 (20.2%) | 0.02 |
| Medication | | | | |
| Loop diuretics | 779 (99.7%) | 769 (99.2%) | 769 (99.5%) | 0.36 |
| ACE/ARB | 601 (77.0%) | 564 (72.8%) | 518 (67.0%) | <0.001 |
| Beta blocker | 675 (86.4%) | 654 (84.4%) | 603 (78.0%) | <0.001 |
| Aldosterone antagonist | 446 (57.1%) | 411 (53.0%) | 382 (49.4%) | 0.01 |
| Laboratory | | | | |
| Hemoglobin | 13.7 (1.7) | 13.2 (1.8) | 12.7 (2.0) | <0.001 |
| Total cholesterol | 4.5 (3.7, 5.5) | 4.1 (3.4, 4.9) | 3.7 (3.1, 4.5) | <0.001 |
| AST | 24.0 (19.0, 32.0) | 25.0 (19.0, 34.0) | 27.0 (20.0, 39.0) | <0.001 |
| ALT | 25.0 (18.0, 37.0) | 25.0 (17.0, 37.0) | 23.5 (15.0, 40.0) | 0.12 |
| Sodium | 140.0 (138.0, 142.0) | 140.0 (137.0, 142.0) | 139.0 (136.0, 141.0) | <0.001 |
| Potassium | 4.3 (4.0, 4.6) | 4.2 (3.9, 4.6) | 4.2 (3.8, 4.6) | <0.001 |
| HbA1c | 6.0 (5.6, 6.7) | 6.5 (5.9, 7.5) | 6.5 (5.9, 7.3) | <0.001 |
| NT-proBNP | 2661.0 (1445.0, 4820.0) | 4344.0 (2517.0, 7837.0) | 5734.5 (3141.0, 11452.0) | <0.001 |
| Troponin-I | 0.0 (0.0, 0.1) | 0.0 (0.0, 0.1) | 0.0 (0.0, 0.1) | <0.001 |

Figure 10A:
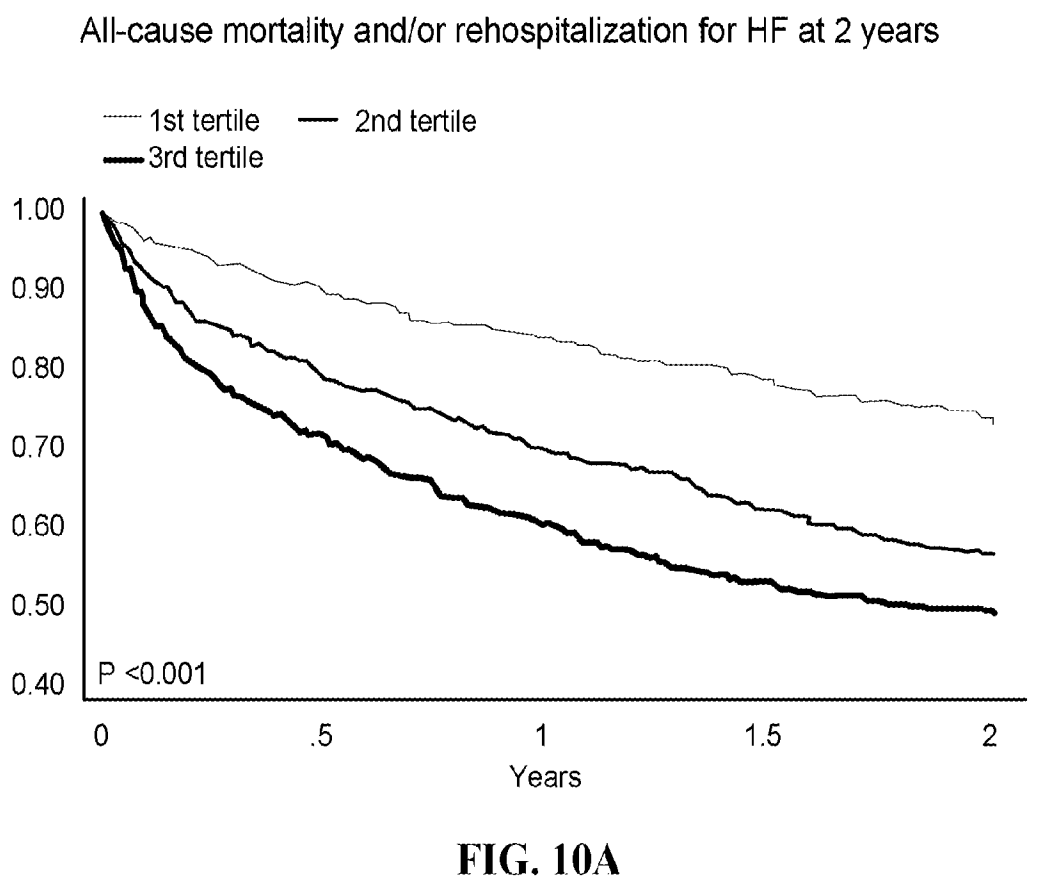
Figure 10B:
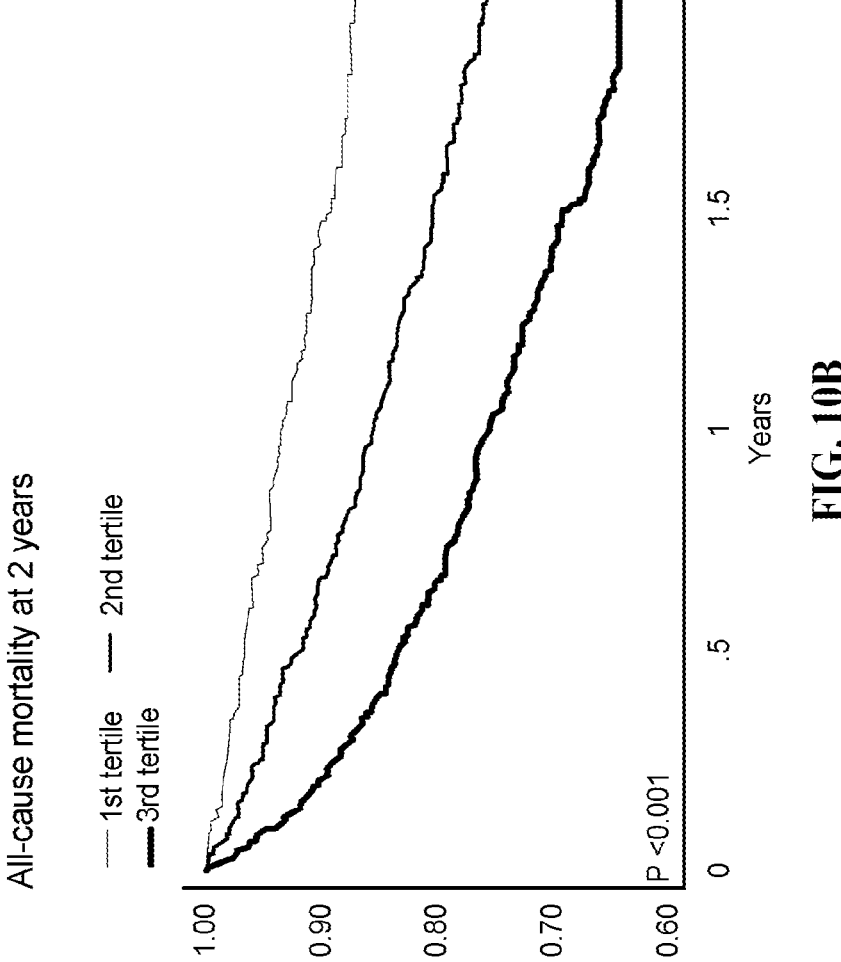

As shown in Table 9 and FIGS. 10A and 10B, levels of IL-6 measured at baseline were associated with the combined outcome of all-cause mortality and/or a hospitalization for HF as well as all-cause mortality alone at two years.

TABLE 9

| | Cox Regression Analyses | |
|---|---|---|
| | All-cause mort and/or HF hosp at 2 years HR (95% CI) p-value | All-cause mortality at 2 years HR (95% CI) p-value |
| Univariable | 1.38 (1.31-1.46) <0.001 | 1.42 (1.32-1.53) <0.001 |
| Model 1 | 1.34 (1.26-1.42) <0.001 | 1.48 (1.38-1.58) <0.001 |
| Model 2 | 1.25 (1.17-1.33) <0.001 | 1.34 (1.24-1.44) <0.001 |

TABLE 9-continued

| | Cox Regression Analyses | |
|---|---|---|
| | All-cause mort and/or HF hosp at 2 years HR (95% CI) p-value | All-cause mortality at 2 years HR (95% CI) p-value |
| Model 3 | 1.24 (1.16-1.32) <0.001 | 1.33 (1.23-1.44) <0.001 |
| BIOSTAT model | 1.13 (1.04-1.19) 0.001 | 1.20 (1.11-1.31) <0.001 |

Model 1: Age, sex

Figure 11:
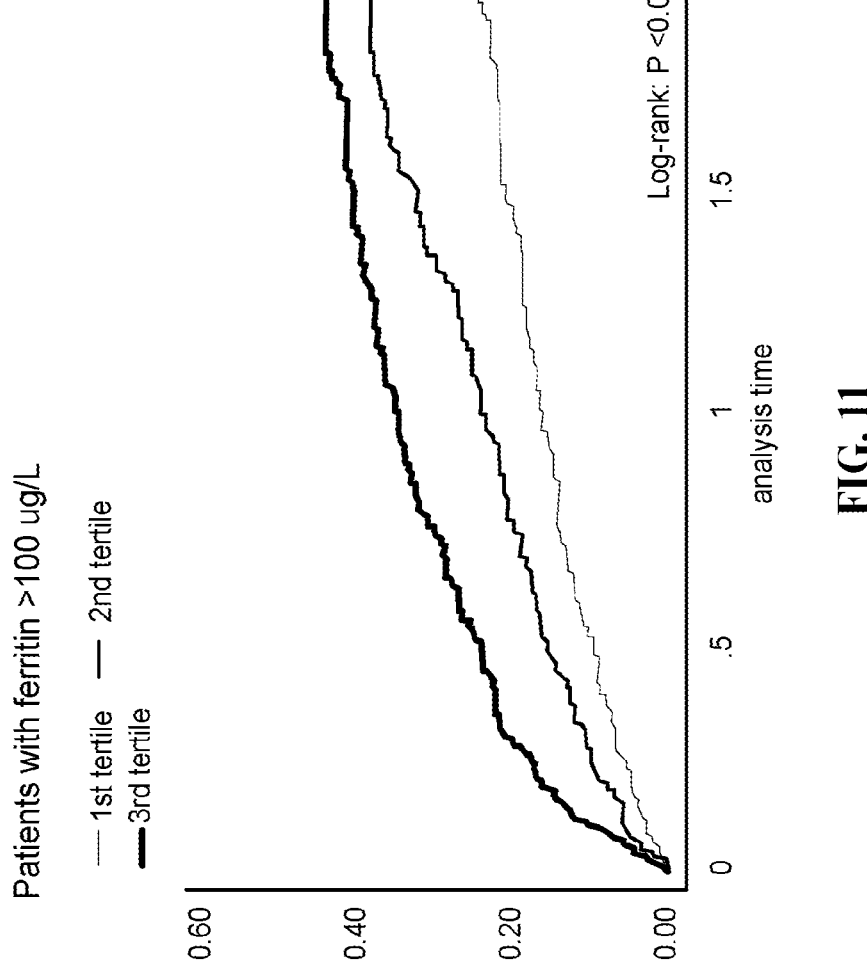
FIG. 11 show the analysis between ferritin levels and tertiles of IL-6.

Model 2: model 1 + BMI, country, hypertension (history of), diabetes (history of) and anemia Model 3: model 2 + beta-blocker at baseline, ACEi/ARB at baseline and MRA at baseline BIOSTAT model: age, N-terminal pro-B-type natriuretic peptide (NT-proBNP), hemoglobin (Hb), the use of a beta-blocker at time of inclusion, a HF-hospitalization in year before inclusion, peripheral edema, systolic blood pressure, high-density lipoprotein cholesterol and sodium As shown in Table 10 and FIG. 11, there is no differential association of IL-6 with outcome depending on ferritin status.

TABLE 10

| Cox Regression Analyses | | |
|---|---|---|
| | Ferritin >100 ug/L HR (95% CI) p-value | Interaction ferritin *IL-6 |
| Univariable | 1.39 (1.27-1.52) <0.001 | 0.610 |
| Model 1 | 1.35 (1.23-1.48) <0.001 | |
| Model 2 | 1.26 (1.14-1.40) <0.001 | |
| Model 3 | 1.26 (1.14-1.39) <0.001 | |
| BIOSTAT model | 1.11 (0.99-1.22) 0.052 | |

Model 1: Age, sex

Model 2: model 1 + BMI, country, hypertension (history of), diabetes (history of) and anemia Model 3: model 2 + beta-blocker at baseline, ACEi/ARB at baseline and MRA at baseline BIOSTAT model: age, N-terminal pro-B-type natriuretic peptide (NT-proBNP), hemoglobin (Hb), the use of a beta-blocker at time of inclusion, a HF-hospitalization in year before inclusion, peripheral edema, systolic blood pressure, high-density lipoprotein cholesterol and sodium As shown in Table 11, there was no differential association of IL-6 with outcome depending on TMPRSS6 genotype.

TABLE 11

| IL-6 according to TMPRSS6 allele | |
|---|---|
| TMPRSS6 | HR (95% CI) p-value |
| AA (n = 191) | 1.50 (1.19-1.89) 0.001 |
| AG (n = 579) | 1.34 (1.17-1.54) <0.001 |
| GG (n = 409) | 1.54 (1.32-1.79) <0.001 |

INCORPORATION BY REFERENCE

The disclosures of each and every patent, patent application, and publication cited herein are hereby incorporated herein by reference in their entirety.

EQUIVALENTS

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating a patient with diuretic resistant heart failure having at least one copy of the TMPRSS6 rs855791 allele who requires diuresis but is resistant to diuretics, comprising:

administering, in combination with a diuretic, a therapeutically effective amount of an IL-6 antagonist to the patient.

2. The method of claim 1, wherein the patient has acute heart failure.

3. The method of claim 1, wherein the patient has chronic heart failure.

4. The methods of claim 1, wherein the patient has cardiorenal syndrome.

5. The method of claim 4, wherein the patient has cardiorenal syndrome type 4.

6. The methods of claim 1, wherein the patient has kidney disease.

7. The method of claim 1, wherein the IL-6 antagonist is an anti-IL-6 antibody, or antigen-binding fragment or derivative thereof.

8. The method of claim 1, wherein the IL-6 antagonist is an anti-IL-6R antibody, or antigen-binding fragment or derivative thereof.

9. The method of claim 1, wherein the IL-6 antagonist is a JAK inhibitor.

10. The method of claim 1, wherein the IL-6 antagonist is a STAT3 inhibitor.

* * * * *